United States Patent [19]

Takaya et al.

[11] Patent Number: 4,622,318
[45] Date of Patent: Nov. 11, 1986

[54] 3-(SUBSTITUTED-ETHENYL OR ETHYNYL-THIOMETHYL) CEPHEMS

[75] Inventors: Takao Takaya, Kawanishi; Zenzaburo Tozuka, Toyonaka; Nobuyoshi Yasuda, Nishinomiya; Kohji Kawabata, Osaka, all of Japan

[73] Assignee: Fujisawa Pharmaceutical Co., Ltd., Osaka, Japan

[21] Appl. No.: 662,604

[22] Filed: Oct. 19, 1984

[30] Foreign Application Priority Data

Oct. 31, 1983 [GB] United Kingdom ............... 8329030

[51] Int. Cl.$^4$ ................ A61K 31/545; C07D 501/18; C07D 501/36
[52] U.S. Cl. .................................. 514/200; 514/204; 540/215; 540/224; 540/225; 540/226; 540/227; 540/229
[58] Field of Search ................ 544/16, 26, 27, 29, 544/24, 25; 514/200, 204

[56] References Cited

U.S. PATENT DOCUMENTS 4,256,739  3/1981  Woodward ................ 544/26

FOREIGN PATENT DOCUMENTS 29557  6/1981  European Pat. Off. ........... 544/26

*Primary Examiner*—Sidney Marantz
*Assistant Examiner*—Robert Benson
*Attorney, Agent, or Firm*—Oblon, Fisher, Spivak, McClelland, & Maier

[57] ABSTRACT

The invention relates to new cephem compounds of high antimicrobial activity of the formula:

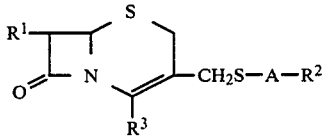

wherein $R^1$ is amino or a group of the formula:

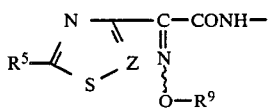

in which
$R^5$ is amino or a protected amino group,
$R^9$ is lower alkyl, lower alkenyl, lower alkynyl, cyclo(lower)alkenyl, carboxy(lower)alkyl, protected carboxy(lower)alkyl or saturated 4 to 8-membered heteromonocyclic group containing one sulfur atom, and
Z is N or CH,
$R^2$ is cyano, phenyl, pyridyl, lower alkylpyridyl, or tri(lower)alkylsilyl,
$R^3$ is carboxy or protected carboxy, and
A is —CH=CH— or —C≡C—, and pharmaceutically acceptable salt thereof.

5 Claims, No Drawings

3-(SUBSTITUTED-ETHENYL OR ETHYNYL-THIOMETHYL) CEPHEMS

The present invention relates to new cephem compounds and pharmaceutically acceptable salts thereof. More particularly, it relates to new cephem compounds and pharmaceutically acceptable salts thereof, which have antimicrobial activities, to processes for preparation thereof, to pharmaceutical composition comprising the same, and to a method of using the same therapeutically for the treatment of infectious diseases in human being and animals.

Accordingly, it is one object of the present invention to provide new cephem compounds and pharmaceutically acceptable salts thereof, which are highly active against a number of pathogenic microorganisms.

Another object of the present invention is to provide processes for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compounds and pharmaceutically acceptable salt thereof are novel and can be represented by the following general formula (I):

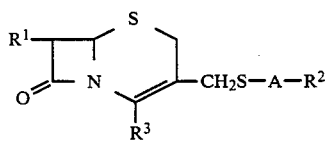

wherein
R$^1$ is amino or Protected amino,
R$^2$ is aryl which may have suitable substituent(s), a heterocyclic group which may have suitable substituent(s), cyano, hydrogen or tri(lower)alkylsilyl,
R$^3$ is carboxy or protected carboxy, and
A is —CH=CH— or —C≡C—,
and pharmaceutically acceptable salt thereof.

According to the present invention, the new cephem compound (I) can be prepared by various processes which are illustrated in the following schemes.

Process 1

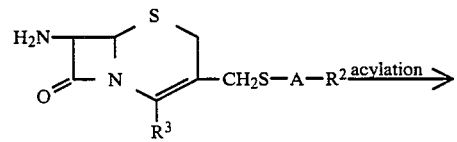

or its reactive derivative
at the amino group
or a salt thereof

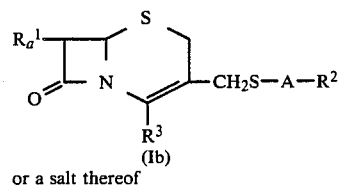

or a salt thereof

Process 2

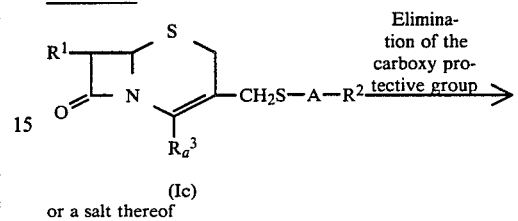

or a salt thereof

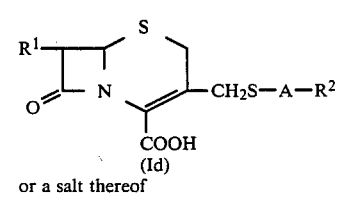

or a salt thereof

Process 3

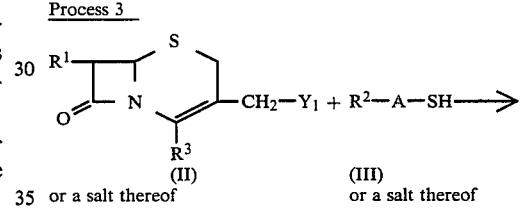

or a salt thereof

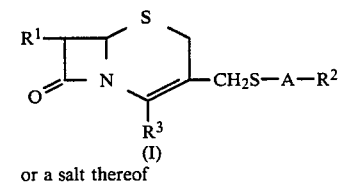

or a salt thereof

Process 4

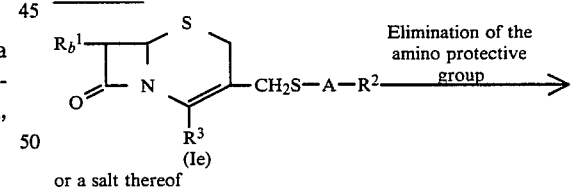

or a salt thereof

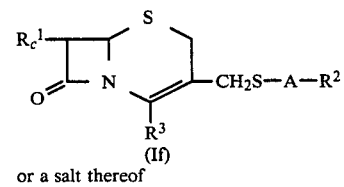

or a salt thereof

Process 5

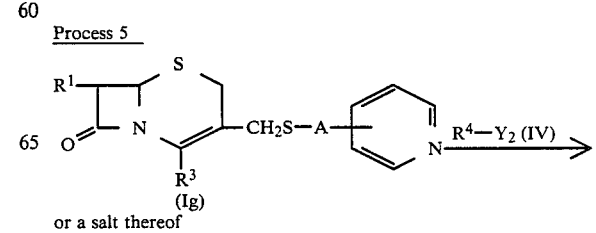

or a salt thereof

Process 6

(Ih) or a salt thereof $$R^1\text{-}\beta\text{-lactam-CH}_2\text{S-A-R}^2 \xrightarrow{\text{Esterification}}$$
(Id) or a salt thereof $$R^1\text{-}\beta\text{-lactam-CH}_2\text{S-A-R}^2, \text{COOR}$$
(Ii) or a salt thereof

Process 7

(Ij) or a salt thereof

Elimination of the amino protective group →

(Ia) or a salt thereof wherein
- $R^1$, $R^2$, $R^3$ and A are each as defined above,
- $R_a^1$ is acylamino,
- $R_a^3$ is protected carboxy,
- $Y_1$ is an acid residue,
- $R_b^1$ is acylamino having protected amino group,
- $R_c^1$ is acylamino having amino group,
- $R^4$ is lower alkyl,
- $Y_2$ is an acid residue,
- R is ester moiety of esterified carboxy represented by a group of the formula: —COOR, and
- $R_d^1$ is protected amino.

Among the starting compounds in the present invention, some of the compound (II) and the compound (III) are novel and can be prepared by the processes which are illustrated in the following schemes.

Process A (V) or its reactive derivative at the amino group or a salt thereof

+

(VI) or its reactive derivative at the carboxy group or a salt thereof

→

(IIa) or a salt thereof

Process B $$R^7\text{-C}\equiv\text{CH} + \text{HS-R}^8 \longrightarrow R^7\text{-CH=CH-S-R}^8$$

(VII) or a salt thereof  (VIII) or a salt thereof  (IX) or a salt thereof

Process C $$H_2N\text{-}\overset{O}{\overset{\|}{C}}\text{-A-S-R}^8 \longrightarrow \text{NC-A-S-R}^8$$

(IXa)  (Xa)

Process D $$R^2\text{-A-S-R}^8 \xrightarrow{\text{Elimination of the mercapto protective group}} R^2\text{-A-SH}$$

(X) or a salt thereof  (III) or a salt thereof

Process E $$R^2\text{-C}\equiv\text{CH} \longrightarrow R^2\text{-C}\equiv\text{C-SH}$$

(XI) or a salt thereof  (IIIa) or a salt thereof

Process F $$R^{11}\text{-S-A-pyridine} \xrightarrow{R^4\text{-Y}_2 \text{ (IV)}}$$

(XIII) or a salt thereof $$R^{11}\text{-S-A-pyridinium-R}^4 \cdot Y_2^{\ominus}$$

(IIIb) or a salt thereof

Process G

-continued

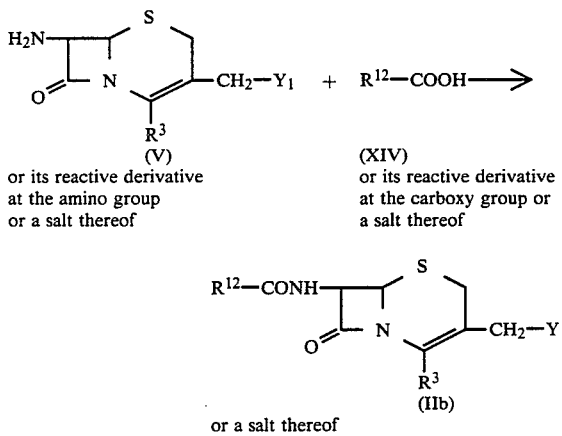

(V)
or its reactive derivative
at the amino group
or a salt thereof (XIV)
or its reactive derivative
at the carboxy group or
a salt thereof (IIb)
or a salt thereof wherein
$R^2$, $R^3$, $R^4$, A, $Y_1$ and $Y_2$ are each as defined above,
$R^5$ is amino or protected amino,
$R^6$ is lower alkenyl, lower alkynyl or isopropyl,
Z is N or CH,
$R^7$ is aryl which may have suitable substituent(s), a heterocyclic group which may have suitable substituent(s), cyano or carbamoyl,
$R^8$ is mercapto protective group,
$R^{11}$ is hydrogen or mercapto protective group, and
$R^{12}$ is cyano(lower)alkenylthio(lower)alkyl.

Suitable pharmaceutically acceptable salts of the object compound (I) are conventional non-toxic salts and may include a salt with a base or an acid addition salt such as a salt with an inorganic base, for example, an alkali metal salt (e.g. lithium salt, sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.) etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.); an intermolecular or intramolecular quaternary salt, and the like.

The said intermolecular quaternary salt can be formed in case that the heterocyclic group in $R^2$ in the compound (I) contains nitrogen atom(s) (e.g. pyridyl, etc.), and suitable intermolecular quaternary salt may include 1-lower alkylpyridinium lower alkylsulfate (e.g. 1-methylpyridinium methylsulfate, 1-ethylpyridinium ethylsulfate, etc.), 1-lower alkylpyridinium halide (e.g. 1-methylpyridinium iodide, etc.), 1-lower alkylpyridinium nitrate (e.g. 1-methylpyridinium nitrate, etc.) and the like. The said intramolecular quaternary salt can be formed in case that heterocyclic group in $R^2$ in the compound (I) contains nitrogen atom(s) (e.g. pyridyl etc.) and $R^3$ is carboxy, and suitable intramolecular quaternary salt may include 1-lower alkylpyridinium carboxylate (e.g. 1-methylpyridinium carboxylate, 1-ethylpyridinium carboxylate, 1-propylpyridinium carboxylate, 1-isopropylpyridinium carboxylate, 1-butylpyridinium carboxylate, etc.); and the like.

In the above and subsequent descriptions of the present specification, suitable examples and illustrations of the various definitions which the present invention include within the scope thereof are explained in detail as follows.

The term "lower" is intended to mean 1 to 6 carbon atom(s), unless otherwise indicated.

The term "higher" is intended to mean 7 to 20 carbon atoms, unless otherwise indicated.

Suitable "protected amino" may include acylamino; phosphonoamino; protected phosphonoamino; ar(-lower)alkylamino such as benzylamino, phenethylamino, tritylamino, ar(lower)alkylideneamino which may have hydroxy such as benzylideneamino, hydroxybenzylideneamino, phenethylideneamino; and the like.

Suitable "acyl" moiety in the terms "acylamino", "acylamino having protected amino group" and "acylamino having amino group" may include carbamoyl, aliphatic acyl group and acyl group containing an aromatic ring, which is referred to as aromatic acyl, or heterocyclic ring, which is referred to as heterocyclic acyl.

Suitable example of said acyl may be illustrated as follows:

Aliphatic acyl such as
lower or higher alkanoyl (e.g. formyl, acetyl, succinyl, hexanoyl, heptanoyl, valeryl, stearoyl, etc.);

lower or higher alkoxycarbonyl (e.g. methoxycarbonyl, ethoxycarbonyl, t-butoxycarbonyl, t-pentyloxycarbonyl, heptyloxycarbonyl, etc.);

lower or higher alkanesulfonyl (e.g. methanesulfonyl, ethanesulfonyl, etc.);

lower or higher alkoxysulfonyl (e.g. methoxysulfonyl, ethoxysulfonyl, etc.); or the like;

Aromatic acyl such as
aroyl (e.g. benzoyl, toluoyl, naphthoyl, etc.);
ar(lower)alkanoyl such as phenyl(lower)alkanoyl (e.g. phenylacetyl, phenylpropionyl, etc.);
aryloxycarbonyl (e.g. phenoxycarbonyl, naphthyloxycarbonyl, etc.);
aryloxy(lower)alkanoyl (e.g. phenoxyacetyl, phenoxypropionyl, etc.);
arylglyoxyloyl (e.g. phenylglyoxyloyl, naphthylglyoxyloyl, etc.); arenesulfonyl (e.g. benzenesulfonyl, p-toluenesulfonyl, etc.); or the like;

Heterocyclic acyl such as
heterocycliccarbonyl (e.g. thenoyl, furoyl, nicotinoyl, etc.);
heterocyclic(lower)alkanoyl (e.g. thienylacetyl, thiazolylacetyl, thiadiazolylacetyl, tetrazolylacetyl, etc.);
heterocyclicglyoxyloyl (e.g. thiazolylglyoxyloyl, thienylglyoxyloyl, etc.); or the like; in which suitable heterocyclic moiety in the terms "heterocycliccarbonyl", "heterocyclic(lower)alkanoyl" and "heterocyclicglyoxyloyl" as mentioned above means, in more detail, saturated or unsaturated, monocyclic or polycyclic heterocyclic group containing at least one hetero-atom such as an oxygen, sulfur, nitrogen atom and the like.

And, especially preferable heterocyclic group may be heterocyclic group such as
unsaturated 3 to 8-membered more preferably 5 or 6-membered heteromonocyclic group containing 1 to 4-nitrogen atom(s), for example, pyrrolyl, pyrrolinyl, imidazolyl, pyrazolyl, pyridyl and its N-oxide, dihydropyridyl, pyrimidyl, pyrazinyl, pyridazinyl, triazolyl (e.g. 4H-1,2,4-triazolyl, 1H-1,2,3-triazolyl, 2H-1,2,3- triazolyl, etc.), tetrazolyl (e.g. 1H-tetrazolyl, 2H-tetrazolyl, etc.), etc.;

saturated 3 to 8-membered (more preferably 5 or 6-membered)heteromonocyclic group containing 1 to 4 nitrogen atom(s), for example pyrrolidinyl, imidazolidinyl, piperidino, piperazinyl, etc.;

unsaturated condensed heterocyclic group containing 1 to 4 nitrogen atom(s), for example, indolyl, isoindolyl, indolizinyl, bennzimidazolyl, quinolyl, isoquinolyl, indazolyl, benzotriazolyl, etc.;

unsaturated 3 to 8-membered (more preferably 5 or 6-membered)heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.) etc.;

saturated 3 to 8-membered (more preferably 5 or 6-membered)heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered)heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered)heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered)heteromonocyclic group containing 1 to 2 sulfur atom(s), for example, thienyl, dihydrodithiinyl, dihydrodithiolyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered (more preferably 5 to 6-membered)heteromonocyclic group containing an oxygen atom, for example, furyl, etc.;

unsaturated 3 to 8-membered (more preferably 5 or 6-membered)heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example benzothienyl, benzodithiinyl, etc.;

unsaturated condensed heterocyclic group containing an oxygen atom and 1 to 2 sulfur atom(s), for example, benzoxathiinyl, etc. and the like.

As to the heterocyclic group as mentioned above, the following points are to be noted. That is, in case that the heterocyclic group is specifically thiazolyl or thiadiazolyl group having amino or protected amino as a substituent in its molecule, said thiazolyl or thiadiazolyl group include tautomeric isomers, which are caused by the specific behavior of the thiazole or thiadiazole ring. That is, for example, said amino or protected aminothiazolyl or thiadiazolyl group is represented by the formula:

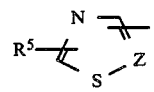

(wherein $R^5$ and Z are each as defined above), and in case that the group of the formula (A) takes the formula:

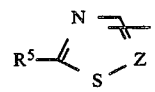

(wherein $R^5$ and Z are each as defined above), said group of the formula (A') can also be alternatively represented by its tautomeric formula:

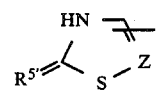

(wherein Z is as defined above and $R^{5'}$ is imino or protected imino).

That is, both of the said groups of the formulae (A') and (A'') are in the state of tautomeric equilibrium which can be represented by the following equilibrium:

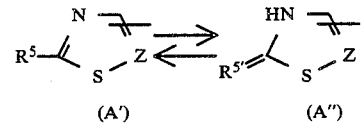

(wherein $R^5$, Z and $R^{5'}$ are each as defined above).

These types of tautomerism between 2-aminothiazole or 5-aminothiadiazole compounds and 2-iminothiazoline or 5-iminothiadiazoline compounds as stated above have been well known in the arts, and it is obvious to a person skilled in arts that both of the tautomeric isomers are equilibrated and lie in the reciprocally convertible state, and accordingly it is to be understood that such isomers are included within the same category of the compound per se. Accordingly, the both of the tautomeric forms are clearly included within the scope of the present invention. In the present specification, the object and starting compounds including the group of such tautomeric isomers are represented by using one of the expressions therefor, i.e. 2-amino(or protected amino)thiazolyl or 5-amino(or protected amino)thiadiazolyl and the formula:

"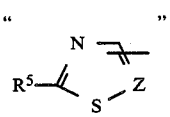"

only for the convenient sake.

The acyl moiety as stated above may have one to ten, same or different, suitable substituent(s) such as lower alkyl (e.g. methyl, ethyl, etc.); lower alkoxy (e.g. methoxy, ethoxy, propoxy, etc.); lower alkylthio (e.g. methylthio, ethylthio, etc.); lower alkylamino (e.g. methylamino, etc.); cyclo(lower)alkyl (e.g. cyclopentyl, cyclohexyl, etc.); cyclo(lower)alkenyl (e.g. cyclohexenyl, cyclohexadienyl, etc.); halogen; amino; protected amino; hydroxy; protected hydroxy; cyano; nitro; carboxy; protected carboxy; sulfo; sulfamoyl; imino; oxo; amino(lower)alkyl (e.g. aminomethyl, aminoethyl, etc.); carbamoyloxy; cyano(lower)alkenylthio (e.g. cyanovinylthio, etc.); a group of the formula: =N—OR⁹, wherein R⁹ is hydrogen or an organic group which may have suitable substituent(s), or the like.

In this connection, when the acyl moiety has a group of the formula: =N—OR⁹, wherein R⁹ is as defined above, as substituent(s), there are geometrical isomers (syn and anti isomers) due to the presence of double bond. And, for example, the syn isomer means one geometrical isomer having the group of the formula:

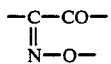

and the corresponding anti isomer means the other geometrical isomer having the group of the formula:

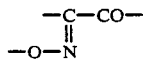

Suitable "aryl" in the term "aryl which may have suitable substituent(s)" may include phenyl, tolyl, xylyl, cumenyl, naphthyl and the like.

Suitable "substituent" in the term "aryl which may have suitable substituent(s)" may include hydroxy, halogen (e.g. fluorine, chlorine, bromine or iodine) and the like.

Suitable "heterocyclic group" in the term "a heterocyclic group which may have suitable substituent(s)" can be referred to the ones as mentioned above.

Suitable "substituent" in the term "a heterocyclic group which may have suitable substituent(s)" may include lower alkyl (e.g. methyl, ethyl, propyl, isopropyl, butyl, isobutyl, t-butyl, pentyl, hexyl, etc.) and the like.

Suitable "tri(lower)alkylsilyl" may include trimethylsilyl, triethylsilyl, tributylsilyl and the like.

Suitable "protected carboxy" may include esterified carboxy wherein "esterified carboxy" can be referred to the ones as mentioned below.

Suitable example of the ester moiety of an esterified carboxy may be the ones such as lower alkyl ester (e.g. methyl ester, ethyl ester, propyl ester, isopropyl ester, butyl ester, isobutyl ester, tert-butyl ester, pentyl ester, hexyl ester, 1-cyclopropylethyl ester, etc.) which may have at least one suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1(or 2)-acetoxyethyl ester, 1(or 2 or 3)-acetoxypropyl ester, 1(or 2 or 3 or 4)-acetoxybutyl ester, 1(or 2)-propionyloxyethyl ester, 1(or 2 or 3)-propionyloxypropyl ester, 1(or 2)-butyryloxyethyl ester, 1(or 2)-isobutyryloxyethyl ester, 1(or 2)-pivaloyloxyethyl ester, 1(or 2)-hexanoyloxyethyl ester, isobutyryloxymethyl ester, 2-ethybutyryloxymethyl ester, 3,3-dimethylbutyryloxymethyl ester, 1(or 2)-pentanoyloxyethyl ester, etc.], lower alkanesulfonyl(lower)alkyl ester (e.g. 2-mesylethyl ester, etc.), mono(or di or tri)-halo(lower)alkyl ester (e.g. 2-iodoethyl ester, 2,2,2-trichloroethyl ester, etc.), lower alkoxycarbonyloxy(lower)alkyl ester (e.g. methoxycarbonyloxymethyl ester, ethoxycarbonyloxymethyl ester, 2-methoxycarbonyloxyethyl ester, 1-ethoxycarbonyloxyethyl ester, 1-isopropoxycarbonyloxyethyl ester, etc.), phthalidylidene(lower)alkyl ester, or (5-lower alkyl 2-oxo-1,3-dioxol-4-yl)(lower)alkyl ester [e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.];

lower alkenyl ester (e.g. vinyl ester, allyl ester, etc.);

lower alkynyl ester (e.g. ethynyl ester, propynyl ester, etc.);

ar(lower)alkyl ester which may have at least one suitable substituent(s) such as mono(or di or tri)phenyl(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.);

aryl ester which may have at least one suitable substituent(s) (e.g. phenyl ester, 4-chlorophenyl ester, tolyl ester, tert-butylphenyl ester, xylyl ester, mesityl ester, cumenyl ester, etc.); phthalidyl ester; and the like.

Suitable example of ester moiety of esterified carboxy represented by a group of the formula: —COOR can be referred to the ones as exemplified above.

Suitable "acid residue" may include acyloxy, nitroxy, halogen (e.g. fluorine, chlorine, bromine or iodine) and the like, wherein acyl moiety in the term "acyloxy" can be referred to the ones as exemplified above.

Suitable "protected amino moiety" in the term "acylamino having protected amino group" can be referred to the ones as mentioned above.

Suitable "lower alkyl" may include methyl, ethyl, propyl, isopropyl, butyl, isobutyl, t-butyl, pentyl, hexyl and the like.

Suitable "lower alkenyl" may include vinyl, allyl, 1-propenyl, 1 or 2 or 3-butenyl, 1 or 2 or 3 or 4-pentenyl, 1 or 2 or 3 or 4 or 5-hexenyl, and the like.

Suitable "lower alkynyl" may include ethynyl, 1 or 2-propynyl, 1 or 2 or 3-butynyl, 1 or 2 or 3 or 4-pentynyl, 1 or 2 or 3 or 4 or 5-hexynyl, and the like.

Suitable "organic group which may have suitable substituent(s)" may include lower alkyl (e.g. methyl, ethyl, propyl, isopropyl, butyl, isobutyl, t-butyl, pentyl, hexyl, etc.), lower alkenyl as mentioned above, lower alkynyl as mentioned above, cyclo(lower)alkyl (e.g. cyclopropyl, cyclohexyl, etc.), ar(lower)alkyl such as phenyl(lower)alkyl (e.g. benzyl, phenethyl, etc.), carboxy(lower)alkyl (e.g. carboxymethyl, 1-carboxyethyl, carboxypropyl, etc.), protected carboxy(lower)alkyl (e.g. esterified carboxy(lower)alkyl, etc.), hydroxy(lower)alkyl (e.g. hydroxymethyl, hydroxyethyl, etc.), carboxy(lower)alkenyl (e.g. carboxyvinyl, carboxyallyl, carboxy-2-butenyl, etc.), protected carboxy(lower)alkenyl, cyclo(lower)alkenyl (e.g. cyclobutenyl, cyclopentenyl, cyclohexenyl, etc.), saturated 4 to 8-membered heteromonocyclic group containing one sulfur atom (e.g. thietanyl, thiolanyl, thianyl, thiepanyl, thiocanyl, etc.), and the like.

Suitable "cyano(lower)alkenylthio(lower)alkyl" may include cyanovinylthiomethyl, cyanovinylthioethyl, cyanovinylthiopropyl and the like.

Suitable "mercapto protective group" may include a conventional protective group such as lower alkyl as mentioned above; mono(or di or tri)phenyl(lower)alkyl (e.g. benzyl, phenethyl, phenylpropyl, trityl, etc.); acyl, for example, lower alkanoyl (e.g. formyl, acetyl, etc.) and the like.

Preferred embodiments of the object compound (I) are as follows.

Preferred embodiment of R¹ is amino, aryl(lower)alkanoylamino [more preferably phenyl(lower)alkanoylamino], protected aminothiazolyl(lower)alkanoylamino having a lower alkoxyimino group [more preferably acylaminothiazolyl(lower)alkanoylamino having a lower alkoxyimino group, most preferably lower alkanoylaminothiazolyl(lower)alkanoylamino having a lower alkoxyimino group or mono(or di or tri)halo(lower)alkanoylaminothiazolyl(lower)alkanoylamino having a lower alkoxyimino group], aminothiazolyl(lower)alkanoylamino having a lower alkoxyimino group, protected aminothiazolyl(lower)alkanoylamino having a lower alkynyloxyimino group [more preferably acylaminothiazolyl(lower)alkanoylamino having a lower alkynyloxyimino group, most preferably lower alkanoylaminothiazolyl(lower)alkanoylamino having a lower alkynyloxyimino group], aminothiazolyl(lower)alkanoylamino having a lower alkynyloxyimino group, protected aminothiazolyl(lower)alkanoylamino having a lower alkenyloxyimino group [more preferably acylaminothiazolyl(lower)alkanoylamino having a lower alkenyloxyimino group, most preferably lower alkanoylaminothiazolyl(lower)alkanoylamino having a lower alkenyloxyimino group], aminothiazolyl(lower)alkanoylamino having a lower alkenyloxyimino group, protected aminothiazolyl(lower)alkanoylamino having a protected carboxy(lower)alkoxyimino group [more preferably acylaminothiazolyl(lower)alkanoylamino having an esterified carboxy(lower)alkoxyimino group, most preferably mono(or di or tri)halo(lower)alkanoylaminothiazolyl(lower)alkanoylamino having a nitro substituted ar(lower)alkoxycarbonyl(lower)alkoxyimino group], protected aminothiazolyl(lower)alkanoylamino having a carboxy(lower)alkoxyimino group [more preferably acylaminothiazolyl(lower)alkanoylamino having a carboxy(lower)alkoxyimino group, most preferably mono(or di or tri)halo(lower)alkanoylaminothiazolyl(lower)alkanoylamino having a carboxy(lower)alkoxyimino group], aminothiazolyl(lower)alkanoylamino having a carboxy(lower)alkoxyimino group, protected aminothiazolyl(lower)alkanoylamino having a cyclo(lower)alkenyloxyimino group [more preferably acylaminothiazolyl(lower)alkanoylamino having a cyclo(lower)alkenyloxyimino group, most preferably lower alkanoylaminothiazolyl(lower)alkanoylamino having a cyclo(lower)alkenyloxyimino group], aminothiazolyl(lower)alkanoylamino having a cyclo(lower)alkenyloxyimino group, protected aminothiazolyl(lower)alkanoylamino having a thietanyloxyimino group [more preferably acylaminothiazolyl(lower)alkanoylamino having a thietanyloxyimino group, most preferably lower alkanoylaminothiazolyl(lower)alkanoylamino having a thietanyloxyimino group], aminothiazolyl(lower)alkanoylamino having a thietanyloxyimino group, aminothiadiazolyl(lower)alkanoylamino having a lower alkoxyimino group, aminothiadiazolyl(lower)alkanoylamino having a lower alkenyloxyimino group, cyano(lower)alkenylthio(lower)alkanoylamino or benzylideneamino which may have hydroxy;

R² is cyano, aryl (more preferably phenyl), pyridyl, lower alkylpyridyl, hydrogen or tri(lower)alkylsilyl;

A is —CH=CH— or —C≡C—; and

R³ is carboxy or protected carboxy (more preferably esterified carboxy, most preferably mono(or di or tri)phenyl(lower)alkoxycarbonyl, lower alkanoyloxy(lower)alkoxycarbonyl or 4-nitrophenyl(lower)alkoxycarbonyl).

Suitable intramolecular or intermolecular quaternary salt of the object compound (I) may include mono(or di or tri)phenyl(lower)alkyl 7-[2-(5-amino-1,2,4-thiadiazol-3-yl)-2-lower alkoxyiminoacetamido]-3-[2-(1-lower alkyl-3-pyridinio)vinylthiomethyl]-3-cephem-4-carboxylate halide, mono(or di or tri)phenyl(lower)alkyl 7-[2-(2-lower alkanoylaminothiazol-4-yl)-2-lower alkoxyiminoacetamido]-3-[2-(1-lower alkyl-3-pyridinio)vinylthiomethyl]-3-cephem-4-carboxylate nitrate, 7-[2-(5-amino-1,2,4-thiadiazol-3-yl)-2-(lower alkoxyimino)acetamido]-3-[2-(1-lower alkyl-3-pyridinio)-vinylthiomethyl]-3-cephem-4-carboxylate, 7-[2-(2-aminothiazol-4-yl)-2-lower alkoxyiminoacetamido]-3-[2-(1-lower alkyl-3-pyridinio)vinylthiomethyl]-3-cephem-4-carboxylate, and the like.

The processes for preparing the object compounds of the present invention are explained in detail in the following.

PROCESS 1

The object compound (Ib) or a salt thereof can be prepared by subjecting the compound (Ia) or its reactive derivative at the amino group or a salt thereof to acylation reaction.

Suitable reactive derivative at the amino group of the compound (Ia) may include Schiff's base type imino or its tautomeric enamine type isomer formed by the reaction of the compound (Ia) with a carbonyl compound such as aldehyde, ketone or the like; a silyl derivative formed by the reaction of the compound (Ia) with a silyl compound such as bis(trimethylsilyl)acetamide, mono(trimethylsilyl)acetamide, bis(trimethylsilyl)urea or the like; a derivative formed by reaction of the compound (Ia) with phosphorus trichloride or phosgene, and the like.

Suitable acylating agent to be used in the present acylation reaction may include conventional one and can be shown by the formula:

$$R^{10}-OH \qquad (XII)$$

(wherein R¹⁰ is acyl) or its reactive derivative or a salt thereof.

Suitable salts of the compounds (Ia) and (Ib) can be referred to the ones as exemplified for the compound (I).

Suitable salt of the compound (XII) may include a salt with a base or an acid addition salt such as a salt with an inorganic base, for example, an alkali metal salt (e.g. sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.) etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.); and the like.

Suitable reactive derivative of the compound (XII) may include an acid halide, an acid anhydride, an activated amide, an activated ester, and the like. The suitable example may be an acid chloride; an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid etc.), dialkylphosphorous acid, lower alkanesulfonic acid (e.g. methanesulfonic acid, ethanesulfonic acid, etc.), sulforous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl[$(CH_3)_2N^+=CH-$]ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (XII) to be used.

The reaction is usually carried out in a conventional solvent such as water, methanol, ethanol, acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

When the compound (XII) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride, thionyl chloride; oxalyl chloride; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, or the like. The reaction temperature is not critical, and the reaction is usually carried out under cooling or at ambient temperature.

PROCESS 2

The object compound (Id) or a salt thereof can be prepared by subjecting the compound (Ic) or a salt thereof to elimination reaction of the carboxy protective group.

Suitable salts of the compounds (Ic) and (Id) can be referred to the salt exemplified for the compound (I).

The present reaction is carried out in accordance with a conventional method such as hydrolysis, reduction or the like.

In case that the protective group is an ester, the protective group can be eliminated by hydrolysis. Hydrolysis is preferably carried out in the presence of a base or an acid including Lewis acid. Suitable base may include an inorganic base and an organic base such as an alkali metal (e.g. sodium, potassium, cesium, etc.), an alkaline earth metal (e.g. magnesium, calcium, etc.), the hydroxide or carbonate or bicarbonate thereof, trialkylamine (e.g. trimethylamine, triethylamine, etc.), picoline, 1,5-diazabicyclo[4,3,0]none-5-ene, 1,4-diazabicyclo[2,2,2]octane, 1,8-diazabicyclo[5,4,0]undecene-7, or the like. Suitable acid may include an organic acid (e.g. formic acid, acetic acid, propionic acid, trichloroacetic acid, trifluoroacetic acid, etc.) and an inorganic acid (e.g. hydrochloric acid, hydrobromic acid, sulfuric acid, etc.). The elimination using Lewis acid such as trihaloacetic acid (e.g. trichloroacetic acid, trifluoroacetic acid, etc.) or the like is preferably carried out in the presence of cation trapping agents (e.g. anisole, thioanisole, phenol, etc.).

Reduction can be applied preferably for elimination of the protective group such as 4-nitrobenzyl, 2-iodoethyl, 2,2,2-trichloroethyl, or the like. The reduction method applicable for the elimination reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, etc.); and conventional catalytic reduction in the presence of a conventional metallic catalyst (e.g. palladium-carbon, etc.).

The reaction is usually carried out in a solvent such as water, an alcohol (e.g. methanol, ethanol, etc.), tetrahydrofuran, methylene chloride, a mixture thereof or any other solvent which does not adversely influence to the reaction. A liquid base or acid can be also used as the solvent. The reaction temperature is not critical and the reaction is usually carried out under cooling to warming.

The present invention includes, within the scope of the invention, a case that the compound (Id) in a form of intermolecular quaternary salt is transformed into its intramolecular quaternary salt by a conventional method, e.g., by treating the compound (Id) with base.

The present invention also includes, within the scope of the invention, a case that when the compound (Ic) possesses one or more protected carboxy groups in the acylamino group at 7 position on cephem ring, said protected carboxy group is changed into corresponding free carboxy group during the reaction.

PROCESS 3

The object compound (I) or a salt thereof can be prepared by reacting a compound (II) or a salt thereof with a compound (III) or a salt thereof.

Suitable salt of the compound (II) can be referred to the ones as exemplified for the compound (XII).

Suitable salt of the compound (III) may include the ones as exemplified for the compound (I) and silver salt.

The reaction may be carried out in the presence of sodium iodide, sodium thiocyanate and the like.

The reaction is usually carried out in a solvent such as water, acetone, chloroform, nitrobenzene, n-hexane, methylene chloride, ethylene chloride, acetonitrile, N,N-dimethylformamide, methanol, ethanol, ether, tetrahydrofuran or any other conventional solvents which do not adversely influence the reaction. When the compound (II), wherein $R^1$ is amino, is used in the presence reaction, the said compound (II) is, in advance, preferably treated with the silyl compound such as bis(trimethylsilyl)acetamide, mono(trimethylsilyl)acetamide, bis(trimethylsilyl)urea or the like.

When the compound (III) is used in free form in the reaction, the reaction is preferably carried out in the presence of a base, for example, an organic or an inorganic base such as alkali metal hydroxide, alkali metal carbonate, alkali metal bicarbonate, alkali metal alkoxide (e.g. sodium methoxide, sodium ethoxide, etc.), trialkylamine, pyridine or the like, and preferably carried out around neutral conditions. The reaction temperature is not critical and the reaction is usually carried out under cooling, at ambient temperature or under warming.

PROCESS 4

The object compound (If) or a salt thereof can be prepared by subjecting the compound (Ie) or a salt thereof to elimination reaction of amino protective group.

Suitable salts of the compounds (Ie) and (If) can be referred to the ones as exemplified for the compound (I).

The present elimination reaction is carried out in accordance with a conventional method such as hydrolysis; reduction; a method by reacting the compound (Ie) wherein the protective group is acyl group with iminohalogenating agent and then with iminoetherifying agent, and, if necessary, subjecting the resulting compound to hydrolysis; or the like. The hydrolysis may include a method using an acid or base or hydrazine and the like. These methods may be selected depending on the kind of the protective groups to be eliminated.

Among these methods, hydrolysis using an acid is one of the common and preferable method for eliminating the protective group such as substituted or unsubstituted alkoxycarbonyl (e.g. t-pentyloxycarbonyl, t-butoxycarbonyl, etc.), alkanoyl (e.g. formyl, etc.), cycloalkoxycarbonyl, substituted or unsubstituted aralkoxycarbonyl (e.g. benzyloxycarbonyl, substituted benzyloxycarbonyl, etc.), ar(lower)alkyl (e.g. benzyl, trityl, etc.), substituted or unsubstituted ar(lower)alkylidene (e.g. benzylidene, hydroxybenzylidene, etc.) or the like.

Suitable acid may include an organic or an inorganic acid, for example, formic acid, trifluoroacetic acid, benzenesulfonic acid, p-toluenesulfonic acid, hydrochloric acid and the like, and preferable acid is, for example, formic acid, trifluoroacetic acid, hydrochloric acid, etc. The acid suitable for the reaction can be selected according to the kind of protective group to be eliminated. When the elimination reaction is conducted with the acid, it can be carried out in the presence or absence of a solvent. Suitable solvent may include a conventional organic solvent (e.g. methanol, ethanol, tetrahydrofuran, etc.), water or a mixture thereof. When trifluoroacetic acid is used, the elimination reaction may preferably be carried out in the presence of anisole.

The hydrolysis using hydrazine is commonly applied for eliminating the protective group, for example, succinyl or phthaloyl.

The hydrolysis with a base is preferably applied for eliminating acyl group, for example, haloalkanoyl (e.g. dichloroacetyl, trifluoroacetyl, etc.), etc. Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate, (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4,3,0]non-5-ene, 1,4-diazabicyclo[2,2,2]octane, 1,8-diazabicyclo[5,4,0]undecene-7 or the like. The hydrolysis using a base is often carried out in water, a conventional organic solvent or a mixture thereof.

Among the protective group, the acyl group can be generally eliminated by hydrolysis as mentioned above or by the other conventional hydrolysis. In case that the acyl group is halogen substituted-alkoxycarbonyl or 8-quinolyloxycarbonyl, they are eliminated by treating with a heavy metal such as copper, zinc or the like.

The reductive elimination is generally applied for eliminating the protective group, for example, haloalkoxycarbonyl (e.g. trichloroethoxycarbonyl, etc.), substituted or unsubstituted aralkoxycarbonyl (e.g. benzyloxycarbonyl, substituted benzyloxycarbonyl, etc.), 2-pyridylmethoxycarbonyl, etc. Suitable reduction may include, for example, reduction with an alkali metal borohydride (e.g. sodium borohydride, etc.) and the like.

The reaction temperature is not critical and may be suitably selected in accordance with the kind of the protective group of the amino group and the elimination method as mentioned above, and the present reaction is preferably carried out under a mild condition such as under cooling, at ambient temperature or slightly elevated temperature.

PROCESS 5

The object compound (Ih) or a salt thereof can be prepared by reacting the compound (Ig) or a salt thereof with the compound (IV).

Suitable salt of the compound (Ig) can be referred to the ones as exemplified for the compound (XII).

Suitable salt of the compound (Ih) can be referred to the ones as exemplified for the compound (I).

The reaction is usually carried out in a solvent such as water, acetone, tetrahydrofuran, ethanol, ether, N,N-dimethylformamide or any other solvent which does not adversely influence the reaction.

The reaction temperature is not critical and the reaction is usually carried out under cooling to heating.

The present invention includes, within the scope of the invention, a case that the compound (Ih) wherein $R^3$ is carboxy is transformed into its intramolecular quaternary salt by a conventional method, e.g., by treating the compound (Ih) with base.

PROCESS 6

The object compound (Ii) or a salt thereof can be prepared by subjecting the compound (Id) or a salt thereof to esterification reaction.

Suitable salt of the compound (Ii) can be referred to the ones exemplified for the compound (I).

The present reaction may be carried out by reacting the compound (Id) or a salt thereof with esterifying agent.

Suitable esterifying agent may be a compound of the formula: X—R wherein

R is as defined above, and

X is hydroxy or its reactive derivative.

Suitable reactive derivative of hydroxy for X may include an acid residue such as aforesaid halogen or the like.

The present reaction is usually carried out in a solvent such as N,N-dimethylformamide, pyridine, hexamethylphosphoric triamide, dimethylsulfoxide or any other solvent which does not adversely affect the reaction.

In case that the compound (Id) is used in a form of free acid, the reaction is preferably carried out in the presence of a base as mentioned in Process 2.

The reaction temperature is not critical and the reaction is preferably carried out under cooling, at ambient temperature or under warming.

PROCESS 7

The object compound (Ia) or a salt thereof can be prepared by subjecting the compound (Ij) or a salt thereof to elimination reaction of amino protective group.

Suitable salt of the compound (Ij) can be referred to the ones as exemplified for the compound (I).

This reaction can be carried out in a similar manner to that of aforementioned Process 4.

Processes for the preparation of the compound (III) and some of the compound (II) are explained as follows.

PROCESS A

The compound (IIa) or a salt thereof can be prepared by reacting a compound (V) or its reactive derivative at the amino group or a salt thereof with a compound (VI) or its reactive derivative at the carboxy group or a salt thereof.

Suitable salt of the compounds (V), (VI) and (IIa) can be referred to the ones as exemplified for the compound (XII).

Suitable reactive derivative at the amino group of the compound (V) and reactive derivative at the carboxy group of the compound (VI) can be referred to the ones as exemplified for the compounds (Ia) and (XII), respectively.

This reaction can be carried out in a similar manner to that of aforementioned Process 1.

PROCESS B

The compound (IX) or a salt thereof can be prepared by reacting the compound (VII) or a salt thereof with the compound (VIII) or a salt thereof.

When the compound (VIII) is used in free form in the reaction, the reaction is preferably carried out in the presence of a base such as alkali metal alkoxide (e.g. sodium methoxide, potassium methoxide, sodium ethoxide, potassium ethoxide, potassium t-butoxide, etc.), alkali metal hydroxide (e.g. sodium hydroxide, potassium hydroxide, etc.) or the like.

The reaction is usually carried out in a solvent such as water, tetrahydrofuran or any other solvent which does not adversely influence the reaction.

The reaction temperature is not critical and the reaction is usually carried out under cooling to warming.

PROCESS C

The compound (Xa) can be prepared by subjecting the compound (IXa) to dehydration.

The dehydrating agent to be used in this dehydration reaction may include phosphoryl chloride, thionyl chloride, phosphorus pentoxide, phosphorus pentachloride, phosphorus pentabromide and the like.

The present reaction is usually carried out in a solvent such as tetrahydrofuran, N,N-dimethylformamide or any other solvent which does not adversely affect the reaction.

The reaction temperature is not critical and the reaction is usually carried out under cooling, at ambient temperature or under warming.

PROCESS D

The compound (III) or a salt thereof can be prepared by subjecting the compound (X) or a salt thereof to the elimination reaction of the mercaptoprotective group.

The present elimination reaction may be carried out in accordance with a conventional method such as hydrolysis using an organic or inorganic acid (e.g. acetic acid, hydrobromic acid, etc.), hydrolysis using an organic or inorganic base such as alkali metal alkoxide (e.g. sodium methoxide, sodium ethoxide, etc.), alcoholysis using nitrate (e.g. silver nitrate, etc.) or the like.

The present reaction is usually carried out in a solvent such as water, alcohol (e.g. methanol, ethanol, etc.), tetrahydrofuran or a mixture thereof, or any other solvents which do not adversely affect the reaction.

The reaction temperature is not critical and the reaction is preferably carried out under cooling to heating.

PROCESS E

The compound (IIIa) or a salt thereof can be prepared by reacting the compound (XI) or a salt thereof with metalating agent and then with sulfur.

Suitable metalating agent may include alkyl alkali metal such as n-butyllithium or the like. The present reaction is usually carried out in a solvent such as tetrahydrofuran, n-hexane, hexamethylphosphoric triamide or any other solvent which does not adversely affect the reaction. The reaction temperature is not critical and the reaction is usually carried out under cooling or at ambient temperature.

PROCESS F

The compound (IIIb) or a salt thereof can be prepared by reacting the compound (XIII) or a salt thereof with the compound (IV).

This reaction can be carried out in a similar manner to that of aforementioned Process 5.

PROCESS G

The compound (IIb) or a salt thereof can be prepared by reacting a compound (V) or its reactive derivative at the amino group or a salt thereof with a compound (XIV) or its reactive derivative at the carboxy group or a salt thereof.

Suitable reactive derivative at the carboxy group of the compound (XIV) can be referred to the ones as exemplified for the compound (XII).

This reaction can be carried out in a similar manner to that of aforementioned Process 1.

The object compounds (I) and pharmaceutically acceptable salts thereof of the present invention are novel compounds which exhibit high antibacterial activity and inhibit the growth of a wide variety of pathogenic microorganisms including Gram-positive and Gram-negative bacteria and are useful as antimicrobial agents. For therapeutic purpose, the compounds according to the present invention can be used in the form of conventional pharmaceutical preparation which contain said compounds, as an active ingredient, in admixture with a pharmaceutically acceptable carrier such as an organic or an inorganic solid or liquid excipient suitable for oral, parenteral or external administration. The pharmaceutical preparations may be in solid form such as capsule, tablet, dragee, ointment or suppository, or in liquid form such as solution, suspension, or emulsion. If desired, there may be included in the above preparations auxiliary substances, stabilizing agents, wetting or emulsifying agents, buffers and other commonly used additives such as lactose, fumaric acid, citric acid, tartaric acid, stearic acid, maleic acid, succinic acid, malic acid, magnesium stearate, terra alba, sucrose, corn starch, talc, gelatin, agar, pectin, peanut oil, olive oil, cacao butter, ethylene glycol, and the like.

While the dosage of the compound will vary depending upon the age and condition of the patient, an average single dose of about 10 mg, 50 mg, 100 mg, 250 mg, 500 mg, and 1000 mg of the compounds according to the present invention may be effective for treating infectious diseases caused by pathogenic bacteria. In general, amount between 1 mg/body and about 6,000 mg/body or even more may be administered per day.

In order to illustrate the usefulness of the object compound, anti-microbial activities of a representative compound of the present invention are shown below.

Minimal inhibitory concentration (A) Test Method

In vitro antibacterial activity was determined by the two-fold agar-plate dilution method as described below.

One loopful of an overnight culture of each test strain in trypticase-soy broth ($10^8$ viable cells per ml) was streaked on heart infusion agar (HI-agar) containing graded concentrations of representative test compounds, and the minimal inhibitory concentration (MIC) was expressed in terms of $\mu$g/ml after incubation at 37° C. for 20 hours.

(b) Test Compound (1) 7-[2-(2-Aminothiazol-4-yl)-2-allyloxyiminoacetamido]-3-[(Z)-2-(3-pyridyl)vinylthiomethyl]-3-cephem-4-carboxylic acid (syn isomer).

(2) 7-[2-(2-Aminothiazol-4-yl)-2-(2-cyclopenten-1-yl)oxyiminoacetamido]-3-[(Z)-2-(3-pyridyl)vinylthiomethyl]-3-cephem-4-carboxylic acid (syn isomer).

(C) Test Result

| | M.I.C. ($\mu$g/ml) | |
| --- | --- | --- |
| | Test compound | |
| Test strain | (1) | (2) |
| Escherichia coli 31 | 0.05 | 0.05 |

The following preparations and examples are given for the purpose of illustrating the present invention in more detail.

PREPARATION 1

To an ice-cooled solution of propiolamide (1 g) in tetrahydrofuran (10 ml) and water (10 ml) was added a mixture of triphenylmethanethiol (4.2 g), tetrahydrofuran (10 ml) and 1N aqueous solution (1 ml) of sodium hydroxide at 0°–5° C. The mixture was stirred for 30 minutes at 0°–10° C. To the reaction mixture was added water (40 ml) and the mixture was cooled. The resultant precipitates were collected by filtration to give (Z)-3-tritylthioacrylamide (4.2 g).

IR (Nujol): 3380, 3180, 1640, 1570 cm$^{-1}$

PREPARATION 2

To an ice-cooled suspension of (Z)-3-tritylthioacrylamide (3.9 g) in N,N-dimethylformamide (40 ml) was added phosphorus pentachloride (3.65 g) and the mixture was stirred for 30 minutes at 20°. The reaction mixture was poured into ice-water and extracted with ethyl acetate. The separated organic layer was washed with brine, dried over magnesium sulfate and evaporated in vacuo to give (Z)-3-tritylthioacrylonitrile (2.85 g).

IR (Nujol): 2200 cm$^{-1}$

NMR (DMSO-d$_6$, $\delta$): 5.65 (1H, d, J=10 Hz), 6.88 (1H, d, J=10 Hz), 7–7.67 (15H, m)

PREPARATION 3

To a solution of triphenylmethanethiol (1.41 g) and 3-ethynylpyridine (0.5 g) in anhydrous tetrahydrofuran (10 ml) was added potassium t-butoxide (571 mg) at ambient temperature. The mixture was refluxed for 2 hours. After the reaction mixture was cooled to ambient temperature, the reaction mixture was poured into ice-water. The mixture was extracted with ethyl acetate. The extract was washed with a saturated aqueous solution of sodium chloride, dried over magnesium sulfate and concentrated in vacuo to give a crystal. The crystal was washed with ethanol and dried to give 3-[(Z)-2-(tritylthio)vinyl]pyridine (1.11 g).

Mp: 140°–141° C.

IR (Nujol): 1590, 1560, 1470, 1450, 1410 cm$^{-1}$

NMR (CDCl$_3$, $\delta$): 6.03 (1H, d, J=11 Hz), 6.27 (1H, d, J=11 Hz), 7.27 (15H, s), 7.13–7.23 (1H, m), 7.90 (1H, d, t, J=2, 8 Hz), 8.40 (1H, dd, J=2, 5 Hz), 8.63 (1H, d, J=2 Hz)

PREPARATION 4

The following compound was obtained according to a similar manner to that of Preparation 3.

2-[(Z)-2-(Tritylthio)vinyl]pyridine

IR (Nujol): 1595, 1580, 1545, 1490, 1440, 1430 cm$^{-1}$

NMR (CDCl$_3$, $\delta$): 6.30 (2H, s), 6.87–7.73 (18H, m), 8.63 (1H, dd, J=2 Hz, 5 Hz)

PREPARATION 5

To a solution of 3-[(Z)-2-(tritylthio)vinyl]pyridine (690 mg) in a mixture of tetrahydrofuran (3 ml), methanol (5 ml) and pyridine (0.147 ml) was dropwise added a solution of silver nitrate (371 mg) in methanol (20 ml) at ambient temperature. The reaction mixture was stirred at 40° C. in dark. The precipitate was collected, washed with methanol and dried over phosphorus pentoxide to give [(Z)-2-(3-pyridyl)vinylthio]silver (487 mg).

IR (Nujol): 1590, 1580, 1560, 1420 cm$^{-1}$

PREPARATION 6

The following compound was obtained according to a similar manner to that of Preparation 5.

[(Z)-2-cyanovinylthio]silver
IR (Nujol): 2200, 1530 cm$^{-1}$

PREPARATION 7

To a suspension of 2-[(Z)-2-(tritylthio)vinyl]pyridine (14.5 g) in a mixture of tetrahydrofuran (80 ml) and methanol (90 ml) was added a solution of silver nitrate (7.79 g) in a mixture of water (20 ml) and methanol at ambient temperature. The mixture was stirred at 60° C. for 6 hours. The precipitate was collected, washed with methanol and tetrahydrofuran in turn and dried to give [(Z and E)-2-(2-pyridyl)vinylthio]silver (10.54 g).

IR (Nujol): 1590 cm$^{-1}$

PREPARATION 8

Phosphorus oxychloride (7.0 ml) was added under ice-cooling to a solution of N,N-dimethylformamide (5.8 ml) in tetrahydrofuran (11 ml). The mixture was cooled until the precipitate appeared. Tetrahydrofuran (107 ml) was then added to this mixture, and the mixture was stirred for 20 minutes at 0° C. 2-(2-Formamidothiazol-4-yl)-2-allyloxyiminoacetic acid (syn isomer) (13.2 g) was added to the mixture. The resultant mixture was stirred at 0° C. to give an activated acid solution. On the other hand, to a suspension of benzhydryl 7-amino-3-chloromethyl-3-cephem-4-carboxylate monohydrochloride (20 g) in tetrahydrofuran (200 ml) was added bis(trimethylsilyl)urea (36.2 g) at ambient temperature. The mixture was stirred at 36°-38° C. for 40 minutes to give a clear solution. To this solution was added the activated acid solution obtained above at once at −20° C. The mixture was stirred at −20°~12° C. for 40 minutes. To this mixture was added a mixture of ethyl acetate (700 ml) and water. The separated organic layer was washed with an aqueous solution of sodium bicarbonate, dried over magnesium sulfate and concentrated to give a solid. The solid was recrystallized from diisopropyl ether to give benzhydryl 7-[2-(2-formamidothiazol-4-yl)-2-allyloxyiminoacetamido]-3-chloromethyl-3-cephem-4-carboxylate (syn isomer) (25.5 g).

IR (Nujol): 1775, 1715, 1690, 1660 cm$^{-1}$

NMR (DMSO-d$_6$, δ): 3.0, 3.35 (2H, ABq, J=14 Hz), 3.67 (2H, m), 4.63 (2H, d, J=6 Hz), 5.27 (1H, d, J=5 Hz), 5.6–6.3 (3H, m), 6.95 (1H, s), 7.17–7.76 (11H, m), 8.5 (1H, s), 9.73 (1H, d, J=8 Hz)

PREPARATION 9

The following compounds were obtained according to a similar manner to that of Preparation 8.

(1) Benzhydryl 7-[2-(5-amino-1,2,4-thiadiazol-3-yl)-2-allyloxyiminoacetamido]-3-chloromethyl-3-cephem-4-carboxylate (syn isomer)

IR (Nujol): 1760, 1705, 1660, 1600, 1500 cm$^{-1}$

NMR (DMSO-d$_6$, δ): 3.5–3.8 (2H, m), 4.43 (2H, s), 4.67 (2H, d, J=5 Hz), 5.0–5.6 (1H, m), 5.26 (1H, d, J=5 Hz), 5.7–6.3 (2H, m), 6.95 (1H, s), 7.17–7.67 (10H, broad s), 8.10 (2H, s), 9.63 (1H, d, J=8 Hz)

(2) Benzhydryl 7-[2-(2-formamidothiazol-4-yl)-2-(2-propynyloxyimino)acetamido]-3-chloromethyl-3-cephem-4-carboxylate (syn isomer)

IR (Nujol): 1780, 1720, 1670, 1540 cm$^{-1}$

NMR (DMSO-d$_6$, δ): 3.3–3.7 (3H, m), 4.37 (2H, broad s), 4.72 (2H, d, J=3 Hz), 5.23 (1H, d, J=6 Hz), 5.90 (1H, dd, J=6 Hz, 8 Hz), 6.90 (1H, s), 7.1–7.6 (11H, m), 8.45 (1H, s), 9.73 (1H, d, J=8 Hz)

(3) Benzhydryl 7-(2-phenylacetamido)-3-chloromethyl-3-cephem-4-carboxylate

IR (Nujol): 3300, 1775, 1720, 1655, 1530, 1240 cm$^{-1}$

NMR (DMSO-d$_6$, δ): 3.55 (2H, s), 3.67 (2H, s), 4.43 (2H, s), 5.18 (1H, d, J=5 Hz), 5.79 (1H, dd, J=5 Hz and 8 Hz), 6.97 (1H, s), 7.2–7.7 (10H, m), 9.13 (1H, d, J=8 Hz)

EXAMPLE 1

Phosphorus oxychloride (0.516 ml) was added under ice-cooling to a solution of N,N-dimethylformamide (405 mg) in tetrahydrofuran (0.8 ml). The mixture was cooled until a precipitate appeared. Tetrahydrofuran (15 ml) was added to the reaction mixture. The mixture was stirred for 20 minutes at 0° C.

2-(2-Formamidothiazol-4-yl)-2-methoxyiminoacetic acid (syn isomer) (1.06 g) was added to the mixture at 0° C. The mixture was stirred for 30 minutes at the same temperature to give an activated acid solution. On the other hand, to the suspension of benzhydryl 7-amino-3-[(Z)-2-(3-pyridyl)vinylthiomethyl]-3-cephem-4-carboxylate (2.38 g) in tetrahydrofuran (30 ml) was added bis(trimethylsilyl)urea (2.8 g) at ambient temperature. The mixture was stirred at 48° C. for 30 minutes to give a clear solution. The solution was cooled to −20° C. To this solution was added the activated acid solution obtained above at once at −20° C. The mixture was stirred at −20° C.~−12° C. for 40 minutes. To this mixture was added a mixture of ethyl acetate (150 ml) and water. The separated organic layer was washed with an aqueous solution of sodium bicarbonate, dried over magnesium sulfate and concentrated in vacuo to give a solid. The solid was recrystallized from ethyl acetate to give benzhydryl 7-[2-(2-formamidothiazol-4-yl)-2-methoxyiminoacetamido]-3-[(Z)-2-(3-pyridyl)vinylthiomethyl]-3-cephem-4-carboxylate (syn isomer) (1.26 g).

IR (Nujol): 3250, 1775, 1715, 1690, 1660 cm$^{-1}$

NMR (DMSO-d$_6$, δ): 3.67 (2H, broad s), 3.90 (3H, s), 3.73–4.27 (2H, m), 5.30 (1H, d, J=5 Hz), 6.93 (1H, dd, J=5, 8 Hz), 6.37 (1H, d, J=11 Hz), 6.63 (1H, d, J=11 Hz), 6.97 (1H, s), 7.20–7.67 (12H, m), 7.70–7.97 (1H, m), 8.30–8.80 (2H, m), 8.53 (1H, s), 9.73 (1H, d, J=8 Hz), 12.6 (1H, s)

EXAMPLE 2

The following compounds were obtained according to a similar manner to that of Example 1.

(1) Benzhydryl 7-[2-(5-amino-1,2,4-thiadiazol-3-yl)-2-allyloxyiminoacetamido]-3-[(Z)-2-phenylvinylthiomethyl]-3-cephem-4-carboxylate (syn isomer)

IR (Nujol): 1770, 1720, 1670, 1620, 1520 cm$^{-1}$ (2) 7-[2-(5-Amino-1,2,4-thiadiazol-3-yl)-2-allyloxyiminoacetamido]-3-[(Z)-2-phenylvinylthiomethyl]-3-cephem-4-carboxylic acid (syn isomer)

mp: 153° C. (dec.)

IR (Nujol): 1765, 1670, 1620, 1520 cm$^{-1}$ (3) Benzhydryl 7-[2-(5-amino-1,2,4-thiadiazol-3-yl)-2-allyloxyiminoacetamido]-3-[(Z)-2-(2-pyridyl)vinylthiomethyl]-3-cephem-4-carboxylate (syn isomer)

IR (Nujol): 1770, 1715, 1670, 1610, 1590, 1520 cm$^{-1}$ (4) Benzhydryl 7-[2-(5-amino-1,2,4-thiadiazol-3-yl)-2-allyloxyiminoacetamido]-3-[(E)-2-(2-pyridyl)vinylthiomethyl]-3-cephem-4-carboxylate (syn isomer)

IR (Nujol): 1780, 1720, 1670, 1600, 1580, 1520 cm$^{-1}$ (5) 7-[2-(5-Amino-1,2,4-thiadiazol-3-yl)-2-allyloxyiminoacetamido]-3-[(Z)-2-(2-pyridyl)vinylthiomethyl]-3-cephem-4-carboxylic acid (syn isomer)

mp: 172° C. (dec.)

IR (Nujol): 1760, 1665, 1610, 1565, 1530 cm$^{-1}$ (6) 7-[2-(5-Amino-1,2,4-thiadiazol-3-yl)-2-allyloxyiminoacetamido]-3-[(E)-2-(2-pyridyl)vinylthiomethyl]-3-cephem-4-carboxylic acid monotrifluoroacetate (syn isomer)

NMR (DMSO-d$_6$, δ): 3.50–3.87 (2H, m), 3.87–4.30 (2H, m), 4.67 (2H, d, J=5 Hz), 5.07–5.53 (3H, m), 5.60–6.23 (2H, m), 6.67 (1H, d, J=15 Hz), 7.10–8.30 (5H, m), 8.00 (1H, d, J=15 Hz), 8.60 (1H, d, J=5 Hz), 9.57 (1H, d, J=9 Hz)

(7) Benzhydryl 7-[2-(2-formamidothiazol-4-yl)-2-methoxyiminoacetamido]-3-[(Z)-2-(2-pyridyl)vinylthiomethyl]-3-cephem-4-carboxylate (syn isomer)

IR (Nujol): 1770, 1710, 1690, 1660, 1580, 1540 cm$^{-1}$ (8) Benzhydryl 7-[2-(2-aminothiazol-4-yl)-2-methoxyiminoacetamido]-3-[(Z)-2-(2-pyridyl)vinylthiomethyl]-3-cephem-4-carboxylate (syn isomer)

IR (Nujol): 1775, 1715, 1665, 1610, 1590, 1520 cm$^{-1}$ (9) 7-[2-(2-Aminothiazol-4-yl)-2-methoxyiminoacetamido]-3-[(Z)-2-(2-pyridyl)vinylthiomethyl]-3-cephem-4-carboxylic acid (syn isomer)

mp: 153° C. (dec.)

IR (Nujol): 1770, 1660, 1570 cm$^{-1}$

(10) Benzhydryl 7-[2-(5-amino-1,2,4-thiadiazol-3-yl)-2-ethoxyiminoacetamido]-3-[(Z)-2-(2-pyridyl)vinylthiomethyl]-3-cephem-4-carboxylate (syn isomer)

NMR (DMSO-d$_6$, δ): 1.23 (3H, t, J=7 Hz), 3.67 (2H, broad s), 3.53–4.30 (2H, m), 4.17 (2H, q, J=7 Hz), 5.27 (1H, d, J=5 Hz), 5.90 (1H, dd, J=5 Hz, 8 Hz), 6.33 (1H, d, J=11 Hz), 6.70 (1H, d, J=11 Hz), 6.97 (1H, s), 7.07–7.90 (13H, m), 8.10 (2H, broad s), 8.47–8.67 (1H, m), 9.57 (1H, d, J=8 Hz)

(11) 7-[2-(5-Amino-1,2,4-thiadiazol-3-yl)-2-ethoxyiminoacetamido]-3-[(Z)-2-(2-pyridyl)vinylthiomethyl]-3-cephem-4-carboxylic acid (syn isomer)

mp: 175° C. (dec.)

IR (Nujol): 1765, 1670, 1610, 1570, 1520 cm$^{-1}$

(12) Benzhydryl 7-(2-phenylacetamido)-3-[(Z)-2-(3-pyridyl)vinylthiomethyl]-3-cephem-4-carboxylate IR (Nujol): 1770, 1705, 1640 cm$^{-1}$

(13) 7-(2-Phenylacetamido)-3-[(Z)-2-(3-pyridyl)vinylthiomethyl]-3-cephem-4-carboxylic acid monotrifluoroacetate IR (Nujol): 1775, 1660 cm$^{-1}$

(14) Benzhydryl 7-[2-(2-aminothiazol-4-yl)-2-methoxyiminoacetamido]-3-[(Z)-2-(3-pyridyl)vinylthiomethyl]-3-cephem-4-carboxylate (syn isomer)

IR (Nujol): 1770, 1710, 1670, 1610, 1530, 1300, 1240 cm$^{-1}$

(15) 7-[2-(2-Aminothiazol-4-yl)-2-methoxyiminoacetamido]-3-[(Z)-2-(3-pyridyl)vinylthiomethyl]-3-cephem-4-carboxylic acid (syn isomer)

mp: 170° C. (dec.)

IR (Nujol): 3300, 3200, 1760, 1650, 1620, 1590, 1540, 1530, 1180, 1040 cm$^{-1}$

(16) Benzhydryl 7-[2-(5-amino-1,2,4-thiadiazol-3-yl)-2-ethoxyiminoacetamido]-3-[(Z)-2-(3-pyridyl)vinylthiomethyl]-3-cephem-4-carboxylate (syn isomer)

IR (Nujol): 3300, 3150, 1780, 1720, 1675, 1610, 1530 cm$^{-1}$

(17) 7-[2-(5-Amino-1,2,4-thiadiazol-3-yl)-2-ethoxyiminoacetamido]-3-[(Z)-2-(3-pyridyl)vinylthiomethyl]-3-cephem-4-carboxylic acid (syn isomer)

mp: 156° C. (dec.)

IR (Nujol): 3300, 3200, 1770, 1670, 1620, 1580, 1530, 1250, 1230, 1180 cm$^{-1}$

(18) Benzhydryl 7-[2-(5-amino-1,2,4-thiadiazol-3-yl)-2-ethoxyiminoacetamido]-3-[(Z)-2-(1-methyl-3-pyridinio)vinylthiomethyl]-3-cephem-4-carboxylate iodide (syn isomer)

IR (Nujol): 1770, 1720, 1670, 1610, 1570, 1520 cm$^{-1}$

(19) 7-[2-(5-Amino-1,2,4-thiadiazol-3-yl)-2-ethoxyiminoacetamido]-3-[(Z)-2-(1-methyl-3-pyridinio)vinylthiomethyl]-3-cephem-4-carboxylate (syn isomer)

IR (Nujol): 1755, 1660, 1590 cm$^{-1}$

(20) Benzhydryl 7-[2-(5-amino-1,2,4-thiadiazol-3-yl)-2-ethoxyiminoacetamido]-3-[2-(3-pyridyl)ethynylthiomethyl]-3-cephem-4-carboxylate (syn isomer)

IR (Nujol): 2170, 1775, 1720, 1670, 1520 cm$^{-1}$

(21) 7-[2-(5-Amino-1,2,4-thiadiazol-3-yl)-2-ethoxyiminoacetamido]-3-[2-(3-pyridyl)ethynylthiomethyl]-3-cephem-4-carboxylic acid (syn isomer)

IR (Nujol): 3290, 3180, 2140, 1770, 1670, 1615, 1525 cm$^{-1}$

(22) Benzhydryl 7-[2-(2-formamidothiazol-4-yl)-2-allyloxyiminoacetamido]-3-[(Z)-2-(3-pyridyl)vinylthiomethyl]-3-cephem-4-carboxylate (syn isomer)

IR (Nujol): 3250, 1775, 1710, 1650 cm$^{-1}$

(23) Benzhydryl 7-[2-(2-aminothiazol-4-yl)-2-allyloxyiminoacetamido]-3-[(Z)-2-(3-pyridyl)vinylthiomethyl]-3-cephem-4-carboxylate (syn isomer)

IR (Nujol): 1770, 1720, 1670, 1610, 1530, 1300, 1240 cm$^{-1}$

(24) 7-[2-(2-Aminothiazol-4-yl)-2-allyloxyiminoacetamido]-3-[(Z)-2-(3-pyridyl)vinylthiomethyl]-3-cephem-4-carboxylic acid (syn isomer)

mp: 145° C. (dec.)

IR (Nujol): 1770, 1670, 1530 cm$^{-1}$

(25) Benzhydryl 7-[2-(2-formamidothiazol-4-yl)-2-(2-propynyloxyimino)acetamido]-3-[(Z)-2-(3-pyridyl)vinylthiomethyl]-3-cephem-4-carboxylate (syn isomer)

IR (Nujol): 1770, 1715, 1660, 1530 cm$^{-1}$

(26) Benzhydryl 7-[2-(2-aminothiazol-4-yl)-2-(2-propynyloxyimino)acetamido]-3-[(Z)-2-(3-pyridyl)vinylthiomethyl]-3-cephem-4-carboxylate (syn isomer)

IR (Nujol): 1770, 1710, 1660, 1600, 1520 cm$^{-1}$

(27) 7-[2-(2-Aminothiazol-4-yl)-2-(2-propynyloxyimino)acetamido]-3-[(Z)-2-(3-pyridyl)vinylthiomethyl]-3-cephem-4-carboxylic acid (syn isomer)

IR (Nujol): 1760, 1660, 1570, 1530 cm$^{-1}$

(28) Benzhydryl 7-[2-(5-amino-1,2,4-thiadiazol-3-yl)-2-allyloxyiminoacetamido]-3-[(Z)-2-(3-pyridyl)vinylthiomethyl]-3-cephem-4-carboxylate (syn isomer)

IR (Nujol): 1770, 1720, 1670, 1610, 1520 cm$^{-1}$

(29) 7-[2-(5-Amino-1,2,4-thiadiazol-3-yl)-2-allyloxyiminoacetamido]-3-[(Z)-2-(3-pyridyl)vinylthiomethyl]-3-cephem-4-carboxylic acid (syn isomer)

IR (Nujol): 1770, 1670, 1620, 1580, 1530, 1400 cm$^{-1}$

(30) Benzhydryl 7-[2-(5-amino-1,2,4-thiadiazol-3-yl)-2-allyloxyiminoacetamido]-3-[(Z)-2-cyanovinylthiomethyl]-3-cephem-4-carboxylates (syn isomer)

IR (Nujol): 3300, 2210, 1780, 1720, 1680, 1620 cm$^{-1}$

(31) 7-[2-(5-Amino-1,2,4-thiadiazol-3-yl)-2-allyloxyiminoacetamido]-3-[(Z)-2-cyanovinylthiomethyl]-3-cephem-4-carboxylic acid (syn isomer)

IR (Nujol): 3250, 2210, 1765, 1670, 1615 cm$^{-1}$

(32) 1-Acetoxyethyl 7-[2-(2-aminothiazol-4-yl)-2-allyloxyiminoacetamido]-3-[(Z)-2-(3-pyridyl)vinylthiomethyl]-3-cephem-4-carboxylate (syn isomer)

IR (Nujol): 3150–3300 (broad), 1760–1780 (broad), 1670, 1255, 1220, 1075 cm$^{-1}$

EXAMPLE 3

To a solution of benzhydryl 7-[2-(5-amino-1,2,4-thiadiazol-3-yl)-2-allyloxyiminoacetamido]-3-[(Z)-2-phenylvinylthiomethyl]-3-cephem-4-carboxylate (syn isomer) (748 mg) in a mixture of methylene chloride (2.24 ml), anisole (0.37 ml) and thioanisole (0.37 ml) was added trifluoroacetic acid (1.5 ml) under ice-cooling. The mixture was stirred for 30 minutes at the same temperature and poured into diisopropyl ether (50 ml). The resulting precipitate was collected, washed with diisopropyl ether and dissolved in a mixture of ethyl acetate and an aqueous solution of sodium bicarbonate at pH 7. The aqueous layer was separated, adjusted to pH 6.2 with diluted hydrochloric acid and extracted with ethyl acetate three times. The extract was dried over magnesium sulfate and concentrated in vacuo. The residue was triturated in diisopropyl ether to give 7-[2-(5-amino-1,2,4-thiadiazol-3-yl)-2-allyloxyiminoacetamido]-3-[(Z)-2-phenylvinylthiomethyl]-3-cephem-4-carboxylic acid (syn isomer) (207 mg).

mp: 153° C. (dec.)

IR (Nujol): 1765, 1670, 1620, 1520 cm$^{-1}$

NMR (DMSO-d$_6$, δ): 3.30–4.30 (4H, m), 4.67 (2H, d, J=5 Hz), 5.03–5.57 (3H, m), 5.67–6.27 (2H, m), 6.53 (2H, broad s), 7.00–7.60 (5H, m), 8.10 (2H, broad s), 9.57 (1H, d, J=8 Hz)

EXAMPLE 4

To a suspension of benzhydryl 7-[2-(2-aminothiazol-4-yl)-2-methoxyiminoacetamido]-3-[(Z)-2-(3-pyridyl)-vinylthiomethyl]-3-cephem-4-carboxylate (syn isomer) (1 g) in anisole (2.5 ml) was added trifluoroacetic acid (6 ml) under ice-cooling. The mixture was stirred for 40 minutes at ambient temperature, concentrated in vacuo to about a half volume and poured into diisopropyl ether (120 ml). The resulting precipitate was collected, dissolved in an aqueous solution (150 ml) of sodium bicarbonate (320 mg). The aqueous solution was washed with ethyl acetate and adjusted to pH 4–5 with 1N hydrochloric acid to give a precipitate. The precipitate was collected, washed with water and dried over phosphorus pentoxide to give 7-[2-(2-aminothiazol-4-yl)-2-methoxyiminoacetamido]-3-[(Z)-2-(3-pyridyl)-vinylthiomethyl]-3-cephem-4-carboxylic acid (syn isomer) (330 mg).

On the other hand, the washings were adjusted to pH 3 with 1N hydrochloric acid and extracted with a mixture of ethyl acetate and tetrahydrofuran. The extract was dried over magnesium sulfate and concentrated in vacuo. The residue was triturated in diisopropyl ether and dried to give a second crop (265 mg) of the object compound.

mp: 170° C. (dec.)

IR (Nujol): 3300, 3200, 1760, 1650, 1620, 1590, 1540, 1530, 1180, 1040 cm$^{-1}$ NMR (DMSO-d$_6$+D$_2$O, δ): 3.65 (2H, broad s), 3.78, 4.23 (2H, ABq, J=14 Hz), 3.83 (3H, s), 5.20 (1H, d, J=5 Hz), 5.78 (1H, d, J=5 Hz), 6.53 (1H, d, J=10 Hz), 6.77 (1H, s), 6.85 (1H, d, J=10 Hz), 7.13–7.6 (1H, m), 7.7–8.0 (1H, m), 8.4–8.6 (1H, m), 8.6–8.8 (1H, m) cl EXAMPLE 5

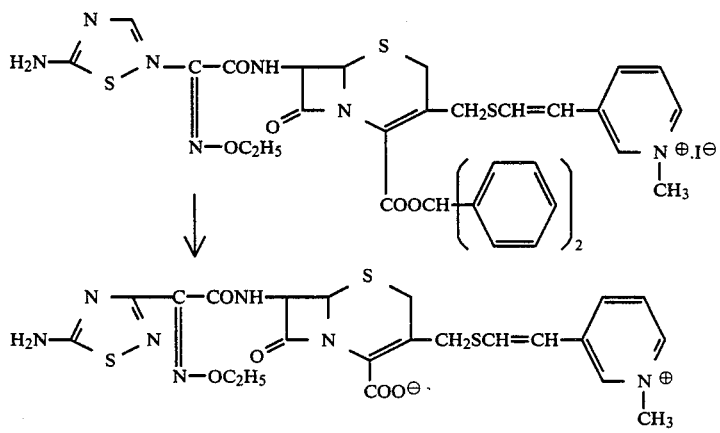

To a suspension of benzhydryl 7-[2-(5-amino-1,2,4-thiadiazol-3-yl)-2-ethoxyiminoacetamido]-3-[(Z)-2-(1-methyl-3-pyridino)vinylthiomethyl]-3-cephem-4-carboxylate iodide (syn isomer) (3.6 g) in a mixture of methylene chloride (10.8 ml) and anisole (3.6 ml) was added trifluoroacetic acid (7.2 ml) under ice-cooling. The mixture was stirred under same condition for 4 hours and poured into diisopropyl ether (400 ml) to give a precipitate. The precipitate was collected, dried and dissolved in water keeping the pH 6 with an aqueous solution of sodium bicarbonate. The aqueous solution was washed with ethyl acetate, adjusted to pH 5 with 1N hydrochloric acid and subjected to column chromatography on macroporous non-ionic adsorption resin "Diaion HP-20" [Trademark: prepared by Mitsubishi Chemical Industries ] (150 ml). After the column was washed with water, the elution was carried out with 2% aqueous isopropyl alcohol (300 ml), 3% aqueous isopropyl alcohol (220 ml), 4% aqueous isopropyl alcohol (300 ml), 5% aqueous isopropyl alcohol (450 ml), 7% aqueous isopropyl alcohol (300 ml), 10% aqueous isopropyl alcohol (300 ml), 15% aqueous isopropyl alcohol (300 ml) and 20% aqueous isopropyl alcohol (600 ml), successively. The fractions containing the object compound were combined, concentrated in vacuo and lyophilized to give 7-[2-(5-amino-1,2,4-thiadiazol-3-yl)-2-ethoxyiminoacetamido]-3-[(Z)-2-(1-methyl-3-pyridinio)vinylthiomethyl]-3-cephem-4-carboxylate (syn isomer) (530 mg)

IR (Nujol): 1755, 1660, 1590 cm$^{-1}$

NMR (D$_2$O+NaHCO$_3$, δ): 1.30 (3H, t, J=7 Hz), 3.47–4.57 (4H, m), 4.37 (3H, s), 4.73 (2H, q, J=7 Hz), 5.30 (1H, d, J=5 Hz), 5.80 (1H, d, J=5 Hz), 6.50 (1H, d, J=11 Hz), 7.03 (1H, d, J=11 Hz), 7.77–8.13 (1H, m), 8.30–8.80 (3H, m)

EXAMPLE 6

To a solution of benzhydryl 7-[2-(5-amino-1,2,4-thiadiazol-3-yl)-2-allyloxyiminoacetamido]-3-[(E)-2-(2-pyridyl)vinylthiomethyl]-3-cephem-4-carboxylate (syn isomer) (175 mg) in a mixture of methylene chloride (0.53 ml) and anisole (0.18 ml) was added trifluoroacetic acid under ice-cooling. The mixture was stirred for 2 hours at the same temperature. The mixture was poured into diisopropyl ether (50 ml) to give a precipitate. The precipitate was collected and washed with diisopropyl ether to give 7-[2-(5-amino-1,2,4-thiadiazol-3-yl)-2-allyloxyiminoacetamido]-3-[(E)-2-(2-pyridyl)vinylthiomethyl]-3-cephem-4-carboxylic acid monotrifluoroacetate (syn isomer) (89 mg).

NMR (DMSO-$d_6$, $\delta$): 3.50–3.87 (2H, m), 3.87–4.30 (2H, m), 4.67 (2H, d, J=5 Hz), 5.07–5.53 (3H, m), 5.60–6.23 (2H, m), 6.67 (1H, d, J=15 Hz), 7.10–8.30 (5H, m), 8.00 (1H, d, J=15 Hz), 8.60 (1H, d, J=5 Hz), 9.57 (1H, d, J=9 Hz)

EXAMPLE 7

To a suspension of benzhydryl 7-(2-phenylacetamido)-3-[(Z)-2-(3-pyridyl)vinylthiomethyl]-3-cephem-4-carboxylate (50 mg) in anisole (0.1 ml) was added trifluoroacetic acid (0.2 ml) under ice-cooling. The reaction mixture was stirred at ambient temperature for an hour. The mixture was poured into diisopropyl ether (5 ml) to give a precipitate. The precipitate was collected, washed with diisopropyl ether and dried to give 7-(2-phenylacetamido)-3-[(Z)-2-(3-pyridyl)vinylthiomethyl]-3-cephem-4-carboxylic acid monotrifluoroacetate (38 mg.)

IR (Nujol): 1775, 1660 cm$^{-1}$

NMR (DMSO-$d_6$, $\delta$): 3.53 (2H, s), 3.63 (2H, broad s), 3.80, 4.27 (2H, ABq, J=14 Hz), 5.10 (1H, d, J=5 Hz), 5.67 (1H, dd, J=5, 8 Hz), 6.57 (1H, d, J=11 Hz), 7.00 (1H, d, J=11 Hz), 7.27 (5H, s), 7.70 (1H, dd, J=5, 10 Hz), 8.30 (1H, dt, J=2, 10Hz), 8.60 (1H, dd, J=2, 5 Hz), 8.77 (1H, d, J=2 Hz), 9.07 (1H, d, J=8 Hz)

EXAMPLE 8

The following compounds were obtained according to similar manners to those of Examples 3–7.

(1) 7-[2-(5-Amino-1,2,4-thiadiazol-3-yl)-2-allyloxyiminoacetamido]-3-[(Z)-2-(2-pyridyl)vinylthiomethyl]-3-cephem-4-carboxylic acid (syn isomer)

mp: 172° C. (dec.)

IR (Nujol): 1760, 1665, 1610, 1565, 1530 cm$^{-1}$

NMR (DMSO-$d_6$, $\delta$): 3.44–3.84 (3H, m), 4.04 (1H, d, J=14 Hz), 4.68 (2H, d, J=5 Hz), 5.04–5.48 (3H, m), 5.68–6.20 (2H, m), 6.56 (1H, d, J=11 Hz), 6.92 (1H, d, J=11 Hz), 7.12–7.44 (2H, m), 7.68–7.88 (2H, m), 8.12 (2H, broad s), 8.60 (1H, d, J=4 Hz) and 9.56 (1H, d, J=9 Hz)

(2) 7-[2-(2-Aminothiazol-4-yl)-2-methoxyiminoacetamido]-[(Z)-2-(2-pyridyl)vinylthiomethyl]-3-cephem-4-carboxylic acid mp: 153° C. (dec.)

IR (Nujol): 1770, 1660, 1570 cm$^{-1}$

NMR (DMSO-$d_6$, $\delta$): 3.43–4.20 (4H, m), 3.87 (3H, s), 5.20 (1H, d, J=5 Hz), 5.73 (1H, dd, J=5 Hz, 8 Hz), 6.53 (1H, d, J=11 Hz), 6.80 (1H, s), 6.97 (1H, d, J=11 Hz), 7.00–7.50 (2H, m), 7.57–8.00 (1H, m), 8.50–8.67 (1H, m), 9.60 (1H, d, J=8 Hz)

(3) 7-[2-(5-Amino-1,2,4-thiadiazol-3-yl)-2-ethoxyiminoacetamido]-3-[(Z)-2-(2-pyridyl)vinylthiomethyl]-3-cephem-4-carboxylic acid (syn isomer)

mp: 175° C. (dec.)

IR (Nujol): 1765, 1670, 1610, 1570, 1520 cm$^{-1}$

NMR (DMSO-$d_6$, $\delta$): 1.23 (3H, t, J=7 Hz), 3.47–4.17 (4H, m), 4.13 (2H, q, J=7 Hz), 5.13 (1H, d, J=5 Hz), 5.77 (1H, dd, J=5 Hz, 8 Hz), 6.47 (1H, d, J=11 Hz), 6.93 (1H, d, J=11 Hz), 7.00–7.43 (2H, m), 7.60–8.23 (3H, m), 8.47–8.63 (1H, m), 9.47 (1H, d, J=8 Hz)

(4) 7-[2-(5-Amino-1,2,4-thiadiazol-3-yl)-2-ethoxyiminoacetamido]-3-[(Z)-2-(3-pyridyl)vinylthiomethyl]-3-cephem-4-carboxylic acid (syn isomer)

mp: 156° C. (dec.)

IR (Nujol): 3300, 3200, 1770, 1670, 1620, 1580, 1530, 1250, 1230, 1180 cm$^{-1}$ NMR (D$_2$O+NaHCO$_3$, $\delta$): 1.23 (3H, t, J=7 Hz), 3.27–3.66 (2H, m), 3.66–4.03 (2H, m), 4.27 (2H, q, J=7 Hz), 5.20 (1H, d, J=5 Hz), 5.87 (1H, d, J=5 Hz), 6.30 (1H, d, J=11 Hz), 6.67 (1H, d, J=7 Hz), 7.10–7.40 (1H, m), 7.60–7.80 (1H, m), 8.07–8.30 (1H, m), 8.30–8.50 (1H, m)

(5) 7-[2-(5-Amino-1,2,4-thiadiazol-3-yl)-2-ethoxyiminoacetamido]-3-[2-(3-pyridyl)ethynylthiomethyl]-3-cephem-4-carboxylic acid (syn isomer)

IR (Nujol): 3290, 3180, 2140, 1770, 1670, 1815, 1525 cm$^{-1}$

NMR (DMSO-$d_6$, $\delta$): 1.23 (3H, d, J=8 Hz), 3.23–4.50 (4H, m), 4.20 (2H, q, J=8 Hz), 5.30 (1H, d, J=5 Hz), 5.80 (1H, dd, J=5, 8 Hz), 7.40 (1H, dd, J=5, 8 Hz), 7.83 (1H, dt, J=2, 8 Hz), 8.00–8.33 (2H, m), 8.47–8.70 (2H, m), 9.53 (1H, d, J=8 Hz)

(6) 7-[2-(2-Aminothiazol-4-yl)-2-allyloxyiminoacetamido]-3-[(Z)-2-(3-pyridyl)vinylthiomethyl]-3-cephem-4-carboxylic acid (syn isomer)

mp: 145° C. (dec.)

IR (Nujol): 1770, 1670, 1530 cm$^{-1}$

NMR (DMSO-$d_6$, $\delta$): 3.64 (2H, broad s), 3.7–4.4 (2H, m), 4.64 (2H, d, J=5 Hz), 4.9–5.5 (3H, m), 5.6–6.2 (2H, m), 6.6, 7.0 (2H, ABq, J=11 Hz), 6.8 (1H, s), 7.6–7.8 (1H, m), 8–9 (3H, m), 9.7 (1H, d, J=8 Hz)

(7) 7-[2-(2-Aminothiazol-4-yl)-2-(2-propynyloxyimino)acetamido]-3-[(Z)-2-(3-pyridyl)vinylthiomethyl]-3-cephem-4-carboxylic acid (syn isomer)

IR (Nujol): 1760, 1660, 1570, 1530 cm$^{-1}$

NMR (DMSO-$d_6$, $\delta$): 3.37 (1H, s), 3.5–4.3 (4H, m), 4.7 (2H, broad s), 5.1 (1H, d, J=5 Hz), 5.75 (1H, dd, J=5 Hz, 8 Hz), 6.6, 6.9 (2H, ABq, J=11 Hz), 7.5–7.8 (1H, m), 8.0–8.2 (1H, m), 8.4–8.8 (2H, m), 9.7 (1H, d, J=8 Hz)

mp: 135° C. (dec.)

(8) 7-[2-(5-Amino-1,2,4-thiadiazol-3-yl)-2-allyloxyiminoacetamido]-3-[(Z)-2-(3-pyridyl)vinylthiomethyl]-3-cephem-4-carboxylic acid (syn isomer)

IR (Nujol): 1770, 1670, 1620, 1580, 1530, 1400 cm$^{-1}$

NMR (DMSO-$d_6$, $\delta$): 3.6 (2H, broad s), 3.6–4.3 (2H, m), 4.63 (2H, d, J=5 Hz), 5.0–5.5 (2H, m), 5.2 (1H, d, J=5 Hz), 5.6–6.3 (1H, m), 5.8 (1H, dd, J=5 Hz, 8 Hz), 6.47, 6.83 (2H, ABq, J=11 Hz), 7.47 (1H, q, J=6 Hz, 8 Hz), 7.93 (1H, dt, J=2 Hz, 8 Hz), 8.1 (2H, broad s), 8.43 (1H, dd, J=2 Hz, 6 Hz), 8.63 (1H, d, J=2 Hz), 9.57 (1H, d, J=8 Hz)

(9) 7-[2-(5-Amino-1,2,4-thiadiazol-3-yl)-2-allyloxyiminoacetamido]-3-[(Z)-2-cyanovinylthiomethyl]-3-cephem-4-carboxylic acid (syn isomer)

IR (Nujol): 3250, 2210, 1765, 1670, 1615 cm$^{-1}$

NMR (DMSO-$d_6$, $\delta$): 3.6 (2H, broad s), 3.8 and 4.25 (2H, ABq, J=14 Hz), 4.67 (2H, d, J=5 Hz), 5.2 (1H, d, J=5 Hz), 5.17–6.2 (3H, m), 5.7 (1H, d, J=11 Hz), 5.77 (1H, dd, J=8 Hz, 5 Hz), 7.75 (1H, d, J=11 Hz), 8.1 (2H, broad s), 9.6 (1H, d, J=8 Hz)

EXAMPLE 9

To a solution of (Z)-2-acetylthiovinylbenzene (500 mg) in tetrahydrofuran (5 ml) was dropwise added a solution of sodium methoxide (13.9 mg) in a mixture of methanol (358 mg) and tetrahydrofuran (2 ml) under ice-cooling. The mixture was stirred for 30 minutes under the same condition. The resulting solution was dropwise added to a solution of benzhydryl 7-[2-(5-amino-1,2,4-thiadiazol-3-yl)-2-allyloxyiminoacetamido]-3-chloromethyl-3-cephem-4-carboxylate (syn isomer) (1.46 g) in tetrahydrofuran (20 ml) at −30° C. The mixture was stirred at the same temperature for 30 minutes. The reaction temperature was gradually raised to 0° C. 1N Hydrochloric acid (3 ml) was added to the reaction mixture at 0° C. Ethyl acetate and a saturated aqueous solution of sodium chloride were added to the mixture. The separated organic layer was washed with a saturated aqueous solution of sodium chloride, dried over magnesium sulfate and concentrated in vacuo. The residue was triturated in diisopropyl ether to give a solid, which was subjected to column chromatography on silica gel (50 g) and eluted with a mixture of chloroform and methanol (100:1, V/V). The fractions containing the object compound were combined and concentrated in vacuo. The residue was triturated in diisopropyl ether to give benzhydryl 7-[2-(5-amino-1,2,4-thiadiazol-3-yl)-2-allyloxyiminoacetamido]-3-[(Z)-2-phenylvinylthiomethyl]-3-cephem-4-carboxylate (syn isomer) (790 mg).

IR (Nujol): 1770, 1720, 1670, 1620, 1520 cm$^{-1}$

NMR (DMSO-d$_6$, δ): 3.50–3.80 (2H, m), 3.80–4.13 (2H, m), 4.67 (2H, d, J=5 Hz), 5.07–5.53 (2H, m), 5.27 (1H, d, J=5 Hz), 5.60–6.13 (2H, m), 6.37 (2H, broad s), 6.97 (1H, s), 7.10–7.67 (15H, m), 8.00–8.23 (2H, m), 9.60 (1H, d, J=8 Hz)

EXAMPLE 10

To a suspension of [(Z and E)-2-(2-pyridyl)vinylthio]silver (1.9 g) in acetonitrile (80 ml) was added sodium iodide (6.9 g) at ambient temperature. The mixture was stirred for 30 minutes at the same temperature. To this mixture was added a solution of benzhydryl 7-[2-(5-amino-1,2,4-thiadiazol-3-yl)-2-allyloxyiminoacetamido]-3-chloromethyl-3-cephem-4-carboxylate (syn isomer) (2.88 g) in acetonitrile (30 ml) under ice-cooling. The mixture was stirred for 1 hour at the same temperature. The insoluble material was filtered off. The filtrate was concentrated in vacuo to give a residue. The residue was dissolved in a mixture of ethyl acetate and a saturated aqueous solution of sodium chloride, and the mixture was stirred for 1 hour at ambient temperature. Sellaite was added to the mixture and the insoluble material was filtered off. The separated organic layer was dried over sodium sulfate and concentrated in vacuo. The residue was subjected to a column chromatography on silica gel (175 g) and eluted with a mixture of ethyl acetate and n-hexane (3:1, V/V). The fraction containing the material having a larger Rf value in thin layer chromatography was combined and concentrated in vacuo to give benzhydryl 7-[2-(5-amino-1,2,4-thiadiazol-3-yl)-2-allyloxyiminoacetamido]-3-[(Z)-2-(2-pyridyl)vinylthiomethyl]-3-cephem-4-carboxylate (syn isomer) (1.58 g).

IR (Nujol): 1770, 1715, 1670, 1610, 1590, 1520 cm$^{-1}$

NMR (DMSO-d$_6$, δ): 3.30–4.10 (4H, m), 4.67 (2H, d, J=5 Hz), 5.07–5.53 (3H, m), 5.73–6.27 (2H, m), 6.40 (1H, d, J=11 Hz), 6.70 (1H, d, J=11 Hz), 6.97 (1H, s), 7.10–7.93 (13H, m), 8.10 (2H, broad s), 8.50–8.71 (1H, m), 9.60 (1H, d, J=8 Hz)

The fractions containing the material having a smaller Rf value in thin layer chromatography were combined and concentrated in vacuo to give benzhydryl 7-[2-(5-amino-1,2,4-thiadiazol-3-yl)-2-allyloxyiminoacetamido]-3-[(E)-2-(2-pyridyl)vinylthiomethyl]-3-cephem-4-carboxylate (syn isomer) (230 mg).

IR (Nujol): 1780, 1720, 1670, 1600, 1580, 1520 cm$^{-1}$

NMR (DMSO-d$_6$, δ): 3.33–4.13 (4H, m), 4.67 (2H, d, J=5 Hz), 5.07–5.53 (3H, m), 5.63–6.23 (2H, m), 6.53 (1H, d, J=15 Hz), 6.97 (1H, s), 7.10–7.77 (14H, m), 8.10 (2H, broad s), 8.37–8.63 (1H, m), 9.60 (1H, d, J=9 Hz)

EXAMPLE 11

To a suspension of [(Z)-2-(3-pyridyl)vinylthio]silver (167 mg) in acetonitrile (20 ml) was added sodium iodide (544 mg) at ambient temperature. The mixture was stirred for 35 minutes. To the resultant mixture was added benzhydryl 7-(2-phenylacetamido)-3-chloromethyl-3-cephem-4-carboxylate (193 mg) under ice-cooling.

The mixture was stirred for an hour. The insoluble material was filtered off. The filtrate was concentrated in vacuo to give a residue, which was dissolved in ethyl acetate. The solution was washed with a saturated aqueous solution of sodium chloride, dried over magnesium sulfate and concentrated in vacuo. The residue was subjected to column chromatography on silica gel (10 g) eluting with a mixture of ethyl acetate and n-hexane (4:6). The fractions containing the object compound were combined and concentrated in vacuo to give benzhydryl 7-(2-phenylacetamido)-3-[(Z)-2-(3-pyridyl)vinylthiomethyl]-3-cephem-4-carboxylate as a solid (148 mg).

IR (Nujol): 1770, 1705, 1640 cm$^{-1}$

NMR (DMSO-d$_6$, δ): 3.30–4.23 (6H, m), 5.20 (1H, d, J=5 Hz), 5.77 (1H, dd, J=5, 8 Hz), 6.37 (1H, d, J=12 Hz), 6.60 (1H, d, J=12 Hz), 7.97 (1H, s), 7.13–7.63 (16H, m), 7.80 (1H, dt, J=2, 8 Hz), 8.43 (1H, dd, J=2, 5 Hz), 8.60 (1H, d, J=2 Hz), 9.10 (1H, d, J=8 Hz)

EXAMPLE 12

To a suspension of benzhydryl 7-amino-3-chloromethyl-3-cephem-4-carboxylate monohydrochloride (120 mg) in acetonitrile (5 ml) was added bis(trimethylsilyl)urea (217 mg) at ambient temperature. The resulting mixture was stirred at 40° C. for 30 minutes to give a clear solution. On the other hand, to a suspension of [(Z)-2-(3-pyridyl)vinylthio]silver (122 mg) in acetonitrile (4 ml) was added sodium iodide (396 mg) at ambient temperature. The mixture was stirred for 10 minutes. To this mixture was added the above clear solution at 0° C. The mixture was stirred at 0° C. for 2 hours and at ambient temperature for 2 hours. The insoluble material was filtered off.

The filtrate was concentrated in vacuo. The residue was dissolved in a mixture of ethyl acetate and tetrahydrofuran. The solution was washed with a saturated aqueous solution of sodium chloride, dried over sodium sulfate, concentrated in vacuo, and the residue was triturated in diisopropyl ether to give benzhydryl 7-amino-3-[(Z)-2-(3-pyridyl)vinylthiomethyl]-3-cephem-4-carboxylate (90 mg) as a solid.

IR (Nujol): 1760, 1710 cm$^{-1}$

NMR (DMSO-d$_6$, δ): 3.63 (2H, broad s), 3.73, 4.00 (2H, ABq, J=14 Hz), 4.83 (1H, d, J=4 Hz), 5.07 (1H, d, J=4 Hz), 6.33 (1H, d, J=12 Hz), 6.57 (1H, d, J=12 Hz), 6.93 (1H, s), 7.13–7.60 (11H, m), 7.63–8.73 (3H, m)

EXAMPLE 13

To a solution of 3-ethynylpyridine (258 mg) in a mixture of tetrahydrofuran (7 ml) and hexamethylphosphoric triamide (0.3 ml) was dropwise added n-butyllithium (1.55M in hexane) (1.3 ml) at −30° C. Sulfur (72 mg) was added to the reaction mixture at −25° C. at once. The mixture was stirred for 30 minutes under ice-cooling and then allowed to warm to 15° C. to give a solution containing 3-(2-lithiothioethynyl)pyridine. This solution was added to a solution of benzhydryl 7-[2-(5-amino-1,2,4-thiadiazol-3-yl)-2-ethoxyiminoacetamido]-3-iodomethyl-3-cephem-4-carboxylate (syn isomer) (1.4 g) in tetrahydrofuran (20 ml) at −50° C. The mixture was stirred for 40 minutes at −50° C. To the mixture was added 6N hydrochloric acid (1 ml) at −60° C. The mixture was warmed up to ambient temperature. To the mixture was added a mixture of ethyl acetate and water. The separated organic layer was dried over sodium sulfate, concentrated in vacuo, and the residue was triturated in diisopropyl ether to give a solid. The solid was subjected to column chromatography on silica gel (15 g) eluting with a mixture of ethyl acetate and n-hexane (1:1 (V/V), 4:1 (V/V)). The fractions containing the object compound were combined, concentrated in vacuo, and the residue was triturated in diethyl ether to give benzhydryl 7-[2-(5-amino-1,2,4-thiadiazol-3-yl)-2-ethoxyiminoacetamido]-3-[2-(3-pyridyl)ethynylthiomethyl]-3-cephem-4-carboxylate (syn isomer) (576 mg).

IR (Nujol): 2170, 1775, 1720, 1670, 1520 cm$^{-1}$

NMR (DMSO-d$_6$, δ): 1.23 (3H, d, J=7 Hz), 3.53, 3.80 (2H, ABq, J=18 Hz), 4.00 (2H, broad s), 4.20 (2H, q, J=7 Hz), 5.27 (1H, d, J=5 Hz), 5.90 (1H, dd, J=5, 9 Hz), 7.83 (1H, s), 7.13–7.53 (11H, m), 7.67 (1H, dt, J=2, 8 Hz), 7.90–8.27 (2H, m), 8.37–8.67 (2H, m), 9.57 (1H, d, J=9 Hz)

EXAMPLE 14

To a suspension of [(Z)-2-(3-pyridyl)vinylthio]silver (51 g, purity 88%) in acetonitrile (2 l) was added sodium iodide (132.7 g) at ambient temperature. After the mixture was stirred for 30 minutes, a solution of benzhydryl 7-[2-(2-formamidothiazol-4-yl)-2-allyloxyiminoacetamido]-3-chloromethyl-3-cephem-4-carboxylate (syn isomer) (80 g) in acetonitrile (1 l) was dropwise added to the reaction mixture at 0° C. The mixture was stirred for 1.5 hours.

The insoluble material was filtered off. The filtrate was concentrated in vacuo to give a residue. The residue was dissolved in a mixture of ethyl acetate and tetrahydrofuran. The organic layer was washed with a saturated aqueous solution of sodium chloride, dried over magnesium sulfate and concentrated in vacuo and the residue was triturated in diisopropyl ether to give benzhydryl 7-[2-(2-formamidothiazol-4-yl)-2-allyloxyiminoacetamido]-3-[(Z)-2-(3-pyridyl)vinylthiomethyl]-3-cephem-4-carboxylate (syn isomer) (23.57 g).

IR (Nujol): 3250, 1775, 1710, 1650 cm$^{-1}$

NMR (DMSO-d$_6$, δ): 3.67 (2H, broad s), 3.8–4.0 (2H, m), 4.67 (2H, d, J=5 Hz), 5.0–5.5 (3H, m), 5.7–6.2 (2H, m), 6.36, 6.58 (2H, ABq, J=11 Hz), 6.97 (1H, s), 7.3–7.67 (11H, broad s), 7.8 (1H, dt, J=2 Hz, 8 Hz), 8.33–8.67 (2H, m), 8.5 (1H, s), 9.73 (1H, d, J=8 Hz), 12.62 (1H, s)

EXAMPLE 15

The following compounds were obtained according to similar manners to those of Examples 9–14.

(1) Benzhydryl 7-[2-(2-formamidothiazol-4-yl)-2-methoxyiminoacetamido]-3-[(Z)-2-(3-pyridyl)vinylthiomethyl]-3-cephem-4-carboxylate (syn isomer)

IR (Nujol): 3250, 1775, 1715, 1690, 1660 cm$^{-1}$ (2) 7-[2-(5-Amino-1,2,4-thiadiazol-3-yl)-2-allyloxyiminoacetamido]-3-[(Z)-2-phenylvinylthiomethyl]-3-cephem-4-carboxylic acid (syn isomer)

mp: 153° C. (dec.)

IR (Nujol): 1765, 1670, 1620, 1520 cm$^{-1}$ (3) 7-[2-(5-Amino-1,2,4-thiadiazol-3-yl)-2-allyloxyiminoacetamido]-3-[(Z)-2-(2-pyridyl)vinylthiomethyl]-3-cephem-4-carboxylic acid (syn isomer)

mp: 172° C. (dec.)

IR (Nujol): 1760, 1665, 1610, 1565, 1530 cm$^{-1}$ (4) 7-[2-(5-Amino-1,2,4-thiadiazol-3-yl)-2-allyloxyiminoacetamido]-3-[(E)-2-(2-pyridyl)vinylthiomethyl]-3-cephem-4-carboxylic acid monotrifluoroacetate (syn isomer)

NMR (DMSO-d$_6$, δ): 3.50–3.87 (2H, m), 3.87–4.30 (2H, m), 4.67 (2H, d, J=5 Hz), 5.07–5.53 (3H, m), 5.60–6.23 (2H, m), 6.67 (1H, d, J=15 Hz), 7.10–8.30 (5H, m), 8.00 (1H, d, J=15 Hz), 8.60 (1H, d, J=5 Hz), 9.57 (1H, d, J=9 Hz)

(5) Benzhydryl 7-[2-(2-formamidothiazol-4-yl)-2-methoxyiminoacetamido]-3-[(Z)-2-(2-pyridyl)vinylthiomethyl]-3-cephem-4-carboxylate (syn isomer)

IR (Nujol): 1770, 1710, 1690, 1660, 1580, 1540 cm$^{-1}$

NMR (DMSO-d$_6$, δ): 3.70 (2H, broad s), 3.67–4.17 (2H, m), 3.90 (3H, s), 5.30 (1H, d, J=5 Hz), 5.90 (1H, dd, J=5 Hz, J=8 Hz), 6.43 (1H, d, J=11 Hz), 6.70 (1H, d, J=11 Hz), 6.90 (1H, s), 6.97 (1H, s), 7.10–7.90 (13H, m), 8.43–8.67 (1H, m), 8.50 (1H, s), 9.70 (1H, d, J=8 Hz)

(6) Benzhydryl 7-[2-(2-aminothiazol-4-yl)-2-methoxyiminoacetamido]-3-[(Z)-2-(2-pyridyl)vinylthiomethyl]-3-cephem-4-carboxylate (syn isomer)

IR (Nujol): 1775, 1715, 1665, 1610, 1590, 1520 cm$^{-1}$ (7) 7-[2-(2-Aminothiazol-4-yl)-2-methoxyiminoacetamido]-3-[(Z)-2-(2-pyridyl)vinylthiomethyl]-3-cephem-4-carboxylic acid (syn isomer)

mp: 153° C. (dec.)

IR (Nujol): 1770, 1660, 1570 cm$^{-1}$ (8) Benzhydryl 7-[2-(5-amino-1,2,4-thiadiazol-3-yl)-2-ethoxyiminoacetamido]-3-[(Z)-2-(2-pyridyl)vinylthiomethyl]-3-cephem-4-carboxylate (syn isomer)

NMR (DMSO-d$_6$, δ): 1.23 (3H, t, J=7 Hz), 3.67 (2H, broad s), 3.53–4.30 (2H, m), 4.17 (2H, q, J=7 Hz), 5.27 (1H, d, J=5 Hz), 5.90 (1H, dd, J=5 Hz, 8 Hz), 6.33 (1H, d, J=11 Hz), 6.70 (1H, d, J=11 Hz), 6.97 (1H, s), 7.07–7.90 (13H, m), 8.10 (2H, broad s), 8.47–8.67 (1H, m), 9.57 (1H, d, J=8 Hz)

(9) 7-[2-(5-Amino-1,2,4-thiadiazol-3-yl)-2-ethoxyiminoacetamido]-3-[(Z)-2-(2-pyridyl)vinylthiomethyl]-3-cephem-4-carboxylic acid (syn isomer)

mp: 175° C. (dec.)

IR (Nujol): 1765, 1670, 1610, 1570, 1520 cm$^{-1}$

(10) 7-(2-Phenylacetamido)-3-[(Z)-2-(3-pyridyl)vinylthiomethyl]-3-cephem-4-carboxylic acid monotrifluoroacetate IR (Nujol): 1775, 1660 cm$^{-1}$

(11) Benzhydryl 7-[2-(2-aminothiazol-4-yl)-2-methoxyiminoacetamido]-3-[(Z)-2-(3-pyridyl)vinylthiomethyl]-3-cephem-4-carboxylate (syn isomer)

IR (Nujol): 1770, 1710, 1670, 1610, 1530, 1300, 1240 cm$^{-1}$

(12) 7-[2-(2-Aminothiazol-4-yl)-2-methoxyiminoacetamido]-3-[(Z)-2-(3-pyridyl)vinylthiomethyl]-3-cephem-4-carboxylic acid (syn isomer)

mp: 170° C. (dec.)

IR (Nujol): 3300, 3200, 1760, 1650, 1620, 1590, 1540, 1530, 1180, 1040 cm$^{-1}$

(13) Benzhydryl 7-[2-(5-amino-1,2,4-thiadiazol-3-yl)-2-ethoxyiminoacetamido]-3-[(Z)-2-(3-pyridyl)vinylthiomethyl]-3-cephem-4-carboxylate (syn isomer)

IR (Nujol): 3300, 3150, 1780, 1720, 1675, 1610, 1530 cm$^{-1}$

NMR (DMSO-d$_6$, δ): 1.27 (3H, t, J=7 Hz), 3.67 (2H, broad s), 3.77 and 4.03 (2H, ABq, J=14 Hz), 4.20 (2H, q, J=7 Hz), 5.27 (1H, d, J=5 Hz), 6.97 (1H, dd, J=5, 9 Hz), 6.27 (1H, d, J=11 Hz), 6.60 (1H, d, J=11 Hz), 7.00 (1H, s), 7.20–7.67 (11H, m), 7.83 (1H, dt, J=2, 8 Hz), 8.00–8.27 (2H, m), 8.43 (1H, dd, J=2, 5 Hz), 8.60 (1H, d, J=2 Hz), 9.60 (1H, d, J=9 Hz)

(14) 7-[2-(5-Amino-1,2,4-thiadiazol-3-yl)-2-ethoxyiminoacetamido]-3-[(Z)-2-(3-pyridyl)vinylthiomethyl]-3-cephem-4-carboxylic acid (syn isomer)

mp: 156° C. (dec.)

IR (Nujol): 3300, 3200, 1770, 1670, 1620, 1580, 1530, 1250, 1230, 1180 cm$^{-1}$

(15) Benzhydryl 7-[2-(5-amino-1,2,4-thiadiazol-3-yl)-2-ethoxyiminoacetamido]-3-[(Z)-2-(1-methyl-3-pyridinio)vinylthiomethyl]-3-cephem-4-carboxylate iodide (syn isomer)

IR (Nujol): 1770, 1720, 1670, 1610, 1570, 1520 cm$^{-1}$

(16) 7-[2-(5-Amino-1,2,4-thiadiazol-3-yl)-2-ethoxyiminoacetamido]-3-[(Z)-2-(1-methyl-3-pyridinio)vinylthiomethyl]-3-cephem-4-carboxylate (syn isomer)

IR (Nujol): 1755, 1660, 1590 cm$^{-1}$

(17) 7-[2-(5-Amino-1,2,4-thiadiazol-3-yl)-2-ethoxyiminoacetamido]-3-[2-(3-pyridyl)ethynylthiomethyl]-3-cephem-4-carboxylic acid (syn isomer)

IR (Nujol): 3290, 3180, 2140, 1770, 1670, 1615, 1525 cm$^{-1}$

(18) Benzhydryl 7-[2-(2-aminothiazol-4-yl)-2-allyloxyiminoacetamido]-3-[(Z)-2-(3-pyridyl)vinylthiomethyl]-3-cephem-4-carboxylate (syn isomer)

IR (Nujol): 1770, 1720, 1670, 1610, 1530, 1300, 1240 cm$^{-1}$

(19) 7-[2-(2-Aminothiazol-4-yl)-2-allyloxyiminoacetamido]-3-[(Z)-2-(3-pyridyl)vinylthiomethyl]-3-cephem-4-carboxylic acid (syn isomer)

mp: 145° C. (dec.)

IR (Nujol): 1770, 1670, 1530 cm$^{-1}$

(20) Benzhydryl 7-[2-(2-formamidothiazol-4-yl)-2-(2-propynyloxyimino)acetamido]-3-[(Z)-2-(3-pyridyl)-vinylthiomethyl]-3-cephem-4-carboxylate (syn isomer)

IR (Nujol): 1770, 1715, 1660, 1530 cm$^{-1}$

NMR (DMSO-d$_6$, δ): 3.67 (2H, broad s), 3.8–4.1 (2H, m), 4.77 (2H, d, J=2 Hz), 5.33 (1H, d, J=5 Hz), 5.93 (1H, dd, J=5 Hz, 8 Hz), 6.4, 6.6 (2H, ABq, J=11 Hz), 7.0 (1H, s), 7.1–7.67 (12H, broad s), 7.83 (1H, dt, J=2 Hz, 8 Hz), 8.33 (1H, dd, J=2 Hz, 6 Hz), 8.5–8.67 (1H, m), 9.8 (1H, d, J=8 Hz)

(21) Benzhydryl 7-[2-(2-aminothiazol-4-yl)-2-(2-propynyloxyimino)acetamido]-3-[(Z)-2-(3-pyridyl)-vinylthiomethyl]-3-cephem-4-carboxylate (syn isomer)

IR (Nujol): 1770, 1710, 1660, 1600, 1520 cm$^{-1}$

(22) 7-[2-(2-Aminothiazol-4-yl)-2-(2-propynyloxyimino)acetamido]-3-[(Z)-2-(3-pyridyl)vinylthiomethyl]-3-cephem-4-carboxylic acid (syn isomer)

IR (Nujol): 1760, 1660, 1570, 1530 cm$^{-1}$

(23) Benzhydryl 7-[2-(5-amino-1,2,4-thiadiazol-3-yl)-2-allyloxyiminoacetamido]-3-[(Z)-2-(3-pyridyl)vinylthiomethyl]-3-cephem-4-carboxylate (syn isomer)

IR (Nujol): 1770, 1720, 1670, 1610, 1520 cm$^{-1}$

NMR (DMSO-d$_6$, δ): 3.67 (2H, broad s), 3.90 (2H, d, J=5 Hz), 4.67 (2H, d, J=5 Hz), 5.0–5.5 (2H, m), 5.27 (1H, d, J=5 Hz), 5.67–6.1 (2H, m), 6.35, 6.58 (2H, ABq, J=12 Hz), 6.97 (1H, s), 7.4 (11H, s), 7.8 (1H, dt, J=2 Hz), 8.12 (2H, s), 8.3 (1H, dd, J=2 Hz, 6 Hz), 8.58 (1H, d, J=2 Hz), 9.66 (1H, d, J=8 Hz)

(24) 7-[2-(5-Amino-1,2,4-thiadiazol-3-yl)-2-allyloxyiminoacetamido]-3-[(Z)-2-(3-pyridyl)vinylthiomethyl]-3-cephem-4-carboxylic acid (syn isomer)

IR (Nujol): 1770, 1670, 1620, 1580, 1530, 1400 cm$^{-1}$

(25) Benzhydryl 7-[2-(5-amino-1,2,4-thiadiazol-3-yl)-2-allyloxyiminoacetamido]-3-[(Z)-2-cyanovinylthiomethyl]-3-cephem-4-carboxylate (syn isomer)

IR (Nujol): 3300, 2210, 1780, 1720, 1680, 1620 cm$^{-1}$

NMR (DMSO-d$_6$, δ): 3.67 (2H, broad s), 3.83 and 4.12 (2H, ABq, J=14 Hz), 4.7 (2H, d, J=5 Hz), 5.1–6.1 (4H, m), 5.28 (1H, d, J=5 Hz), 5.65 (1H, d, J=10 Hz), 6.97 (1H, s), 7.2–7.7 (10H, m), 7.55 (1H, d, J=10 Hz), 8.13 (2H, broad s), 9.63 (1H, d, J=8 Hz)

(26) 7-[2-(5-Amino-1,2,4-thiadiazol-3-yl)-2-allyloxyiminoacetamido]-3-[(Z)-2-cyanovinylthiomethyl]-3-cephem-4-carboxylic acid (syn isomer)

IR (Nujol): 3250, 2210, 1765, 1670, 1615 cm$^{-1}$

(27) 1-Acetoxyethyl 7-[2-(2-aminothiazol-4-yl)-2-allyloxyiminoacetamido]-3-[(Z)-2-(3-pyridyl)vinylthiomethyl]-3-cephem-4-carboxylate (syn isomer)

IR (Nujol): 3150–3300 (broad), 1760–1780 (broad), 1670, 1255, 1220, 1075 cm$^{-1}$

EXAMPLE 16

To a suspension of benzhydryl 7-[2-(2-formamidothiazol-4-yl)-2-methoxyiminoacetamido]-3-[(Z)-2-(3-pyridyl)vinylthiomethyl]-3-cephem-4-carboxylate (syn isomer) (1.21 g) in methanol (24 ml) was added conc. hydrochloric acid (0.52 ml) at ambient temperature. The mixture was stirred for 1.5 hours at 35° C. The mixture was concentrated in vacuo to give a residue, which was dissolved in a mixture of ethyl acetate and water. The mixture was adjusted to pH 7 with an aqueous solution of sodium bicarbonate. The separated organic layer was washed with water and a saturated aqueous solution of sodium chloride in turn, dried over magnesium sulfate and concentrated in vacuo, and the residue was triturated in diisopropyl ether to give benzhydryl 7-[2-(2-aminothiazol-4-yl)-2-methoxyiminoacetamido]-3-[(Z)-2-(3-pyridyl)vinylthiomethyl]-3-cephem-4-carboxylate (syn isomer) (1.05 g).

IR (Nujol): 1770, 1710, 1670, 1610, 1530, 1300, 1240 cm$^{-1}$

NMR (DMSO-d$_6$, δ): 3.69 (2H, broad s), 3.7–4.2 (2H, m), 3.85 (3H, s), 5.28 (1H, d, J=5 Hz), 5.90 (1H, dd, J=5, 8 Hz), 6.40 (1H, d, J=11 Hz), 6.63 (1H, d, J=11 Hz), 6.77 (1H, s), 7.00 (1H, s), 7.20 (2H, broad s), 7.2–7.7 (11H, m), 7.7–8.0 (1H, m), 8.4–8.6 (1H, m), 8.6–8.7 (1H, m), 9.62 (1H, d, J=8 Hz)

EXAMPLE 17

To a suspension of benzhydryl 7-[2-(2-formamidothiazol-4-yl)-2-allyloxyiminoacetamido]-3-[(Z)-2-(3-pyridyl)vinylthiomethyl]-3-cephem-4-carboxylate (syn isomer) (23.5 g) in methanol (950 ml) was added conc. hydrochloric acid (12.7 ml) at ambient temperature. The mixture was stirred for 50 minutes at 35° C. The mixture was concentrated in vacuo to give a residue, which was dissolved in a mixture of ethyl acetate, tetrahydrofuran and water. The mixture was adjusted to pH 7 with an aqueous solution of sodium bicarbonate. The organic layer was separated, washed with water and a saturated aqueous solution of sodium chloride in turn, dried over magnesium sulfate and concentrated in vacuo, and the residue was triturated in diisopropyl ether to give benzhydryl 7-[2-(2-aminothiazol-4-yl)-2-allyloxyiminoacetamido]-3-[(Z)-2-(3-pyridyl)vinylthiomethyl]-3-cephem-4-carboxylate (syn isomer) (21.5 g)

IR (Nujol): 1770, 1720, 1670, 1610, 1530, 1300, 1240 cm$^{-1}$

NMR (DMSO-d$_6$, δ): 3.67 (2H, broad s), 3.7–4.2 (2H, m), 4.6 (2H, d, J=5 Hz), 5.0–5.6 (3H, m), 5.7–6.2 (2H, m), 6.4, 6.6 (2H, ABq, J=11 Hz), 6.77 (1H, s), 6.96 (1H, s), 7.2–7.7 (11H, broad s), 7.83 (1H, dt, J=2 Hz, 10 Hz), 8.4 (1H, dd, J=2 Hz, 5 Hz), 8.6 (1H, d, J=2 Hz), 9.6 (1H, d, J=7 Hz)

EXAMPLE 18

The following compounds were obtained according to similar manners to those of Examples 16 and 17.

(1) Benzhydryl 7-[2-(5-amino-1,2,4-thiadiazol-3-yl)-2-allyloxyiminoacetamido]-3-[(Z)-2-phenylvinylthiomethyl]-3-cephem-4-carboxylate (syn isomer)

IR (Nujol): 1770, 1720, 1670, 1620, 1520 cm$^{-1}$ (2) 7-[2-(5-Amino-1,2,4-thiadiazol-3-yl)-2-allyloxyiminoacetamido]-3-[(Z)-2-phenylvinylthiomethyl]-3-cephem-4-carboxylic acid (syn isomer)

mp: 153° C. (dec.)

IR (Nujol): 1765, 1670, 1620, 1520 cm$^{-1}$ (3) Benzhydryl 7-[2-(5-amino-1,2,4-thiadiazol-3-yl)-2-allyloxyiminoacetamido]-3-[(Z)-2-(2-pyridyl)vinylthiomethyl]-3-cephem-4-carboxylate (syn isomer)

IR (Nujol): 1770, 1715, 1670, 1610, 1590, 1520 cm$^{-1}$ (4) Benzhydryl 7-[2-(5-amino-1,2,4-thiadiazol-3-yl)-2-allyloxyiminoacetamido]-3-[(E)-2-(2-pyridyl)vinylthiomethyl]-3-cephem-4-carboxylate (syn isomer)

IR (Nujol): 1780, 1720, 1670, 1600, 1580, 1520 cm$^{-1}$ (5) 7-[2-(5-Amino-1,2,4-thiadiazol-3-yl)-2-allyloxyiminoacetamido]-3-[(Z)-2-(2-pyridyl)vinylthiomethyl]-3-cephem-4-carboxylic acid (syn isomer)

mp: 172° C. (dec.)

IR (Nujol): 1760, 1665, 1610, 1565, 1530 cm$^{-1}$ (6) 7-[2-(5-Amino-1,2,4-thiadiazol-3-yl)-2-allyloxyiminoacetamido]-3-[(E)-2-(2-pyridyl)vinylthiomethyl]-3-cephem-4-carboxylic acid monotrifluoroacetate (syn isomer)

NMR (DMSO-d$_6$, δ): 3.50–3.87 (2H, m), 3.87–4.30 (2H, m), 4.67 (2H, d, J=5 Hz), 5.07–5.53 (3H, m), 5.60–6.23 (2H, m), 6.67 (1H, d, J=15 Hz), 7.10–8.30 (5H, m), 8.00 (1H, d, J=15 Hz), 8.60 (1H, d, J=5 Hz), 9.57 (1H, d, J=9 Hz)

(7) Benzhydryl 7-[2-(2-aminothiazol-4-yl)-2-methoxyiminoacetamido]-3-[(Z)-2-(2-pyridyl)vinylthiomethyl]-3-cephem-4-carboxylate (syn isomer)

IR (Nujol): 1775, 1715, 1665, 1610, 1590, 1520 cm$^{-1}$

NMR (DMSO-d$_6$, δ): 3.67 (2H, broad s), 3.60–4.10 (2H, m), 3.83 (3H, s), 5.27 (1H, d, J=5 Hz), 5.87 (1H, dd, J=5 Hz, 9 Hz), 6.43 (1H, d, J=11 Hz), 6.70 (1H, d, J=11 Hz), 6.77 (1H, s), 6.97 (1H, s), 7.07–7.90 (13H, m), 8.50–8.70 (1H, m), 9.60 (1H, d, J=9 Hz)

(8) 7-[2-(2-Aminothiazol-4-yl)-2-methoxyiminoacetamido]-3-[(Z)-2-(2-pyridyl)vinylthiomethyl]-3-cephem-4-carboxylic acid (syn isomer)

mp: 153° C. (dec.)

IR (Nujol): 1770, 1660, 1570 cm$^{-1}$ (9) Benzhydryl 7-[2-(5-amino-1,2,4-thiadiazol-3-yl)-2-ethoxyiminoacetamido]-3-[(Z)-2-(2-pyridyl)vinylthiomethyl]-3-cephem-4-carboxylate (syn isomer)

NMR (DMSO-d$_6$, δ): 1.23 (3H, t, J=7 Hz), 3.67 (2H, broad s), 3.53–4.30 (2H, m), 4.17 (2H, q, J=7 Hz), 5.27 (1H, d, J=5 Hz), 5.90 (1H, dd, J=5 Hz, 8 Hz), 6.33 (1H, d, J=11 Hz), 6.70 (1H, d, J=11 Hz), 6.97 (1H, s), 7.07–7.90 (13H, m), 8.10 (2H, broad s), 8.47–8.67 (1H, m), 9.57 (1H, d, J=8 Hz)

(10) 7-[2-(5-Amino-1,2,4-thiadiazol-3-yl)-2-ethoxyiminoacetamido]-3-[(Z)-2-(2-pyridyl)vinylthiomethyl]-3-cephem-4-carboxylic acid (syn isomer)

mp: 175° C. (dec.)

IR (Nujol): 1765, 1670, 1610, 1570, 1520 cm$^{-1}$

(11) 7-[2-(2-Aminothiazol-4-yl)-2-methoxyiminoacetamido]-3-[(Z)-2-(3-pyridyl)viinylthiomethyl]-3-cephem-4-carboxylic acid (syn isomer)

mp: 170° C. (dec.)

IR (Nujol): 3300, 3200, 1760, 1650, 1620, 1590, 1540, 1530, 1180, 1040 cm$^{-1}$

(12) Benzhydryl 7-[2-(5-amino-1,2,4-thiadiazol-3-yl)-2-ethoxyiminoacetamido]-3-[(Z)-2-(3-pyridyl)vinylthiomethyl]-3-cephem-4-carboxylate (syn isomer)

IR (Nujol): 3300, 3150, 1780, 1720, 1675, 1610, 1530 cm$^{-1}$

(13) 7-[2-(5-Amino-1,2,4-thiadiazol-3-yl)-2-ethoxyiminoacetamido]-3-[(Z)-2-(3-pyridyl)vinylthiomethyl]-3-cephem-4-carboxylic acid (syn isomer)

mp: 156° C. (dec.)

IR (Nujol): 3300, 3200, 1770, 1670, 1620, 1580, 1530, 1250, 1230, 1180 cm$^{-1}$

(14) Benzhydryl 7-[2-(5-amino-1,2,4-thiadiazol-3-yl)-2-ethoxyiminoacetamido]-3-[(Z)-2-(1-methyl-3-pyridinio)vinylthiomethyl]-3-cephem-4-carboxylate iodide (syn isomer)

IR (Nujol): 1770, 1720, 1670, 1610, 1570, 1520 cm$^{-1}$

(15) 7-[2-(5-Amino-1,2,4-thiadiazol-3-yl)-2-ethoxyiminoacetamido]-3-[(Z)-2-(1-methyl-3-pyridinio)vinylthiomethyl]-3-cephem-4-carboxylate (syn isomer)

IR (Nujol): 1755, 1660, 1590 cm$^{-1}$

(16) Benzhydryl 7-[2-(5-amino-1,2,4-thiadiazol-3-yl)-2-ethoxyiminoacetamido]-3-[2-(3-pyridyl)ethynylthiomethyl]-3-cephem-4-carboxylate (syn isomer)

IR (Nujol): 2170, 1775, 1720, 1670, 1520 cm$^{-1}$

(17) 7-[2-(5-Amino-1,2,4-thiadiazol-3-yl)-2-ethoxyiminoacetamido]-3-[2-(3-pyridyl)ethynylthiomethyl]-3-cephem-4-carboxylic acid (syn isomer)

IR (Nujol): 3290, 3180, 2140, 1770, 1670, 1615, 1525 cm$^{-1}$

(18) 7-[2-(2-Aminothiazol-4-yl)-2-allyloxyiminoacetamido]-3-[(Z)-2-(3-pyridyl)vinylthiomethyl]-3-cephem-4-carboxylic acid (syn isomer)

mp: 145° C. (dec.)

IR (Nujol): 1770, 1670, 1530 cm$^{-1}$

(19) 7-[2-(2-Aminothiazol-4-yl)-2-(2-propynyloxyimino)acetamido]-3-[(Z)-2-(3-pyridyl)vinylthiomethyl]-3-cephem-4-carboxylic acid (syn isomer)

IR (Nujol): 1760, 1660, 1570, 1530 cm$^{-1}$

(20) Benzhydryl 7-[2-(5-amino-1,2,4-thiadiazol-3-yl)-2-allyloxyiminoacetamido]-3-[(Z)-2-(3-pyridyl)vinylthiomethyl]-3-cephem-4-carboxylate (syn isomer)

IR (Nujol): 1770, 1720, 1670, 1610, 1520 cm$^{-1}$

(21) 7-[2-(5-Amino-1,2,4-thiadiazol-3-yl)-2-allyloxyiminoacetamido]-3-[(Z)-2-(3-pyridyl)vinylthiomethyl]-3-cephem-4-carboxylic acid (syn isomer)

IR (Nujol): 1770, 1670, 1620, 1580, 1530, 1400 cm$^{-1}$

(22) Benzhydryl 7-[2-(5-amino-1,2,4-thiadiazol-3-yl)-2-allyloxyiminoacetamido]-3-[(Z)-2-cyanovinylthiomethyl]-3-cephem-4-carboxylate (syn isomer)

IR (Nujol): 3300, 2210, 1780, 1720, 1680, 1620 cm$^{-1}$

(23) 7-[2-(5-Amino-1,2,4-thiadiazol-3-yl)-2-allyloxyiminoacetamido]-3-[(Z)-2-cyanovinylthiomethyl]-3-cephem-4-carboxylic acid (syn isomer)

IR (Nujol): 3250, 2210, 1765, 1670, 1615 cm$^{-1}$

(24) Benzhydryl 7-[2-(2-aminothiazol-4-yl)-2-(2-aminothiazol-4-yl)-2-(2-propynyloxyimino)acetamido]-3-[(Z)-2-(3-pyridyl)vinylthiomethyl]-3-cephem-4-carboxylate (syn isomer)

IR (Nujol): 1770, 1710, 1660, 1600, 1520 cm$^{-1}$

NMR (DMSO-d$_6$, δ): 3.3–3.4 (1H, m), 3.67 (2H, broad s), 3.8–4.1 (2H, m), 4.72 (2H, d, J=2 Hz), 5.3 (1H, d, J=5 Hz), 5.81 (1H, dd, J=5 Hz, 8 Hz), 6.4, 6.57 (2H, ABq, J=11 Hz), 6.8 (1H, s), 7.0 (1H, s), 7.1–7.67 (11H, broad s), 7.88 (1H, dt, J=2 Hz, 8 Hz), 8.4 (1H, dd, J=2 Hz, 6 Hz), 8.6 (1H, d, J=2 Hz), 9.7 (1H, d, J=8 Hz)

(25) 1-Acetoxyethyl 7-[2-(2-aminothiazol-4-yl)-2-allyloxyiminoacetamido]-3-[(Z)-2-(3-pyridyl)vinylthiomethyl]-3-cephem-4-carboxylate (syn isomer)

IR (Nujol): 3150–3300 (broad), 1760–1780 (broad), 1670, 1255, 1220, 1075 cm$^{-1}$

EXAMPLE 19

To a solution of benzhydryl 7-[2-(5-amino-1,2,4-thiadiazol-3-yl)-2-ethoxyiminoacetamido]-3-[(Z)-2-(3-pyridyl)vinylthiomethyl]-3-cephem-4-carboxylate (syn isomer) (1.80 g) in a mixture of tetrahydrofuran (16 ml) and water (6 ml) was added methyl iodide (1.6 ml) at ambient temperature. The mixture was stirred for 4 days in the dark at the same temperature. The mixture was concentrated in vacuo to give a residue. The residue was triturated in diethyl ether to give benzhydryl 7-[2-(5-amino-1,2,4-thiadiazol-3-yl)-2-ethoxyiminoacetamido]-3-[(Z)-2-(1-methyl-3-pyridinio)vinylthiomethyl]-3-cephem-4-carboxylate iodide (syn isomer) (2.21 g).

IR (Nujol): 1770, 1720, 1670, 1610, 1570, 1520 cm$^{-1}$

NMR (DMSO-d$_6$, δ): 1.23 (3H, t, J=8 Hz), 3.67 (2H, broad s), 3.77–4.43 (2H, m), 4.17 (2H, q, J=8 Hz), 4.33 (3H, s), 5.27 (1H, d, J=5 Hz), 6.90 (1H, dd, J=5, 8 Hz), 6.50 (1H, d, J=11 Hz), 6.93 (1H, s), 7.00 (1H, d, J=11 Hz), 7.13–7.60 (10H, m), 7.93–8.30 (3H, m), 8.33–8.60 (1H, m), 8.66–9.00 (2H, m), 9.53 (1H, d, J=8 Hz)

EXAMPLE 20

The following compound was obtained according to a similar manner to that of Example 19.

7-[2-(5-Amino-1,2,4-thiadiazol-3-yl)-2-ethoxyiminoacetamido]-3-[(Z)-2-(1-methyl-3-pyridinio)vinylthiomethyl]-3-cephem-4-carboxylate (syn isomer)

IR (Nujol): 1755, 1660, 1590 cm$^{-1}$

EXAMPLE 21

To a solution of 7-[2-(2-aminothiazol-4-yl)-2-allyloxyiminoacetamido]-3-[(Z)-2-(3-pyridyl)vinylthiomethyl]-3-cephem-4-carboxylic acid (syn isomer) in N,N-dimethylformamide (30 ml) was added cesium carbonate (0.47 g). The mixture was stirred for 30 minutes at 25° C., and 1-bromoethyl acetate (1.35 g) was added dropwise thereto at 0°–3° C. After stirring for 1 hour, the reaction mixture was poured into ethyl acetate (200 ml) and the insoluble material was filtered off. The filtrate was washed with water (200 ml×2), an aqueous solution of sodium bicarbonate (100 ml×1) and a saturated aqueous solution of sodium chloride successively, and dried over magnesium sulfate. The ethyl acetate was distilled off under reduced pressure, and the residue was pulverized with diisopropyl ether to give 1-acetoxyethyl 7-[2-(2-aminothiazol-4-yl)-2-allyloxyiminoacetamido]-3-[(Z)-2-(3-pyridyl)vinylthiomethyl]-3-cephem-4-carboxylate (syn isomer) (0.63 g).

IR (Nujol): 3150–3300 (broad), 1760–1780 (broad), 1670, 1255, 1220, 1075 cm$^{-1}$ NMR (DMSO-d$_6$, δ): 1.52 (3H, d, J=6 Hz), 2.06 (3H, s), 3.6–3.76 (2H, m), 3.6–4.2 (2H, m), 4.58 (2H, d, J=5 Hz), 5.0–5.48 (3H, m), 5.68–6.16 (2H, m), 6.64 (2H, dd, J=12 Hz, 24 Hz), 6.72 (1H, s), 6.84–7.07 (1H, m), 7.44 (1H, dd, J=5 Hz, 9 Hz), 7.88 (1H, d, J=8 Hz), 8.36–8.52 (1H, m), 8.52–8.68 (1H, m), 9.59 (1H, d, J=8 Hz)

EXAMPLE 22

The following compounds were obtained according to a similar manner to that of Example 21.

(1) Benzhydryl 7-[2-(2-formamidothiazol-4-yl)-2-methoxyiminoacetamido]-[(Z)-2-(3-pyridyl)vinylthiomethyl]-3-cephem-4-carboxylate (syn isomer)

IR (Nujol): 3250, 1775, 1715, 1690, 1660 cm$^{-1}$ (2) Benzhydryl 7-[2-(5-amino-1,2,4-thiadiazol-3-yl)-2-allyloxyiminoacetamido]-3-[(Z)-2-phenylvinylthiomethyl]-3-cephem-4-carboxylate (syn isomer)

IR (Nujol): 1770, 1720, 1670, 1620, 1520 cm$^{-1}$ (3) Benzhydryl 7-[2-(5-amino-1,2,4-thiadiazol-3-yl)-2-allyloxyiminoacetamido]-3-[(Z)-2-(2-pyridyl)vinylthiomethyl]-3-cephem-4-carboxylate (syn isomer)

IR (Nujol): 1770, 1715, 1670, 1610, 1590, 1520 cm$^{-1}$ (4) Benzhydryl 7-[2-(5-amino-1,2,4-thiadiazol-3-yl)-2-allyloxyiminoacetamido]-3-[(E)-2-(2-pyridyl)vinylthiomethyl]-3-cephem-4-carboxylate (syn isomer)

IR (Nujol): 1780, 1720, 1670, 1600, 1580, 1520 cm$^{-1}$ (5) Benzhydryl 7-[2-(2-formamidothiazol-4-yl)-2-methoxyiminoacetamido]-3-[(Z)-2-(2-pyridyl)vinylthiomethyl]-3-cephem-4-carboxylate (syn isomer)

IR (Nujol): 1770, 1710, 1690, 1660, 1580, 1540 cm$^{-1}$ (6) Benzhydryl 7-[2-(2-aminothiazol-4-yl)-2-methoxyiminoacetamido]-3-[(Z)-2-(2-pyridyl)vinylthiomethyl]-3-cephem-4-carboxylate (syn isomer)

IR (Nujol): 1775, 1715, 1665, 1610, 1590, 1520 cm$^{-1}$ (7) Benzhydryl 7-[2-(5-amino-1,2,4-thiadiazol-3-yl)-2-ethoxyiminoacetamido]-3-[(Z)-2-(2-pyridyl)vinylthiomethyl]-3-cephem-4-carboxylate (syn isomer)

NMR (DMSO-d$_6$, δ): 1.23 (3H, t, J=7 Hz), 3.67 (2H, broad s), 3.53–4.30 (2H, m), 4.17 (2H, q, J=7 Hz), 5.27 (1H, d, J=5 Hz), 5.90 (1H, dd, J=5 Hz, 8 Hz), 6.33 (1H, d, J=11 Hz), 6.70 (1H, d, J=11 Hz), 6.97 (1H, s), 7.07–7.90 (13H, m), 8.10 (2H, broad s), 8.47–8.67 (1H, m), 9.57 (1H, d, J=8 Hz)

(8) Benzhydryl 7-(2-phenylacetamido)-3-[(Z)-2-(3-pyridyl)vinylthiomethyl]-3-cephem-4-carboxylate IR (Nujol): 1770, 1705, 1640 cm$^{-1}$ (9) Benzhydryl 7-[2-(2-aminothiazol-4-yl)-2-methoxyiminoacetamido]-3-[(Z)-2-(3-pyridyl)vinylthiomethyl]-3-cephem-4-carboxylate (syn isomer)

IR (Nujol): 1770, 1710, 1670, 1610, 1530, 1300, 1240 cm$^{-1}$

(10) Benzhydryl 7-[2-(5-amino-1,2,4-thiadiazol-3-yl)-2-ethoxyiminoacetamido]-3-[(Z)-2-(3-pyridyl)vinylthiomethyl]-3-cephem-4-carboxylate (syn isomer)

IR (Nujol): 3300, 3150, 1780, 1720, 1675, 1610, 1530 cm$^{-1}$

(11) Benzhydryl 7-[2-(5-amino-1,2,4-thiadiazol-3-yl)-2-ethoxyiminoacetamido]-3-[(Z)-2-(1-methyl-3-pyridinio)vinylthiomethyl]-3-cephem-4-carboxylate iodide (syn isomer)

IR (Nujol): 1770, 1720, 1670, 1610, 1570, 1520 cm$^{-1}$

(12) Benzhydryl 7-[2-(5-amino-1,2,4-thiadiazol-3-yl)-2-ethoxyiminoacetamido]-3-[2-(3-pyridyl)ethynylthiomethyl]-3-cephem-4-carboxylate (syn isomer)

IR (Nujol): 2170, 1775, 1720, 1670, 1520 cm$^{-1}$

(13) Benzhydryl 7-[2-(2-formamidothiazol-4-yl)-2-allyloxyiminoacetamido]-3-[(Z)-2-(3-pyridyl)vinylthiomethyl]-3-cephem-4-carboxylate (syn isomer)

IR (Nujol): 3250, 1775, 1710, 1650 cm$^{-1}$

(14) Benzhydryl 7-[2-(2-aminothiazol-4-yl)-2-allyloxyiminoacetamido]-3-[(Z)-2-(3-pyridyl)vinylthiomethyl]-3-cephem-4-carboxylate (syn isomer)

IR (Nujol): 1770, 1720, 1670, 1610, 1530, 1300, 1240 cm$^{-1}$

(15) Benzhydryl 7-[2-(2-formamidothiazol-4-yl)-2-(2-propynyloxyimino)acetamido]-3-[(Z)-2-(3-pyridyl)-vinylthiomethyl]-3-cephem-4-carboxylate (syn isomer)
IR (Nujol): 1770, 1715, 1660, 1530 cm$^{-1}$

(16) Benzhydryl 7-[2-(2-aminothiazol-4-yl)-2-(2-propynyloxyimino)acetamido]-3-[(Z)-2-(3-pyridyl)-vinylthiomethyl]-3-cephem-4-carboxylate (syn isomer)
IR (Nujol): 1770, 1710, 1660, 1600, 1520 cm$^{-1}$

(17) Benzhydryl 7-[2-(5-amino-1,2,4-thiadiazol-3-yl)-2-allyloxyiminoacetamido]-3-[(Z)-2-(3-pyridyl)vinylthiomethyl]-3-cephem-4-carboxylate (syn isomer)
IR (Nujol): 1770, 1720, 1670, 1610, 1520 cm$^{-1}$

(18) Benzhydryl 7-[2-(5-amino-1,2,4-thiadiazol-3-yl)-2-allyloxyiminoacetamido]-3-[(Z)-2-cyanovinylthiomethyl]-3-cephem-4-carboxylate (syn isomer)
IR (Nujol): 3300, 2210, 1780, 1720, 1680, 1620 cm$^{-1}$

(19) Benzhydryl 7-amino-3-[(Z)-2-(3-pyridyl)vinylthiomethyl]-3-cephem-4-carboxylate
IR (Nujol): 1760, 1710 cm$^{-1}$

PREPARATION 10

A mixture of 3-[(Z)-2-(tritylthio)vinyl]pyridine (5 g) and methyl iodide (8.3 ml) in dry methylene chloride (100 ml) was stirred at ambient temperature for 24 hours. The reaction mixture was poured into diethyl ether under stirring. The resultant precipitate was collected by filtration, washed with diethyl ether and air-dried at ambient temperature to give 3-[(Z)-2-(tritylthio)vinyl]-1-methylpyridinium iodide (6.64 g) as yellow powder.

NMR (DMSO-d$_6$, δ): 4.33 (3H, s), 6.35, 6.55 (2H, ABq, J=12 Hz), 7.0–7.4 (18H, m), 8.40 (1H, dd, J=5 Hz, 8 Hz), 8.57 (1H, d, J=8 Hz), 8.73 (1H, d, J=5 Hz), 8.90 (1H, s)

PREPARATION 11

To a solution of (E)-3-chloroacrylonitrile (0.1 g) in tetrahydrofuran (2 ml) were added triphenylmethanethiol (0.332 g) and triethylamine (0.175 ml) under ice-cooling. The mixture was stirred at ambient temperature for 16 hours and poured into ice-water. The mixture was extracted with ethyl acetate. The extract was washed with brine, dried over magnesium sulfate and evaporated in vacuo to give (E)-3-tritylthioacrylonitrile (0.37 g).

IR (Film): 2210, 1560, 1490, 1440 cm$^{-1}$
NMR (DMSO-d$_6$, δ): 5.26 (1H, d, J=16 Hz), 5.78 (1H, d, J=16 Hz), 7–7.3 (15H, m)

PREPARATION 12

The following compound was obtained according to a similar manner to that of Preparation 5.
[(E)-2-cyanovinylthio]silver
IR (Nujol): 2210, 1540, 920, 860 cm$^{-1}$

PREPARATION 13

The following compound was obtained according to a similar manner to that of Preparation 3.
2-Methyl-5-[(Z)-2-(tritylthio)vinyl]pyridine
IR (Nujol): 1590, 1490, 1445 cm$^{-1}$
NMR (DMSO-d$_6$, δ): 2.43–2.60 (3H, hidden), 5.93, 6.40 (2H, ABq, J=10 Hz), 6.93–7.50 (16H, m), 7.80 (1H, dd, J=3 Hz, 7 Hz), 8.50 (1H, d, J=3 Hz)

PREPARATION 14

The following compound was obtained according to a similar manner to that of Preparation 5.
[(Z)-2-(2-Methyl-5-pyridyl)vinylthio]silver
IR (Nujol): 1570, 1540 cm$^{-1}$

PREPARATION 15

To a solution of N,N-diisopropylamine (3.39 ml) in anhydrous tetrahydrofuran (80 ml) was added 1.55M n-butyllithium in n-hexane at 60° C. The mixture was stirred for 30 minutes at 0° C. To the solution was added a solution of 2-ethoxy-1,3-oxathiolane (3 ml) in tetrahydrofuran (5 ml) at −60°~−70° C. After the mixture was stirred for 30 minutes at −65° C., the mixture was poured into a solution of silver nitrate (8.46 g) in a mixture of water (20 ml) and methanol (80 ml) under ice-cooling, stirred for 30 minutes and adjusted to pH 6.5 with dilute hydrochloric acid. The precipitate was collected by filtration, washed with water, methanol and diethyl ether successively, and dried to give vinylthiosilver (7.41 g).

PREPARATION 16

To a suspension of phorphorus pentachloride (624 mg) in methylene chloride (15 ml) was added pyridine (0.242 ml) at −20° C. After the mixture was stirred for 20 minutes at the same temperature, p-nitrobenzyl 7-(2-phenylacetamido)-3-chloromethyl-3-cephem-4-carboxylate (502 mg) was added to the mixture at −20° C. The mixture was stirred for 30 minutes under ice-cooling. To the mixture was added methanol (0.65 ml) at −20° C., and the mixture was stirred for an hour at −20°~−5° C. Water (0.7 ml) was added thereto under ice-cooling. The mixture was stirred for an hour at the same temperature to give a precipitate. The precipitate was collected, washed with methylene chloride, water and diisopropyl ether successively and dried over phosphorus pentoxide to give p-nitrobenzyl 7-amino-3-chloromethyl-3-cephem-4-carboxylate monohydrochloride (0.35 g).

IR (Nujol): 2600, 1780, 1715, 1610, 1530, 1500, 1360, 1310, 1235 cm$^{-1}$
NMR (DMSO-d$_6$, δ): 3.77 (2H, s), 4.51 and 4.65 (2H, ABq, J=14 Hz), 5.22 (1H, d, J=5 Hz), 5.31 (1H, d, J=5 Hz), 5.45 (2H, s), 7.70 (2H, d, J=8 Hz), 8.23 (2H, d, J=8 Hz)

PREPARATION 17

The following compounds were obtained according to a similar manner to that of Preparation 8.

(1) Benzhydryl 7-[2-(2-formamidothiazol-4-yl)-2-isopropoxyiminoacetamido]-3-chloromethyl-3-cephem-4-carboxylate (syn isomer).
IR (Nujol): 1780, 1720, 1540 cm$^{-1}$
NMR (DMSO-d$_6$, δ): 1.23 (2H, d, J=6 Hz), 3.5–3.8 (2H, m), 4.2–4.6 (3H, m), 5.27 (1H, d, J=5 Hz), 5.93 (1H, dd, J=5 Hz, 8 Hz), 6.93 (1H, s), 7.1–7.6 (11H, m), 8.46 (1H, s), 9.60 (1H, d, J=8 Hz)

(2) p-Nitrobenzyl 7-[2-methoxyimino-2-{2-(2,2,2-trifluoroacetamido)thiazol-4-yl}acetamido]-3-chloromethyl-3-cephem-4-carboxylate (syn isomer).
IR (Nujol): 3240, 1775, 1720, 1660, 1520, 1345, 1260, 1210 cm$^{-1}$
NMR (DMSO-d$_6$, δ): 3.4–4.0 (2H, m), 3.93 (3H, s), 4.58 (2H, broad s), 5.30 (1H, d, J=5 Hz), 5.47 (2H, s), 5.95 (1H, dd, J=5 Hz and 8 Hz), 7.55 (1H, s), 7.73 (2H, d, J=8 Hz), 8.28 (2H, d, J=8 Hz), 9.78 (1H, d, J=8 Hz)

(3) Benzhydryl 7-[2-{(Z)-2-cyanovinylthio}-acetamido]-3-chloromethyl-3-cephem-4-carboxylate.
IR (Nujol): 2210, 1780, 1720, 1690 cm$^{-1}$
NMR (DMSO-d$_6$, δ): 3.67 (2H, broad s), 3.7 (2H, s), 4.4 (2H, broad s), 5.2 (1H, d, J=5 Hz), 5.7 (1H, d, J=10

Hz), 5.8 (1H, dd, J=8 Hz, 5 Hz), 6.98 (1H, s), 7.2–7.67 (10H, m), 7.63 (1H, d, J=10 Hz), 9.22 (1H, d, J=8 Hz)

EXAMPLE 23

To a suspension of phosphorus pentachloride-pyridine complex (prepared from phosphorus pentachloride (1.31 g) and pyridine (0.508 ml)) in methylene chloride was added p-nitrobenzyl 7-(2-phenylacetamido)-3-vinylthiomethyl-3-cephem-4-carboxylate (1.10 g) at $-20°$ C. The mixture was stirred for 20 minutes under ice-cooling and poured into methanol (20 ml), and then an aqueous solution of sodium bicarbonate (2.1 g) was added thereto. The organic layer was separated at pH 4, washed with water, an aqueous solution of sodium bicarbonate and a saturated aqueous solution of sodium chloride successively and dried over magnesium sulfate. The inorganic material was filtered off, and to the filtrate was added bis(trimethylsilyl)urea (5.93 g). The mixture was stirred at 30° C. for 15 minutes to give a solution of the silylated 7-aminocephalosporanic acid derivative. On the other hand, phosphorus oxychloride (0.442 g) was added to a solution of N,N-dimethylformamide (0.207 ml) in ethyl acetate (0.65 ml) under ice-cooling. The mixture was stirred at the same temperature for 30 minutes. To the mixture were added 2-(p-nitrobenzyloxycarbonylmethoxyimino)-2-[2-(2,2,2-trifluoroacetamido)thiazol-4-yl]acetic acid (syn isomer) (1.14 g), methylene chloride (55 ml) and tetrahydrofuran (2 ml) at the same temperature and the mixture was stirred for 30 minutes to give an activated acid solution. This solution was added to the solution of the silylated 7-aminocephalosporanic acid derivative at $-20°$ C. The mixture was stirred at $-20° \sim -10°$ C. for 30 minutes, poured into ice-water and adjusted to pH 7 with an aqueous solution of sodium bicarbonate. The organic layer was separated, washed with a diluted aqueous solution of sodium bicarbonate, water and a saturated aqueous solution of sodium chloride in turn, dried over magnesium sulfate and concentrated in vacuo. The residue was purified by silica gel (25 g) column chromatography using a mixture of chloroform and methanol (50:1) as an eluent to give p-nitrobenzyl 7-[2-(p-nitrobenzyloxycarbonylmethoxyimino)-2-{2-(2,2,2-trifluoroacetamido)thiazol-4-yl}acetamido]-3-vinylthiomethyl-3-cephem-4-carboxylate (syn isomer) (1.23 g).

IR (Nujol): 1760, 1730, 1680, 1605, 1580, 1520, 1350, 1260, 1210 cm$^{-1}$

NMR (DMSO-d$_6$, δ): 3.4–3.7 (2H, m), 3.70 and 3.94 (2H, ABq, J=14 Hz), 4.86 (2H, s), 5.09 (1H, d, J=5 Hz), 5.2–5.5 (4H, m), 5.28 (1H, d, J=10 Hz), 5.32 (1H, d, J=17 Hz), 5.88 (1H, dd, J=5 Hz and 8 Hz), 6.47 (1H, dd, J=10 Hz and 17 Hz), 7.26 (1H, s), 7.64 (2H, d, J=8 Hz), 7.67 (2H, d, J=8 Hz), 8.15 (2H, d, J=8 Hz), 8.22 (2H, d, J=8 Hz), 9.77 (1H, d, J=8 Hz)

EXAMPLE 24

To a suspension of 7-amino-3-[(Z)-2-(3-pyridyl)vinylthiomethyl]-3-cephem-4-carboxylic acid (0.72 g) in dry tetrahydrofuran (10 ml) was added bis(trimethylsilyl)acetamide (1.7 ml) at ambient temperature and the mixture was stirred at the same temperature for an hour. On the other hand, to a solution of 2-(2-aminothiazol-4-yl)-2-(3-thietanyloxyimino)acetic acid (syn isomer) (0.42 g) and diisopropylethylamine in N,N-dimethylformamide (15 ml) was added mesyl chloride (0.25 ml) at $-55°$ C. and the mixture was stirred for half an hour. This solution was added to the above mentioned reaction mixture at $-30°$ C. The mixture was stirred at $-30°$ to 0° C. for an hour and added to a mixture of water and ethyl acetate under stirring. The mixture was adjusted to pH 7 with a saturated aqueous solution of sodium bicarbonate. Aqueous layer was separated, concentrated in vacuo to remove ethyl acetate and subjected to column chromatography on macroporous non-ionic adsorption resin "Diaion HP 20" (20 ml). After the column was washed with water, the elution was carried out with 20% aqueous isopropyl alcohol. The fractions containing the object compound were collected, evaporated to remove isopropyl alcohol under reduced pressure and lyophilized to give 7-[2-(2-aminothiazol-4-yl)-2-(3-thietanyloxyimino)acetamido]-3-[(Z)-2-(3-pyridyl)vinylthiomethyl]-3-cephem-4-carboxylic acid (anti isomer) (0.2 g).

mp: 150° C. (dec.)

IR (Nujol): 1780, 1660, 1520 cm$^{-1}$

NMR (DMSO-d$_6$, δ): 3.0–4.3 (8H, m), 5.0–5.5 (2H, m), 5.75 (1H, dd, J=5H, 8 Hz), 6.45, 6.80 (2H, ABq, J=12 Hz), 7.07 (2H, broad s), 7.38 (1H, dd, J=5 Hz, 8 Hz), 7.57 (1H, s), 7.8 (1H, d, J=8 Hz), 8.37 (1H, d, J=5 Hz), 8.60 (1H, m), 9.40 (1H, d, J=8 Hz)

EXAMPLE 25

The following compounds were obtained according to a similar manner to that of Example 1.

(1) Benzhydryl 7-[2-(2-formamidothiazol-4-yl)-2-isopropoxyiminoacetamido]-3-[(Z)-2-(1-methyl-3-pyridinio)vinylthiomethyl]-3-cephem-4-carboxylate nitrate (syn isomer)

IR (Nujol): 1780, 1720, 1670, 1540 cm$^{-1}$ (2) 7-[2-(2-Aminothiazol-4-yl)-2-isopropoxyiminoacetamido]-3-[(Z)-2-(1-methyl-3-pyridinio)vinylthiomethyl]-3-cephem-4-carboxylate (syn isomer)

mp: 145° C. (dec.)

IR (Nujol): 1770, 1670, 1600 cm$^{-1}$ (3) 7-[2-Methoxyimino-2-{2-(2,2,2-trifluoroacetamido)thiazol-4-yl}acetamido]-3-vinylthiomethyl-3-cephem-4-carboxylic acid (syn isomer)

IR (Nujol): 3200, 1770, 1710, 1650, 1580, 1500, 1250, 1200 cm$^{-1}$ (4) 7-[2-(2-Aminothiazol-4-yl)-2-methoxyiminoacetamido]-3-vinylthiomethyl-3-cephem-4-carboxylic acid hydrochloride (syn isomer)

mp: 195°–205° C. (dec.)

IR (Nujol): 1760, 1650, 1580, 1520 cm$^{-1}$ (5) 7-[2-(5-Amino-1,2,4-thiadiazol-3-yl)-2-ethoxyiminoacetamido]-3-(2-trimethylsilylethynylthiomethyl)-3-cephem-4-carboxylic acid (syn isomer)

mp: 123° C. (dec.)

IR (Nujol): 3300, 3190, 2080, 1765, 1670, 1615, 1515 cm$^{-1}$ (6) Benzhydryl 7-[2-(2-formamidothiazol-4-yl)-2-(3-thietanyloxyimino)acetamido]-3-[(Z)-2-(3-pyridyl)vinylthiomethyl]-3-cephem-4-carboxylate (syn isomer)

IR (Nujol): 1770, 1660, 1240, 1160 cm$^{-1}$ (7) Benzhydryl 7-[2-(2-aminothiazol-4-yl)-2-(3-thietanyloxyimino)acetamido]-3-[(Z)-2-(3-pyridyl)vinylthiomethyl]-3-cephem-4-carboxylate (syn isomer)

IR (Nujol): 1780, 1720, 1670, 1620, 1530 cm$^{-1}$ (8) 7-[2-(2-Aminothiazol-4-yl)-2-(3-thietanyloxyimino)acetamido]-3-[(Z)-2-(3-pyridyl)vinylthiomethyl]-3-cephem-4-carboxylic acid (syn isomer)

mp: 160° C. (dec.)

IR (Nujol): 1760, 1660, 1620, 1540 cm$^{-1}$ (9) Benzhydryl 7-[2-(2-cyclopenten-1-yl)oxyimino-2-(2-formamidothiazol-4-yl)acetamido]-3-[(Z)-2-(3-pyridyl)vinylthiomethyl]-3-cephem-4-carboxylate (syn isomer)

IR (Nujol): 1770, 1660, 1530 cm$^{-1}$

(10) 7-[2-(2-Cyclopenten-1-yl)oxyimino-2-(2-formamidothiazol-4-yl)acetamido]-3-[(Z)-2-(3-pyridyl)vinylthiomethyl]-3-cephem-4-carboxylic acid (syn isomer)

IR (Nujol): 1760, 1690, 1650, 1610, 1560, 1530 cm$^{-1}$

(11) 7-[2-(2-Aminothiazol-4-yl)-2-(2-cyclopenten-1-yl)oxyiminoacetamido]-3-[(Z)-2-(3-pyridyl)vinylthiomethyl]-3-cephem-4-carboxylic acid (syn isomer)

IR (Nujol): 1760, 1660, 1620, 1580, 1520 cm$^{-1}$

(12) Benzhydryl 7-[2-(2-cyclopenten-1-yl)oxyimino-2-(2-formamidothiazol-4-yl)acetamido]-3-[(Z)-2-cyanovinylthiomethyl]-3-cephem-4-carboxylate (syn isomer)

IR (Nujol): 2220, 1780, 1720, 1680 cm$^{-1}$

(13) 7-[2-(2-Cyclopenten-1-yl)oxyimino-2-(2-formamidothiazol-4-yl)acetamido]-3-[(Z)-2-cyanovinylthiomethyl]-3-cephem-4-carboxylic acid (syn isomer)

IR (Nujol): 3230, 2220, 1780, 1670 cm$^{-1}$

(14) 7-[2-(2-Aminothiazol-4-yl)-2-(2-cyclopenten-1-yl)oxyiminoacetamido]-3-[(Z)-2-cyanovinylthiomethyl]-3-cephem-4-carboxylic acid (syn isomer)

IR (Nujol): 3300, 2210, 1760, 1660 cm$^{-1}$

(15) p-Nitrobenzyl 7-[2-methoxyimino-2-{2-(2,2,2-trifluoroacetamido)thiazol-4-yl}acetamido]-3-vinylthiomethyl-3-cephem-4-carboxylate (syn isomer)

IR (Nujol): 1760, 1720, 1670, 1510, 1345, 1250, 1210 cm$^{-1}$

(16) p-Nitrobenzyl 7-(2-phenylacetamido)-3-vinylthiomethyl-3-cephem-4-carboxylate IR (Nujol): 3270, 1760, 1720, 1660 1525, 1350 cm$^{-1}$

(17) 7-[2-Carboxymethoxyimino-2-{2-(2,2,2-trifluoroacetamido)thiazol-4-yl}acetamido]-3-vinylthiomethyl-3-cephem-4-carboxylic acid (syn isomer)

IR (Nujol): 3250, 1770, 1720, 1655, 1580, 1540, 1270, 1210 cm$^{-1}$

(18) 7-[2-Carboxymethoxyimino-2-(2-aminothiazol-4-yl)acetamido]-3-vinylthiomethyl-3-cephem-4-carboxylic acid (syn isomer)

IR (Nujol): 1760, 1680–1620, 1580, 1240 cm$^{-1}$

(19) 7-[2-Allyloxyimino-2-(5-amino-1,2,4-thiadiazol-3-yl)acetamido]-3-[(Z)-2-(2-methyl-5-pyridyl)vinylthiomethyl]-3-cephem-4-carboxylic acid (syn isomer)

IR (Nujol): 3300, 3150, 1760, 1670, 1610, 1580, 1520 cm$^{-1}$

(20) Benzhydryl 7-[2-allyloxyimino-2-(5-amino-1,2,4-thiadiazol-3-yl)acetamido]-3-[(Z)-2-(2-methyl-5-pyridyl)vinylthiomethyl]-3-cephem-4-carboxylate (syn isomer)

IR (Nujol): 3300, 3150, 1780, 1720, 1680, 1610, 1530, 1490, 1300, 1240 cm$^{-1}$

(21) 7-[2-Allyloxyimino-2-(2-aminothiazol-4-yl)acetamido]-3-[(Z)-2-(2-methyl-5-pyridyl)vinylthiomethyl]-3-cephem-4-carboxylic acid (syn isomer)

IR (Nujol): 3300, 3150, 1760, 1670, 1610, 1580, 1520 cm$^{-1}$

(22) Benzhydryl 7-[2-allyloxyimino-2-(2-aminothiazol-4-yl)acetamido]-3-[(Z)-2-(2-methyl-5-pyridyl)vinylthiomethyl]-3-cephem-4-carboxylate (syn isomer)

IR (Nujol): 3300, 3150, 1780, 1720, 1670, 1610, 1530, 1300, 1240 cm$^{-1}$

(23) Benzhydryl 7-[2-allyloxyimino-2-(2-formamidothiazol-4-yl)acetamido]-3-[(Z)-2-(2-methyl-5-pyridyl)vinylthiomethyl]-3-cephem-4-carboxylate (syn isomer)

IR (Nujol): 3250, 3150, 1780, 1710, 1690, 1660, 1540, 1270, 1240 cm$^{-1}$

(24) Benzhydryl 7-[2-(5-amino-1,2,4-thiadiazol-3-yl)-2-ethoxyiminoacetamido]-3-[(Z)-2-(2-methyl-5-pyridyl)vinylthiomethyl]-3-cephem-4-carboxylate (syn isomer)

IR (Nujol): 1770, 1710, 1670, 1610, 1515 cm$^{-1}$

(25) 7-[2-(5-Amino-1,2,4-thiadiazol-3-yl)-2-ethoxyiminoacetamido]-3-[(Z)-2-(2-methyl-5-pyridyl)vinylthiomethyl]-3-cephem-4-carboxylic acid (syn isomer)

mp: 175° C. (dec.)

IR (Nujol): 1770, 1665, 1610, 1530 cm$^{-1}$

(26) Benzhydryl 7-[2-(5-amino-1,2,4-thiadiazol-3-yl)-2-ethoxyiminoacetamido]-3-[(Z)-2-cyanovinylthiomethyl]-3-cephem-4-carboxylate (syn isomer)

IR (Nujol): 2210, 1780, 1720, 1675, 1610 cm$^{-1}$

(27) 7-[2-(5-Amino-1,2,4-thiadiazol-3-yl)-2-ethoxyiminoacetamido]-3-[(Z)-2-cyanovinylthiomethyl]-3-cephem-4-carboxylic acid (syn isomer)

IR (Nujol): 3300, 2210, 1770, 1680, 1620 cm$^{-1}$

(28) Benzhydryl 7-[2-(2-formamidothiazol-4-yl)-2-methoxyiminoacetamido]-3-[(Z)-2-cyanovinylthiomethyl]-3-cephem-4-carboxylate (syn isomer)

IR (Nujol): 2210, 1780, 1710, 1680, 1660 cm$^{-1}$

(29) Benzhydryl 7-[2-(2-aminothiazol-4-yl)-2-methoxyiminoacetamido]-3-[(Z)-2-cyanovinylthiomethyl]-3-cephem-4-carboxylate (syn isomer)

IR (Nujol): 2210, 1770, 1715, 1670, 1610 cm$^{-1}$

(30) 7-[2-(2-Aminothiazol-4-yl)-2-methoxyiminoacetamido]-3-[(Z)-2-cyanovinylthiomethyl]-3-cephem-4-carboxylic acid (syn isomer)

IR (Nujol): 3300, 2220, 1775, 1670 cm$^{-1}$

(31) Benzhydryl 7-[2-allyloxyimino-2-(2-formamidothiazol-4-yl)acetamido]-3-[(Z)-2-cyanovinylthiomethyl]-3-cephem-4-carboxylate (syn isomer)

IR (Nujol): 2210, 1780, 1715, 1680 cm$^{-1}$

(32) Benzhydryl 7-[2-allyloxyimino-2-(2-aminothiazol-4-yl)acetamido]-3-[(Z)-2-cyanovinylthiomethyl]-3-cephem-4-carboxylate (syn isomer)

IR (Nujol): 2210, 1770, 1715, 1665, 1610 cm$^{-1}$

(33) 7-[2-Allyloxyimino-2-(2-aminothiazol-4-yl)acetamido]-3-[(Z)-2-cyanovinylthiomethyl]-3-cephem-4-carboxylic acid (syn isomer)

IR (Nujol): 3300, 2220, 1770, 1670, 1620 cm$^{-1}$

(34) Benzhydryl 7-[2-(5-amino-1,2,4-thiadiazol-3-yl)-2-methoxyiminoacetamido]-3-[(Z)-2-cyanovinylthiomethyl]-3-cephem-4-carboxylate (syn isomer)

IR (Nujol): 2210, 1770, 1715, 1670, 1610 cm$^{-1}$

(35) 7-[2-(5-Amino-1,2,4-thiadiazol-3-yl)-2-methoxyiminoacetamido]-3-[(Z)-2-cyanovinylthiomethyl]-3-cephem-4-carboxylic acid (syn isomer)

IR (Nujol): 3300, 2210, 1770, 1670, 1620 cm$^{-1}$

(36) Benzhydryl 7-[2-((Z)-2-cyanovinylthio)acetamido]-3-[(Z)-2-cyanovinylthiomethyl]-3-cephem-4-carboxylate IR (Nujol): 2210, 1780, 1715, 1665 cm$^{-1}$

(37) 7-[2-((Z)-2-Cyanovinylthio)acetamido]-3-[(Z)-2-cyanovinylthiomethyl]-3-cephem-4-carboxylic acid IR (Nujol): 3300, 2210, 1775, 1710, 1670 cm$^{-1}$

(38) Benzhydryl 7-[2-(5-amino-1,2,4-thiadiazol-3-yl)-2-ethoxyiminoacetamido]-3-[(E)-2-cyanovinylthiomethyl]-3-cephem-4-carboxylate (syn isomer)

IR (Nujol): 2210, 1780, 1720, 1680 cm$^{-1}$

(39) 7-[2-(5-Amino-1,2,4-thiadiazol-3-yl)-2-ethoxyiminoacetamido]-3-[(E)-2-cyanovinylthiomethyl]-3-cephem-4-carboxylic acid (syn isomer)

IR (Nujol): 3300, 2220, 1780, 1675, 1620 cm$^{-1}$

(40) Benzhydryl 7-[2-(2-formamidothiazol-4-yl)-2-methoxyiminoacetamido]-3-[(E)-2-cyanovinylthiomethyl]-3-cephem-4-carboxylate (syn isomer)

IR (Nujol): 2210, 1780, 1715, 1680 cm$^{-1}$

(41) Benzhydryl 7-[2-(2-aminothiazol-4-yl)-2-methoxyiminoacetamido]-3-[(E)-2-cyanovinylthiomethyl]-3-cephem-4-carboxylate (syn isomer)

IR (Nujol): 2220, 1780, 1720, 1675, 1615 cm$^{-1}$

(42) 7-[2-(2-Aminothiazol-4-yl)-2-methoxyiminoacetamido]-3-[(E)-2-cyanovinylthiomethyl]-3-cephem-4-carboxylic acid (syn isomer)

IR (Nujol): 3300, 2210, 1765, 1665, 1620 cm$^{-1}$

(43) Benzhydryl 7-[2-allyloxyimino-2-(2-formamidothiazol-4-yl)acetamido]-3-[(E)-2-cyanovinylthiomethyl]-3-cephem-4-carboxylate (syn isomer)

IR (Nujol): 2220, 1780, 1720, 1680 cm$^{-1}$

(44) Benzhydryl 7-[2-allyloxyimino-2-(2-aminothiazol-4-yl)acetamido]-3-[(E)-2-cyanovinylthiomethyl]-3-cephem-4-carboxylate (syn isomer)

IR (Nujol): 2220, 1780, 1720, 1670, 1615 cm$^{-1}$

(45) 7-[2-Allyloxyimino-2-(2-aminothiazol-4-yl)acetamido]-3-[(E)-2-cyanovinylthiomethyl]-3-cephem-4-carboxylic acid (syn isomer)

IR (Nujol): 2200, 1765, 1660 cm$^{-1}$

(46) Benzhydryl 7-[2-allyloxyimino-2-(5-amino-1,2,4-thiadiazol-3-yl)acetamido]-3-[(E)-2-cyanovinylthiomethyl]-3-cephem-4-carboxylate (syn isomer)

IR (Nujol): 2210, 1770, 1720, 1670, 1610 cm$^{-1}$

(47) 7-[2-Allyloxyimino-2-(5-amino-1,2,4-thiadiazol-3-yl)acetamido]-3-[(E)-2-cyanovinylthiomethyl]-3-cephem-4-carboxylic acid (syn isomer)

IR (Nujol): 3300, 2220, 1770, 1675, 1620 cm$^{-1}$

EXAMPLE 26 p-Nitrobenzyl 7-[2-methoxyimino-2-{2-(2,2,2-trifluoroacetamido)thiazol-4-yl}acetamido]-3-vinylthiomethyl-3-cephem-4-carboxylate (syn isomer) (100 mg) was hydrogenated in the presence of 5% palladium on carbon under an atmospheric pressure of hydrogen in a mixture of tetrahydrofuran (6 ml), ethanol (0.6 ml) and 0.025M phosphate buffer solution (pH 6.85, 6.4 ml) at ambient temperature for 1.5 hours. The catalyst was filtered off and washed with ethyl acetate and a saturated aqueous solution of sodium bicarbonate successively. The filtrate and washings were combined and adjusted to pH 8 with diluted hydrochloric acid. The aqueous layer was separated, adjusted to pH 6 with diluted hydrochloric acid, washed with ethyl acetate, adjusted to pH 2.4 with diluted hydrochloric acid and extracted with ethyl acetate. The extract was washed with a saturated aqueous solution of sodium chloride, dried over magnesium sulfate, concentrated in vacuo and triturated with diethyl ether to give 7-[2-methoxyimino-2-{2-(2,2,2-trifluoroacetamido)thiazol-4-yl}acetamido]-3-vinylthiomethyl-3-cephem-4-carboxylic acid (syn isomer) (30.0 mg).

IR (Nujol): 3200, 1770, 1710, 1650, 1580, 1500, 1250, 1200 cm$^{-1}$

NMR (DMSO-d$_6$, δ): 3.5–4.0 (4H, m), 4.92 (3H, s), 5.16 (1H, d, J=17 Hz), 5.18 (1H, d, J=5 Hz), 5.20 (1H, d, J=10 Hz), 4.75 (1H, dd, J=5 Hz) and 8 Hz), 6.52 (1H, dd, J=10 Hz and 17 Hz), 7.53 (1H, s), 9.72 (1H, d, J=8 Hz)

EXAMPLE 27

Benzhydryl 7-[2-(2-formamidothiazol-4-yl)-2-isopropoxyiminoacetamido]-3-[(Z)-2-(1-methyl-3-pyridinio)vinylthiomethyl]-3-cephem-4-carboxylate nitrate (8.25 g) was added to a mixed solution of concentrated hydrochloric acid (2.9 ml) and methanol (215 ml). The mixture was stirred at 30° C. for several hours and poured into a mixture of tetrahydrofuran and an aqueous solution of sodium chloride. The organic layer was separated, washed with a saturated aqueous solution of sodium chloride, dried over magnesium sulfate and triturated with diethyl ether to give a powder (5.18 g), which was collected by filtration. To a solution of the powder (1.38 g) in a mixture of anisole (1.3 ml) and methylene chloride (4 ml) was added trifluoroacetic acid (2.6 ml) at 0° C. The mixture was stirred for an hour at the same temperature and dropped into diethyl ether. The resultant precipitate was collected by filtration and washed with diethyl ether. The precipitate was dissolved in water at pH 6.4 (adjusted with sodium bicarbonate) and the aqueous solution was subjected to column chromatography on macroporous non-ionic adsorption resin "Diaion HP 20" (26 ml). The elution was carried out with 20% aqueous isopropyl alcohol. The eluates containing the object compound were collected, evaporated to remove isopropyl alcohol under reduced pressure and lyophilized to give a powder (300 mg). The powder was dissolved in a mixture of concentrated hydrochloric acid (0.1 ml), methanol (10 ml) and tetrahydrofuran (5 ml) and the mixture was stirred at 30° C. for half an hour. The reaction mixture was poured into water and adjusted to pH 6.4 with sodium bicarbonate. The aqueous solution was subjected to column chromatography on macroporous non-ionic adsorption resin "Diaion HP 20". The elution was carried out with 20% aqueous isopropyl alcohol. The eluates containing the object compound were collected, evaporated to remove isopropyl alcohol under reduced pressure and lyophilized to give 7-[2-(2-aminothiazol-4-yl)-2-isopropoxyiminoacetamido]-3-[(Z)-2-(1-methyl-3-pyridinio)vinylthiomethyl]-3-cephem-4-carboxylate (syn isomer) (170 mg).

mp: 145° C. (dec.)

IR (Nujol): 1770, 1670, 1600 cm$^{-1}$

NMR (DMSO-d$_6$, δ): 1.18 (6H, d, J=6 Hz), 4.0–4.5 (5H, m), 4.98 (1H, d, J=5 Hz), 5.53 (1H, dd, J=5 Hz, 8 Hz), 6.5, 7.9 (2H, ABq, J=12 Hz), 6.65 (1H, s), 7.13 (2H, s), 8.05 (1H, dd, J=5 Hz, 8 Hz), 8.53 (1H, d, J=8 Hz), 8.7 (1H, d, J=5 Hz), 9.0 (1H, s), 9.33 (1H, d, J=8 Hz)

EXAMPLE 28

The following compounds were obtained according to similar manners to those of Examples 3–7 and 26.

(1) 7-[2-(2-Aminothiazol-4-yl)-2-(3-thietanyloxyimino)acetamido]-3-[(Z)-2-(3-pyridyl)vinylthiomethyl]-3-cephem-4-carboxylic acid (anti isomer)

mp: 150° C. (dec.)

IR (Nujol): 1780, 1660, 1520 cm$^{-1}$ (2) 7-[2-(2-Aminothiazol-4-yl)-2-methoxyiminoacetamido]-3-vinylthiomethyl-3-cephem-4-carboxylic acid hydrochloride (syn isomer)

mp: 195°–205° C. (dec.)

IR (Nujol): 1760, 1650, 1580, 1520 cm$^{-1}$ (3) 7-[2-(5-Amino-1,2,4-thiadiazol-3-yl)-2-ethoxyiminoacetamido]-3-(2-trimethylsilylethynylthiomethyl)-3-cephem-4-carboxylic acid (syn isomer)

mp: 123° C. (dec.)

IR (Nujol): 3300, 3190, 2080, 1765, 1670, 1615, 1515 cm$^{-1}$ (4) 7-[2-(2-Aminothiazol-4-yl)-2-(3-thietanyloxyimino)acetamido]-3-[(Z)-2-(3-pyridyl)vinylthiomethyl]-3-cephem-4-carboxylic acid (syn isomer)

mp: 160° C. (dec.)

IR (Nujol): 1760, 1660, 1620, 1540 cm$^{-1}$

NMR (DMSO-d$_6$, δ): 3.0–4.3 (6H, m), 5.1–5.3 (2H, m), 5.75 (1H, dd, J=5 Hz, 8 Hz), 6.47, 6.77 (2H, ABq, J=12 Hz), 6.75 (1H, s), 7.20 (2H, broad s), 7.35 (1H, dd, J=5 Hz, 8 Hz), 7.80 (1H, m), 9.57 (1H, d, J=8 Hz)

(5) 7-[2-(2-Cyclopenten-1-yl)oxyimino-2-(2-formamidothiazol-4-yl)acetamido]-3-[(Z)-2-(3-pyridyl)vinylthiomethyl]-3-cephem-4-carboxylic acid (syn isomer)

IR (Nujol): 1760, 1690, 1650, 1610, 1560, 1530 cm$^{-1}$

NMR (DMSO-d$_6$, δ): 1.70–2.40 (4H, m), 3.60 (2H, s), 3.90, 4.17 (2H, ABq, J=12 Hz), 5.10–5.40 (2H, m), 5.60–6.2 (3H, m), 6.50, 6.85 (2H, ABq, J=10 Hz), 7.35 (1H, s), 7.52 (1H, dd, J=5 Hz, 8 Hz), 7.97 (1H, dt, J=2 Hz, 8 Hz), 8.4–8.6 (2H, m), 8.65 (1H, d, J=2 Hz), 9.57 (1H, d, J=8 Hz)

(6) 7-[2-(2-Aminothiazol-4-yl)-2-(2-cyclopenten-1-yl)oxyiminoacetamido]-3-[(Z)-2-(3-pyridyl)vinylthiomethyl]-3-cephem-4-carboxylic acid (syn isomer)

IR (Nujol): 1760, 1660, 1620, 1580, 1520 cm$^{-1}$ (7) 7-[2-(2-Cyclopenten-1-yl)oxyimino-2-(2-formamidothiazol-4-yl)acetamido]-3-[(Z)-2-cyanovinylthiomethyl]-3-cephem-4-carboxylic acid (syn isomer)

IR (Nujol): 3230, 2220, 1780, 1670 cm$^{-1}$

NMR (DMSO-d$_6$, δ): 1.9–2.4 (4H, m), 3.6 (2H, broad s), 3.77 and 4.23 (2H, ABq, J=14 Hz), 5.17 (1H, d, J=5 Hz), 5.2–6.2 (4H, m), 5.7 (1H, d, J=11 Hz), 7.34 (1H, s), 7.73 (1H, d, J=11 Hz), 8.5 (1H, s), 9.60 (1H, d, J=8 Hz)

(8) 7-[2-(2-Aminothiazol-4-yl)-2-(2-cyclopenten-1-yl)oxyiminoacetamido]-3-[(Z)-2-cyanovinylthiomethyl]-3-cephem-4-carboxylic acid (syn isomer)

IR (Nujol): 3300, 2210, 1760, 1660 cm$^{-1}$ (9) 7-[2-Carboxymethoxyimino-2-{2-(2,2,2-trifluoroacetamido)thiazol-4-yl}acetamido]-3-vinylthiomethyl-3-cephem-4-carboxylic acid (syn isomer)

IR (Nujol): 3250, 1770, 1720, 1655, 1580, 1540, 1270, 1210 cm$^{-1}$

(10) 7-[2-Carboxymethoxyimino-2-(2-aminothiazol-4-yl)acetamido]-3-vinylthiomethyl-3-cephem-4-carboxylic acid (syn isomer)

IR (Nujol): 1760, 1680–1620, 1580, 1240 cm$^{-1}$

(11) 7-[2-Allyloxyimino-2-(5-amino-1,2,4-thiadiazol-3-yl)acetamido]-3-[(Z)-2-(2-methyl-5-pyridyl)vinylthiomethyl]-3-cephem-4-carboxylic acid (syn isomer)

mp: 161°–166° C. (dec.).

IR (Nujol): 3300, 3150, 1760, 1670, 1610, 1580, 1520 cm$^{-1}$

NMR (DMSO-d$_6$, δ): 2.59 (3H, s), 3.62 (2H, broad s), 3.80 and 4.20 (2H, ABq, J=14 Hz), 4.6–4.8 (2H, m), 5.0–5.5 (3H, m), 5.18 (1H, d, J=5 Hz), 5.82 (1H, dd, J=5 Hz and 8 Hz), 6.49 (1H, d, J=11 Hz), 6.79 (1H, d, J=11 Hz), 7.3–7.5 (1H, m), 7.7–8.0 (1H, m), 8.10 (2H, broad s), 8.4–8.5 (1H, m), 8.57 (1H, d, J=8 Hz)

(12) 7-[2-Allyloxyimino-2-(2-aminothiazol-4-yl)acetamido]-3-[(Z)-2-(2-methyl-5-pyridyl)vinylthiomethyl]-3-cephem-4-carboxylic acid (syn isomer)

mp: 157°–163° C. (dec.)

IR (Nujol): 3300, 3150, 1760, 1670, 1610, 1580, 1520 cm$^{-1}$

NMR (DMSO-d$_6$, δ): 2.59 (3H, s), 3.62 (2H, broad s), 3.80 and 4.20 (2H, ABq, J=14 Hz), 4.6–4.8 (2H, m), 5.0–5.5 (3H, m), 5.18 (1H, d, J=5 Hz), 5.82 (1H, dd, J=5 Hz and 8 Hz), 6.49 (1H, d, J=11 Hz), 6.79 (1H, d, J=11 Hz), 7.3–7.5 (1H, m), 7.7–8.0 (1H, m), 8.10 (2H, broad s), 8.4–8.5 (1H, m), 8.57 (1H, d, J=8 Hz)

(13) 7-[2-(5-Amino-1,2,4-thiadiazol-3-yl)-2-ethoxyiminoacetamido]-3-[(Z)-2-(2-methyl-5-pyridyl)vinylthiomethyl]-3-cephem-4-carboxylic acid (syn isomer)

mp: 175° C. (dec.)

IR (Nujol): 1770, 1665, 1610, 1530 cm$^{-1}$

NMR (DMSO-d$_6$, δ): 1.23 (3H, t, J=7 Hz), 2.43–2.63 (3H, s, hidden), 3.63 (2H, broad s), 3.77 and 4.17 (2H, ABq, J=14 Hz), 4.20 (2H, q, J=7 Hz), 5.30 (1H, d, J=5 Hz), 5.80 (1H, dd, J=5 Hz, 8 Hz), 6.43 and 6.73 (2H, ABq, J=11 Hz), 7.30 (1H, d, J=8 Hz), 7.83 (1H, dd, J=3 Hz, 8 Hz), 8.07 (2H, broad s), 8.50 (1H, d, J=3 Hz) and 9.50 (1H, d, J=8 Hz)

(14) 7-[2-(5-Amino-1,2,4-thiadiazol-3-yl)-2-ethoxyiminoacetamido]-3-[(Z)-2-cyanovinylthiomethyl]-3-cephem-4-carboxylic acid (syn isomer)

IR (Nujol): 3300, 2210, 1770, 1680, 1620 cm$^{-1}$

NMR (DMSO-d$_6$, δ): 1.23 (3H, t, J=7 Hz), 3.6 (2H, broad s), 3.9–4.12 (2H, m), 4.2 (2H, q, J=7 Hz), 5.2 (1H, d, J=5 Hz), 5.7 (1H, d, J=11 Hz), 5.8 (1H, dd, J=8 Hz, 5 Hz), 7.75 (1H, d, J=11 Hz), 8.10 (2H, broad s), 9.53 (1H, d, J=8 Hz)

(15) 7-[2-(2-Aminothiazol-4-yl)-2-methoxyiminoacetamido]-3-[(Z)-2-cyanovinylthiomethyl]-3-cephem-4-carboxylic acid (syn isomer)

IR (Nujol): 3300, 2220, 1775, 1670 cm$^{-1}$

NMR (DMSO-d$_6$, δ): 3.5 (2H, broad s), 3.73 (3H, s), 3.6–4.3 (2H, m), 5.1 (1H, d, J=5 Hz), 5.63 (1H, d, J=11 Hz), 5.7 (1H, dd, J=8 Hz, 5 Hz), 6.63 (1H, s), 7.65 (1H, d, J=11 Hz), 9.50 (1H, d, J=8 Hz)

(16) 7-[2-Allyloxyimino-2-(2-aminothiazol-4-yl)acetamido]-3-[(Z)-2-cyanovinylthiomethyl]-3-cephem-4-carboxylic acid (syn isomer)

IR (Nujol): 3300, 2220, 1770, 1670, 1620 cm$^{-1}$

NMR (DMSO-d$_6$, δ): 3.53 (2H, broad s), 3.6 and 4.2 (2H, ABq, J=13 Hz), 4.57 (2H, d, J=5 Hz), 5.1–6.2 (4H, m), 5.17 (1H, d, J=5 Hz), 5.67 (1H, d, J=11 Hz), 6.7 (1H, s), 7.7 (1H, d, J=11 Hz), 9.60 (1H, d, J=8 Hz)

(17) 7-[2-(5-Amino-1,2,4-thiadiazol-3-yl)-2-methoxyiminoacetamido]-3-[(Z)-2-cyanovinylthiomethyl]-3-cephem-4-carboxylic acid (syn isomer)

IR (Nujol): 3300, 2210, 1770, 1670, 1620 cm$^{-1}$

NMR (DMSO-d$_6$, δ): 3.6 (2H, broad s), 4.8 and 4.23 (2H, ABq, J=13 Hz), 4.9 (3H, s), 5.17 (1H, d, J=5 Hz), 5.7 (1H, d, J=11 Hz), 5.8 (1H, dd, J=8 Hz, 5 Hz), 7.75 (1H, d, J=11 Hz), 8.1 (2H, broad s), 9.57 (1H, d, J=8 Hz)

(18) 7-[2-((Z)-2-Cyanovinylthio)acetamido]-3-[(Z)-2-cyanovinylthiomethyl]-3-cephem-4-carboxylic acid IR (Nujol): 3300, 2210, 1775, 1710, 1670 cm$^{-1}$ NMR (DMSO-d$_6$, δ): 3.62 (2H, m), 3.71 (2H, s), 3.82 and 4.28 (2H, ABq, J=13 Hz), 5.17 (1H, d, J=5 Hz), 5.71 (2H, d, J=10 Hz), 5.74 (1H, dd, J=8 Hz, 5 Hz), 7.67 (1H, d, J=10 Hz), 7.80 (1H, d, J=10 Hz), 9.32 (1H, d, J=8 Hz)

(19) 7-[2-(5-Amino-1,2,4-thiadiazol-3-yl)-2-ethoxyiminoacetamido]-3-[(E)-2-cyanovinylthiomethyl]-3-cephem-4-carboxylic acid (syn isomer)

IR (Nujol): 3300, 2220, 1780, 1675, 1620 cm$^{-1}$

NMR (DMSO-d$_6$, δ): 1.27 (3H, t, J=7 Hz), 3.6 (2H, broad s), 3.83–4.2 (2H, m), 4.2 (2H, q, J=7 Hz), 5.2 (1H, d, J=5 Hz), 5.73 (1H, d, J=15 Hz), 5.83 (1H, dd, J=8 Hz, 5 Hz), 7.90 (1H, d, J=15 Hz), 8.12 (2H, broad s), 9.60 (1H, d, J=8 Hz)

(20) 7-[2-(2-Aminothiazol-4-yl)-2-methoxyiminoacetamido]-3-[(E)-2-cyanovinylthiomethyl]-3-cephem-4-carboxylic acid (syn isomer)

IR (Nujol): 3300, 2210, 1765, 1665, 1620 cm$^{-1}$

NMR (DMSO-d$_6$, δ): 3.5–3.75 (2H, m), 3.75–4.2 (2H, m), 3.88 (2H, s), 5.20 (1H, d, J=5 Hz), 5.78 (1H, d, J=15 Hz), 5.80 (1H, dd, J=8 Hz, 5 Hz), 7.92 (1H, d, J=15 Hz), 9.67 (1H, d, J=8 Hz)

(21) 7-[2-Allyloxyimino-2-(2-aminothiazol-4-yl)acetamido]-3-[(E)-2-cyanovinylthiomethyl]-3-cephem-4-carboxylic acid (syn isomer)

IR (Nujol): 2200, 1765, 1660 cm$^{-1}$

NMR (DMSO-d$_6$, δ): 3.67 (2H, broad s), 3.87 and 4.2 (2H, ABq, J=14 Hz), 4.65 (2H, d, J=5 Hz), 5.15–6.2 (4H, m), 5.23 (1H, d, J=5 Hz), 5.77 (1H, d, J=16 Hz), 6.8 (1H, s), 7.9 (1H, d, J=16 Hz), 9.67 (1H, d, J=8 Hz)

(22) 7-[2-Allyloxyimino-2-(5-amino-1,2,4-thiadiazol-3-yl)acetamido]-3-[(E)-2-cyanovinylthiomethyl]-3-cephem-4-carboxylic acid (syn isomer)

IR (Nujol): 3300, 2220, 1770, 1675, 1620 cm$^{-1}$

NMR (DMSO-d$_6$, δ): 3.35–4.33 (4H, m), 4.69 (2H, d, J=5 Hz), 5.15–6.2 (4H, m), 5.22 (1H, d, J=5 Hz), 5.75 (1H, d, J=15 Hz), 7.91 (1H, d, J=15 Hz), 8.15 (2H, broad s), 9.67 (1H, d, J=8 Hz)

(23) 7-Amino-2-[(Z)-2-(3-pyridyl)vinylthiomethyl]-3-cephem-4-carboxylic acid

IR (Nujol): 1780, 1620 cm$^{-1}$

NMR (DMSO-d$_6$, δ): 3.3–4.3 (4H, m), 4.85 (1H, d, J=5 Hz), 5.07 (1H, d, J=5 Hz), 6.50, 6.80 (2H, ABq, J=12 Hz), 7.2–7.5 (1H, m), 7.6–7.9 (1H, m), 8.2–8.8 (2H, m)

EXAMPLE 29

To a solution of 3-[(Z)-2-(tritylthio)vinyl]-1-methylpyridinium iodide (10 g) in methanol (400 ml) was added a solution of silver nitrate (7.2 g) in a mixture of water (20 ml) and pyridine (2 ml) under ice-cooling with stirring. The mixture was stirred for an hour and poured into diethyl ether to give a precipitate. The precipitate was collected and dried in vacuo to give crude [(Z)-2-(1-methyl-3-pyridinio)vinylthio]silver nitrate (10 g). A mixture of crude [(Z)-2-(1-methyl-3-pyridinio)vinylthio]silver nitrate (0.8 g) and sodium iodide (2.67 g) in a mixture of N,N-dimethylformamide (15 ml) and acetonitrile (5 ml) was stirred at ambient temperature for 20 minutes. To the reaction mixture was added benzhydryl 7-[2-(2-formamidothiazol-4-yl)-2-isopropoxyiminoacetamido]-3-chloromethyl-3-cephem-4-carboxylate (0.65 g) under ice-cooling. The mixture was stirred at the same temperature for 3 hours and at ambient temperature for an hour. The mixture was filtered and the filtrate was poured into a saturated aqueous solution of sodium chloride. The aqueous mixture was washed with diethyl ether and extracted with tetrahydrofuran. The extract was washed with a saturated aqueous solution of sodium chloride, dried over magnesium sulfate, concentrated in vacuo and triturated with diethyl ether to give benzhydryl 7-[2-(2-formamidothiazol-4-yl)-2-isopropoxyiminoacetamido]-3-[(Z)-2-(1-methyl-3-pyridinio)vinylthiomethyl]-3-cephem-4-carboxylate nitrate (syn isomer) (670 mg).

IR (Nujol): 1780, 1720, 1670, 1540 cm−1

NMR (DMSO-d$_6$, δ): 1.25 (6H, d, J=6 Hz), 3.45–4.1 (4H, m), 4.33 (3H, s), 5.28 (1H, d, J=5 Hz), 5.93 (1H, dd, J=5 Hz, 8 Hz), 6.50, 7.0 (2H, ABq, J=12 Hz), 6.93 (1H, s), 7.2–7.6 (11H, m), 8.08 (1H, dd, J=5 Hz, 8 Hz), 8.3–8.6 (2H, m), 8.75 (1H, d, J=8 Hz), 8.88 (1H, s), 9.57 (1H, d, J=8 Hz)

EXAMPLE 30

To a solution of 7-[2-(5-amino-1,2,4-thiadiazol-3-yl)-2-ethoxyiminoacetamido]-3-acetoxymethyl-3-cephem-4-carboxylic acid (syn isomer) (10 g) and trimethylsilyl chloride (5.95 g) in tetrahydrofuran (200 ml) was added triethylamine (6.23 ml) under ice-cooling. After the mixture was stirred at ambient temperature for 2 hours. The precipitate was filtered off and washed with dry tetrahydrofuran. The filtrate and the washings were combined and concentrated in vacuo. The residue was dissolved in acetonitrile (100 ml), and to the solution was added trimethylsilyl iodide (5.7 ml) at ambient temperature. The mixture was stirred for 30 minutes and concentrated in vacuo to give a residue (A). On the other hand, to a solution of trimethylsilylacetylene (5.7 ml) in tetrahydrofuran (70 ml) was added 1.55N n-butyllithium in n-hexane (20.6 ml) at −60° C.

The mixture was allowed to warm to −25° C. Sulfur (1.15 g) was added to the mixture at once at −25° C. The mixture was stirred for 30 minutes under ice-cooling, allowed to warm to 15° C. and added to a solution of the residue (A) in tetrahydrofuran (150 ml) at −40° C. The mixture was allowed to warm to 0° C. and poured into a mixture of ice-water and ethyl acetate and the mixture was adjusted to pH 7.5 with a saturated aqueous solution of sodium bicarbonate. The separated aqueous layer was adjusted to pH 2 with diluted hydrochloric acid and extracted with ethyl acetate. The extract was washed with a saturated aqueous solution of sodium chloride, dried over magnesium sulfate, concentrated in vacuo and triturated with diisopropyl ether to give 7-[2-(5-amino-1,2,4-thiadiazol-3-yl)-2-ethoxyiminoacetamido]-3-(2-trimethylsilylethynylthiomethyl)-3-cephem-4-carboxylic acid (syn isomer) (6.67 g).

mp: 123° C. (dec.)

IR (Nujol): 3300, 3190, 2080, 1765, 1670, 1615, 1515 cm$^{-1}$

NMR (DMSO-d$_6$, δ): 1.27 (3H, t, J=8 Hz), 3.67 (2H, broad s), 3.73, 4.13 (2H, ABq, J=14 Hz), 4.20 (2H, q, J=8 Hz), 5.14 (1H, d, J=5 Hz), 5.80 (1H, dd, J=5 Hz, 8 Hz), 8.07 (2H, broad s), 9.53 (1H, d, J=8 Hz)

EXAMPLE 31

The following compounds were obtained according to similar manners to those of Examples 9–12, 14 and 29.

(1) p-Nitrobenzyl 7-[2-(p-nitrobenzyloxycarbonylmethoxyimino)-2-{2-(2,2,2-trifluoroacetamido)thiazol-4-yl}acetamido]-3-vinylthiomethyl-3-cephem-4-carboxylate (syn isomer)

IR (Nujol): 1760, 1730, 1680, 1605, 1580, 1520, 1350, 1260, 1210 cm$^{-1}$ (2) 7-[2-(2-Aminothiazol-4-yl)-2-(3-thietanyloxyimino)acetamido]-3-[(Z)-2-(3-pyridyl)vinylthiomethyl]-3-cephem-4-carboxylic acid (anti isomer)

mp: 150° C. (dec.)

IR (Nujol): 1780, 1660, 1520 cm$^{-1}$ (3) 7-[2-(2-Aminothiazol-4-yl)-2-isopropoxyimino acetamido]-3-[(Z)-2-(1-methyl-3-pyridinio)vinylthiomethyl]-3-cephem-4-carboxylate (syn isomer)

mp: 145° C. (dec.)

IR (Nujol): 1770, 1670, 1600 cm$^{-1}$ (4) 7-[2-Methoxyimino-2-{2-(2,2,2-trifluoroacetamido)thiazol-4yl}acetamido]-3-vinylthiomethyl-3-cephem-4-carboxylic acid (syn isomer) IR (Nujol): 3200, 1770, 1710, 1650, 1580, 1500, 1250, 1200 cm$^{-1}$ (5) 7-[2-(2-Aminothiazol-4-yl)-2-methoxyiminoacetamido]-3-vinylthiomethyl-3-cephem-4-carboxylic acid hydrochloride (syn isomer)

mp: 195°–205° C. (dec.)

IR (Nujol): 1760, 1650, 1580, 1520 cm$^{-1}$ (6) Benzhydryl 7-[2-(2-formamidothiazol-4yl)-2-(3-thietanyloxyimino)acetamido]-3-[(Z)-2-(3-pyridyl)-vinylthiomethyl]-3-cephem-4-carboxylate (syn isomer)

IR (Nujol): 1770, 1660, 1240, 1160 cm$^{-1}$

NMR (DMSO-d$_6$, δ): 3.3–4.0 (6H, m), 5.1–5.4 (2H, m), 5.93 (1H, dd, J=5 Hz, 8 Hz), 6.35, 6.53 (2H, ABq, J=12 Hz), 6.97 (1H, s), 7.10–7.60 (11H, m), 7.77 (2H, m), 8.37 (1H, dd, J=2 Hz, 5 Hz), 8.48 (1H, s), 8.55 (1H, d, J=2 Hz), 9.70 (1H, d, J=8 Hz)

(7) Benzhydryl 7-[2-(2-aminothiazol-4yl)-2-(3-thietanyloxyimino)acetamido]-3-[(Z)-2-(3-pyridyl)-vinylthiomethyl]-3-cephem-4-carboxylate (syn isomer)

IR (Nujol): 1780, 1720, 1670, 1620, 1530 cm$^{-1}$ (8) 7-[2-(2-Aminothiazol-4-yl)-2-(3-thietanyloxyimino)acetamido]-3-[(Z)-2-(3-pyridyl)vinylthiomethyl]-3-cephem-4-carboxylic acid (syn isomer)

mp: 160° C. (dec.)

IR (Nujol): 1760, 1660, 1620, 1540 cm$^{-1}$ (9) Benzhydryl 7-[2-(2-cyclopenten-1-yl)oxyimino-2-(2-formamidothiazol-4-yl)acetamido]-3-[(Z)-2-(3-pyridyl)vinylthiomethyl]-3-cephem-4-carboxylate (syn isomer)

IR (Nujol): 1770, 1660, 1530 cm$^{-1}$

NMR (DMSO-d$_6$, δ): 1.70–2.40 (4H, m), 3.5–4.3 (4H, m), 5.3–5.5 (2H, m), 5.7–6.4 (3H, m), 6.6 (2H, m), 7.03 (1H, s), 7.2–7.67 (11H, m), 7.7–8.0 (1H, m), 8.3–8.8 (3H, m), 9.75 (1H, d, J=8 Hz)

(10) 7-[2-(2-Cyclopenten-1-yl)oxyimino-2-(2-formamidothiazol-4-yl)acetamido]-3-[(Z)-2-(3-pyridyl)vinylthiomethyl]-3-cephem-4-carboxylic acid (syn isomer)

IR (Nujol): 1760, 1690, 1650, 1610, 1560, 1530 cm$^{-1}$

(11) 7-[2-(2-Aminothiazol-4-yl)-2-(2-cyclopenten-1-yl)oxyiminoacetamido]-3-[(Z)-2-(3-pyridyl)vinylthiomethyl]-3-cephem-4-carboxylic acid (syn isomer)

IR (Nujol): 1760, 1660, 1620, 1580, 1520 cm$^{-1}$

(12) Benzhydryl 7-[2-(2-cyclopenten-1-yl)oxyimino-2-(2-formamidothiazol-4yl)acetamido]-3-[(Z)-2-cyanovinylthiomethyl]-3-cephem-4-carboxylate (syn isomer)

IR (Nujol): 2220, 1780, 1720, 1680 cm$^{-1}$

NMR (DMSO-d$_6$, δ): 1.8–2.4 (4H, m), 3.6 (2H, broad s), 3.95 (2H, broad s), 5.23–6.2 (5H, m), 5.65 (1H, d, J=11 Hz), 7.0 (1H, s), 7.3–7.68 (12H, m), 8.6 (1H, s), 9.72 (1H, d, J=8 Hz)

(13) 7-[2-(2-Cyclopenten-1-yl)oxyimino-2-(2-formamidothiazol-4-yl)acetamido]-3-[(Z)-2-cyanovinylthiomethyl]-3-cephem-4-carboxylic acid (syn isomer)

IR (Nujol): 3230, 2220, 1780, 1670 cm$^{-1}$

(14) 7-[2-(2-Aminothiazol-4-yl)-2-(2-cyclopenten-1-yl)oxyiminoacetamido]-3-[(Z)-2-cyanovinylthiomethyl]-3-cephem-4-carboxylic acid (syn isomer) IR (Nujol): 3300, 2210, 1760, 1660 cm$^{-1}$

(15) p-Nitrobenzyl 7-[2-methoxyimino-2-{2-(2,2,2-trifluoroacetamido)thiazol-4-yl}acetamido]-3-vinylthiomethyl-3-cephem-4-carboxylate (syn isomer)

IR (Nujol): 1760, 1720, 1670, 1510, 1345, 1250, 1210 cm$^{-1}$

NMR (DMSO-d$_6$, δ): 3.65 (2H, broad s), 3.70 and 3.94 (2H, ABq, J=14 Hz), 3.92 (3H, s), 5.10 (1H, d, J=5 Hz), 5.32 (1H, d, J=17 Hz), 5.33 (1H, d, J=10 Hz), 5.42 (2H, s), 5.86 (1H, dd, J=5 Hz and 8 Hz), 6.46 (1H, dd, J=10 Hz and 17 Hz), 7.52 (1H, s), 7.68 (2H, d, J=8 Hz), 8.26 (2H, d, J=8 Hz), 9.76 (1H, d, J=8 Hz)

(16) p-Nitrobenzyl 7-(2-phenylacetamido)-3-vinylthiomethyl-3-cephem-4-carboxylate IR (Nujol): 3270, 1760, 1720, 1660, 1525, 1350 cm$^{-1}$ NMR (DMSO-d$_6$, δ): 3.56 (2H, s), 3.67 (2H, broad s), 3.69 and 4.01 (2H, ABq, J=14 Hz), 5.17 (1H, d, J=5 Hz), 5.19 (1H, d, J=17 Hz), 5.21 (1H, d, J=10 Hz), 5.43 (2H, s), 5.74 (1H, dd, J=5 Hz and 8 Hz), 6.53 (1H, dd, J=10 Hz and 17 Hz), 7.27 (5H, s), 7.71 (2H, d, J=8 Hz), 8.25 (2H, d, J=8 Hz), 9.12 (1H, d, J=8 Hz)

(17) 7-[2-Carboxymethoxyimino-2-{2-(2,2,2-trifluoroacetamido)thiazol-4-yl}acetamido]-3-vinylthiomethyl-3-cephem-4-carboxylic acid (syn isomer)

IR (Nujol): 3250, 1770, 1720, 1655, 1580, 1540, 1270, 1210 cm$^{-1}$

(18) 7-[2-Carboxymethoxyimino-2-(2-aminothiazol-4-yl)acetamido]-3-vinylthiomethyl-3-cephem-4-carboxylic acid (syn isomer)

IR (Nujol): 1760, 1680–1620, 1580, 1240 cm$^{-1}$

(19) 7-[2-Allyloxyimino-2-(5-amino-1,2,4-thiadiazol-3-yl)acetamido]-3-[(Z)-2-(2-methyl-5-pyridyl)vinylthiomethyl]-3-cephem-4-carboxylic acid (syn isomer)

IR (Nujol): 3300, 3150, 1760, 1670, 1610, 1580, 1520 cm$^{-1}$

(20) Benzhydryl 7-[2-allyloxyimino-2-(5-amino-1,2,4-thiadiazol-3yl)acetamido]-3-[(Z)-2-(2-methyl-5-pyridyl)vinylthiomethyl]-3-cephem-4-carboxylate (syn isomer)

IR (Nujol): 3300, 3150, 1780, 1720, 1680, 1610, 1530, 1490, 1300, 1240 cm$^{-1}$ NMR (CDCl$_3$, δ): 2.50 (3H, s), 3.50 (2H, broad s), 3.72 and 3.95 (2H, ABq, J=14 Hz), 4.6–4.9 (2H, m), 5.1–6.3 (3H, m), 5.10 (1H, d, J=5 Hz), 6.01 (1H, dd, J=5 Hz and 8 Hz), 6.20 (2H, s), 6.75 (2H, broad s), 6.98 (1H, s), 7.1–7.5 (11H, m), 7.5–7.8 (1H, m), 8.35 (1H, d, J=8 Hz), 8.4 (1H, m)

(21) 7-[2-Allyloxyimino-2-(2-aminothiazol-4-yl)acetamido]-3-[(Z)-2-(2-methyl-5-pyridyl)vinylthiomethyl]-3-cephem-4-carboxylic acid (syn isomer)

IR (Nujol): 3300, 3150, 1760, 1670, 1610, 1580, 1520 cm$^{-1}$

(22) Benzhydryl 7-[2-allyloxyimino-2-(2-aminothiazol-4-yl)acetamido]-3-[(Z)-2-(2-methyl-5-pyridyl)vinylthiomethyl]-3-cephem-4-carboxylate (syn isomer)

IR (Nujol): 3300, 3150, 1780, 1720, 1670, 1610, 1530, 1300, 1240 cm$^{-1}$

(23) Benzhydryl 7-[2-allyloxyimino-2-(2-formamidothiazol-4-yl)acetamido]-3-[(Z)-2-(2-methyl-5-pyridyl)vinylthiomethyl]-3-cephem-4-carboxylate (syn isomer)

IR (Nujol): 3250, 3150, 1780, 1710, 1690, 1660, 1540, 1270, 1240 cm$^{-1}$

NMR (CDCl$_3$, δ): 2.52 (3H, s), 3.53 (2H, broad s), 3.09 and 4.02 (2H, ABq, J=14 Hz), 4.6–4.8 (2H, m), 5.0–6.2 (3H, m), 5.10 (1H, d, J=5 Hz), 6.06 (1H, dd, J=5 Hz and 8 Hz), 6.23 (2H, s), 7.00 (1H, s), 7.1–7.7 (12H, m), 7.7–8.0 (1H, m), 8.48 (1H, s), 8.5 (1H, m)

(24) Benzhydryl 7-[2-(5-amino-1,2,4-thiadiazol-3-yl)-2-ethoxyiminoacetamido]-3-[(Z)-2-(2-methyl-5-pyridyl)vinylthiomethyl]-3-cephem-4-carboxylate (syn isomer)

IR (Nujol): 1770, 1710, 1670, 1610, 1515 cm$^{-1}$

NMR (DMSO-d$_6$, δ): 1.24 (3H, t, J=7 Hz), 2.36–2.60 (3H, s, hidden), 3.66 (2H, broad s), 3.74, 3.98 (2H, ABq, J=14 Hz), 4.18 (2H, q, J=7 Hz), 5.26 (1H, d, J=5 Hz), 5.92 (1H, dd, J=5 Hz, 8 Hz), 6.41 (2H, s), 6.98 (1H, s), 7.12–7.60 (11H, m), 7.70 (1H, dd, J=3 Hz, 8 Hz), 8.10 (2H, broad s), 8.45 (1H, d, J=3 Hz), 9.58 (1H, d, J=8 Hz)

(25) 7-[2-(5-Amino-1,2,4-thiadiazol-3-yl)-2-ethoxyiminoacetamido]-3-[(Z)-2-(2-methyl-5-pyridyl)vinylthiomethyl]-3-cephem-4-carboxylic acid (syn isomer)

mp: 175° C. (dec.)

IR (Nujol): 1770, 1665, 1610, 1530 cm$^{-1}$

(26) Benzhydryl 7-[2-(5-amino-1,2,4-thiadiazol-3-yl)-2-ethoxyiminoacetamido]-3-[(Z)-2-cyanovinylthiomethyl]-3-cephem-4-carboxylate (syn isomer)

IR (Nujol): 2210, 1780, 1720, 1675, 1610 cm$^{-1}$

NMR (DMSO-d$_6$, δ): 1.25 (3H, t, J=7 Hz), 3.65 (2H, broad s), 4.0 (2H, m), 4.20 (2H, q, J=7 Hz), 5.28 (1H, d, J=5 Hz), 5.63 (1H, d, J=11 Hz), 5.97 (1H, dd, J=8 Hz, 5 Hz), 6.95 (1H, s), 7.17–7.67 (10H, m), 7.53 (1H, d, J=11 Hz), 8.10 (2H, broad s), 9.60 (1H, d, J=8 Hz)

(27) 7-[2-(5-Amino-1,2,4-thiadiazol-3yl)-2-ethoxyiminoacetamido]-3-[(Z)-2-cyanovinylthiomethyl]-3-cephem-4-carboxylic acid (syn isomer)

IR (Nujol): 3300, 2210, 1770, 1680, 1620 cm$^{-1}$

(28) Benzhydryl 7-[2-(2-formamidothiazol-4-yl)-2-methoxyiminoacetamido]-3-[(Z)-2-cyanovinylthiomethyl]-3-cephem-4-carboxylate (syn isomer)

IR (Nujol): 2210, 1780, 1710, 1680, 1660 cm$^{-1}$

NMR (DMSO-d$_6$, δ): 3.65 (2H, broad s), 3.9 (3H, s) 4.0 (2H, broad s), 5.30 (1H, d, J=5 Hz), 5.63 (1H, d, J=11 Hz), 5.93 (1H, dd, J=8 Hz, 5 Hz), 6.95 (1H, s), 7.2–7.70 (11H, m), 7.52 (1H, d, J=11 Hz), 8.52 (1H, s), 9.70 (1H, d, J=8 Hz)

(29) Benzhydryl 7-[2-(2-aminothiazol-4-yl)-2-methoxyiminoacetamido]-3-[(Z)-2-cyanovinylthiomethyl]-3-cephem-4-carboxylate (syn isomer)

IR (Nujol): 2210, 1770, 1715, 1670, 1610 cm$^{-1}$

(30) 7-[2-(2-Aminothiazol-4-yl)-2-methoxyiminoacetamido]-3-[(Z)-2-cyanovinylthiomethyl]-3-cephem-4-carboxylic acid (syn isomer)

IR (Nujol): 3300, 2220, 1775, 1670 cm$^{-1}$

(31) Benzhydryl 7-[2-allyloxyimino-2-(2-formamidothiazol-4-yl)acetamido]-3-[(Z)-2-cyanovinylthiomethyl]-3-cephem-4-carboxylate (syn isomer)

IR (Nujol): 2210, 1780, 1715, 1680 cm$^{-1}$

NMR (DMSO-d$_6$, δ): 3.67 (2H, broad s), 3.83–4.17 (2H, m), 4.67 (2H, d, J=5 Hz), 5.12–6.10 (4H, m), 5.30 (1H, d, J=5 Hz), 5.65 (1H, d, J=11 Hz), 6.95 (1H, s), 7.2–7.7 (11H, m), 7.53 (1H, d, J=11 Hz), 8.53 (1H, s), 9.73 (1H, d, J=8 Hz)

(32) Benzhydryl 7-[2-allyloxyimino-2-(2-aminothiazol-4-yl)acetamido]-3-[(Z)-2-cyanovinylthiomethyl]-3-cephem-4-carboxylate (syn isomer)

IR (Nujol): 2210, 1770, 1715, 1665, 1610 cm$^{-1}$

(33) 7-[2-Allyloxyimino-2-(2-aminothiazol-4-yl)acetamido]-3-[(Z)-2-cyanovinylthiomethyl]-3-cephem-4-carboxylic acid (syn isomer)

IR (Nujol): 3300, 2220, 1770, 1670, 1620 cm$^{-1}$

(34) Benzhydryl 7-[2-(5-amino-1,2,4-thiadiazol-3-yl)-2-methoxyiminoacetamido-3-[(Z)-2cyanovinylthiomethyl]-3-cephem-4-carboxylate (syn isomer)

IR (Nujol): 2210, 1770, 1715, 1670, 1610 cm$^{-1}$

NMR (DMSO-d$_6$, δ): 3.63 (2H, broad s), 3.9–4.2 (2H, m), 3.92 (3H, s), 5.27 (1H, d, J=5 Hz), 5.63 (1H, d, J=11 Hz), 5.93 (1H, dd, J=8 Hz, 5 Hz), 6.95 (1H, s), 7.2–7.6 (10H, m), 7.53 (1H, d, J=11 Hz), 8.10 (2H, broad s) 9.6 (1H, d, J=8 Hz)

(35) 7-[2-(5-Amino-1,2,4-thiadiazol-3-yl)-2-methoxyiminoacetamido]-3-[(Z)-2-cyanovinylthiomethyl]-3-cephem-4-carboxylic acid (syn isomer)

IR (Nujol): 3300, 2210, 1770, 1670, 1620 cm$^{-1}$

(36) Benzhydryl 7-[2-((Z)-2-cyanovinylthio)acetamido]-3-[(Z)-2-cyanovinylthiomethyl]-3-cephem-4-carboxylate IR (Nujol): 2210, 1780, 1715, 1665 cm$^{-1}$ NMR (DMSO-d$_6$, δ): 3.7 (2H, broad s), 3.76 (2H, s), 3.8–4.3 (2H, m), 5.30 (1H, d, J=5 Hz), 5.7 (1H, d, J=10 Hz), 5.75 (1H, d, J=10 Hz), 5.83 (1H, dd, J=8 Hz, 5 Hz), 7.0 (1H, s), 7.2–7.69 (10H, m), 7.58 (1H, d, J=10 Hz), 7.72 (1H, d, J=10 Hz), 9.27 (1H, d, J=8 Hz)

(37) 7-[2-((Z)-2-Cyanovinylthio)acetamido]-3-[(Z)-2-cyanovinylthiomethyl]-3-cephem-4-carboxylic acid IR (Nujol): 3300, 2210, 1775, 1710, 1670 cm$^{-1}$

(38) Benzhydryl 7-[2-(5-amino-1,2,4-thiadiazol-3-yl)-2-ethoxyiminoacetamido]-3-[(E)-2-cyanovinylthiomethyl]-3-cephem-4-carboxylate (syn isomer)

IR (Nujol): 2210, 1780, 1720, 1680 cm$^{-1}$

NMR (DMSO-d$_6$, δ): 1.24 (3H, t, J=7 Hz), 3.48–3.7 (2H, m), 3.80 (2H, broad s), 4.12 (2H, q, J=7 Hz), 5.15 (1H, d, J=5 Hz), 5.52 (1H, d, J=15 Hz), 3.81 (1H, dd, J=5 Hz), 6.82 (1H, s), 7.0–7.5 (10H, m), 7.61 (1H, d, J=15 Hz), 7.93 (2H, broad s), 9.38 (1H, d, J=8 Hz)

(39) 7-[2-(5-Amino-1,2,4-thiadiazol-3-yl)-2-ethoxyiminoacetamido]-3-[(E)-2-cyanovinylthiomethyl]-3-cephem-4-carboxylic acid (syn isomer)

IR (Nujol): 3300, 2220, 1780, 1675, 1620 cm$^{-1}$

(40) Benzhydryl 7-[2-(2-formamidothiazol-4-yl)-2-methoxyiminoacetamido]-3-[(E)-2-cyanovinylthiomethyl]-3-cephem-4-carboxylate (syn isomer)

IR (Nujol): 2210, 1780, 1715, 1680 cm$^{-1}$

NMR (DMSO-d$_6$, δ): 3.7 (2H, broad s), 3.97–4.1 (2H, m), 3.97 (3H, s), 5.33 (2H, d, J32 5 Hz), 5.68 (1H, d, J=16 Hz), 5.98 (1H, dd, J=8 Hz, 5 Hz), 7.02 (1H, s), 7.3–7.67 (10H, m), 7.8 (1H, d, J=16 Hz), 8.57 (1H, s), 9.75 (1H, d, J=8 Hz)

(41) Benzhydryl 7-[2-(2-aminothiazol-4yl)-2-methoxyiminoacetamido]-3-[(E)-2-cyanovinylthiomethyl]-3-cephem-4-carboxylate (syn isomer)

IR (Nujol): 2220, 1780, 1720, 1675, 1615 cm$^{-1}$

(42) 7-[2-(2-Aminothiazol-4-yl)-2-methoxyiminoacetamido]-3-[(E)-2-cyanovinylthiomethyl]-3-cephem-4-carboxylic acid (syn isomer)

IR (Nujol): 3300, 2210, 1765, 1665, 1620 cm$^{-1}$

(43) Benzhydryl 7-[2-allyloxyimino-2-(2-formamidothiazol-4-yl)acetamido]-3-[(E)-2-cyanovinylthiomethyl]-3-cephem-4-carboxylate (syn isomer)

IR (Nujol): 2220, 1780, 1720, 1680 cm$^{-1}$

NMR (DMSO-d$_6$, δ): 3.54–3.78 (2H, m), 3.78–3.9 (2H, m), 4.67 (2H, d, J=5 Hz), 5.2–6.18 (5H, m), 5.63 (1H, d, J=14 Hz), 6.98 (1H, s), 7.25–7.67 (11H, m), 7.78 (1H, d, J=14 Hz), 8.53 (1H, s), 9.8 (1H, d, J=8 Hz)

(44) Benzhydryl 7-[2-allyloxyimino-2-(2-aminothiazol-4-yl)acetamido]-3-[(E)-2-cyanovinylthiomethyl]-3-cephem-4-carboxylate (syn isomer)

IR (Nujol): 2220, 1780, 1720, 1670, 1615 cm$^{-1}$

(45) 7-[2-Allyloxyimino-2-(2-aminothiazol-4-yl)acetamido]-3-[(E)-2-cyanovinylthiomethyl]-3-cephem-4-carboxylic acid (syn isomer)

IR (Nujol): 2200, 1765, 1660 cm$^{-1}$

(46) Benzhydryl 7-[2-allyloxyimino-2-(5-amino-1,2,4-thiadiazol-3-yl)acetamido]-3-[(E)-2-cyanovinylthiomethyl]-3-cephem-4-carboxylate (syn isomer)

IR (Nujol): 2210, 1770, 1720, 1670, 1610 cm$^{-1}$

NMR (DMSO-d$_6$, δ): 3.65 (2H, broad s), 3.90 (2H, broad s), 4.7 (2H, d, J=5 Hz), 5.13–6.13 (4H, m), 5.3 (1H, d, J=5 Hz), 5.67 (1H, d, J=16 Hz), 7.0 (1H, s), 7.2–7.67 (10H, m), 7.8 (1H, d, J=16 Hz), 8.13 (2H, broad s), 9.63 (1H, d, J=8 Hz)

(47) 7-[2-Allyloxyimino-2-(5-amino-1,2,4-thiadiazol-3-yl)acetamido]-3-[(E)-2-cyanovinylthiomethyl]-3-cephem-4-carboxylic acid (syn isomer)

IR (Nujol): 3300, 2220, 1770, 1675, 1620 cm$^{-1}$

(48) 7-Amino-3-[(Z)-2-(3-pyridyl)vinylthiomethyl]-3-cephem-4-carboxylic acid

IR (Nujol): 1780, 1620 cm$^{-1}$

(49) Benzhydryl 7-amino-3-[(Z)-2-(3-pyridyl)vinylthiomethyl]-3-cephem-4-carboxylate dihydrochloride IR (Nujol): 1780, 1700, 1580 cm$^{-1}$

(50) Benzhydryl 7-(2-hydroxybenzylideneamino)-3-[(Z)-2-(3-pyridyl)vinylthiomethyl]-3-cephem-4-carboxylate IR (Nujol): 1770, 1710, 1620 cm$^{-1}$ NMR (DMSO-d$_6$, δ): 3.5–4.0 (4H, m), 5.4 (1H, d, J=5 Hz), 5.7 (1H, d, J=5 Hz), 6.4 (2H, m), 6.8–7.0 (3H, m), 7.1–7.7 (14H, m), 7.7–7.9 (1H, m), 8.3–8.6 (2H, m), 8.77 (1H, s)

EXAMPLE 32

A solution of 7-[2-methoxyimino-2-{2-(2,2,2-trifluoroacetamido)thiazol-4-yl}acetamido]-3-vinylthiomethyl-3-cephem-4-carboxylic acid (syn isomer) (380 mg) and sodium acetate (937 mg) in water (8 ml) was stirred at ambient temperature overnight. The mixture was adjusted to pH 1.6 with 6N-hydrochloric acid. This solution was subjected to column chormatography on macroporous non-ionic adsorption resin "Diaion HP 20" (15 ml). After the column was washed with water, the elution was carried out with 25% aqueous isopropyl alcohol. The eluates containing the object compound were collected, evaporated to remove isopropyl alcohol under reduced pressure and lyophilized to give 7-[2-(2-aminothiazol-4-yl)-2-methoxyiminoacetamido]-3-vinylthiomethyl-3-cephem-4-carboxylic acid hydrochloride (syn isomer) (170 mg).

mp: 195°–205° C. (dec.)

IR (Nujol): 1760, 1650, 1580, 1520 cm$^{-1}$

NMR (DMSO-d$_6$, δ): 3.1–4.1 (4H, m), 3.83 (3H, s), 5.14 (1H, d, J=5 Hz), 5.15 (1H, d, J=17 Hz), 5.18 (1H, d, J=10 Hz), 5.70 (1H, dd, J=5 Hz and 8 Hz), 6.52 (1H, dd, J=10 Hz and 17 Hz), 6.72 (1H, s), 7.15 (2H, broad s), 9.52 (1H, d, J=8 Hz)

EXAMPLE 33

The following compounds were obtained according to similar manners to those of Examples 16, 17 and 32.

(1) 7-[2-(2-Aminothiazol-4-yl)-2-(3-thiethanyloxyimino)acetamido]-3-[(Z)-2-(3-pyridyl)vinylthiomethyl]-3-cephem-4-carboxylic acid (anti isomer)

mp: 150° C. (dec.)

IR (Nujol): 1780, 1660, 1520 cm$^{-1}$ (2) 7-[2-(2-Aminothiazol-4yl)-2-isopropoxyiminoacetamido]-3-[(Z)-2-(1-methyl-3-pyridinio)vinylthiomethyl]-3-cephem-4-carboxylate (syn isomer) mp: 145° C. (dec.)

IR (Nujol): 1770, 1670, 1600 cm$^{-1}$ (3) 7-[2-(5-Amino-1,2,4-thiadiazol-3-yl)-2-ethoxyiminoacetamido]-3-(2-trimethylsilylethynylthiomethyl)-3-cephem-4-carboxylic acid (syn isomer)

mp: 123° C. (dec.)

IR (Nujol): 3300, 3190, 2080, 1765, 1670, 1615, 1515 cm$^{-1}$ (4) Benzhydryl 7-[2-(2-aminothiazol-4-yl)-2-(3-thietanyloxyimino)acetamido]-3-[(Z)-2-(3-pyridyl)-vinylthiomethyl]-3-cephem-4-carboxylate (syn isomer)

IR (Nujol): 1780, 1720, 1670, 1620, 1530 cm$^{-1}$

NMR (DMSO-d$_6$, δ): 3.4–4.0 (6H, m), 5.1–5.4 (2H, m), 5.88 (1H, dd, J=5 Hz, 8 Hz), 6.40, 6.53 (2H, ABq, J=12 Hz), 6.80 (1H, s, 6.97 (1H, s), 7.10–7.60 (11H, m), 7.80 (1H, m), 8.40 (1H, dd, J=2 Hz, 5 Hz), 8.57 (1H, d, J=2 Hz), 9.60 (1H, d, J=8 Hz)

(5) 7-[2-(2-Aminothiazol-4-yl)-2-(3-thietanyloxyimino)acetamido]-3-[(Z)-2-(3-pyridyl)vinylthiomethyl]-3-cephem-4-carboxylic acid (syn isomer)

mp: 160° C. (dec.)

IR (Nujol): 1760, 1660, 1620, 1540 cm$^{-1}$ (6) 7-[2-(2-Aminothiazol-4-yl)-2-(2-cyclopenten-1-yl)oxyiminoacetamido]-3-[(Z)-2-(3-pyridyl)vinylthiomethyl]-3-cephem-4-carboxylic acid (syn isomer)

IR (Nujol): 1760, 1660, 1620, 1580, 1520 cm$^{-1}$

NMR (DMSO-d$_6$, δ): 1.70–2.40 (4H, m), 3.60 (2H, s), 3.90, 4.17 (2H, ABq, J=12 Hz), 5.10–5.40 (2H, m), 5.60–5.95 (2H, m), 5.95–6.15 (1H, m), 6.53, 6.87 (2H, ABq, J=10 Hz), 6.70 (1H, s), 7.55 (1H, dd, J=5 Hz, 8 Hz), 8.00 (1H, d, J=8 Hz), 8.47 (1H, d, J=8 Hz), 8.65 (1H, s), 9.50 (1H, d, J=8 Hz)

(7) 7-[2-(2-Aminothiazol-4-yl)-2-(2-cyclopenten-1-yl)oxyiminoacetamido]-3-[(Z)-2-cyanovinylthiomethyl]-3-cephem-4-carboxylic acid (syn isomer)

IR (Nujol): 3300, 2210, 1760, 1660 cm$^{-1}$

NMR (DMSO-d$_6$, δ): 1.8–2.4 (4H, m), 3.56 (2H, broad s), 3.77 and 4.22 (2H, ABq, J=14 Hz), 5.17 (1H, d, J=5 Hz), 5.2–6.1 (3H, m), 5.69 (1H, d, J=11 Hz), 5.73 (1H, dd, J=8 Hz, 5 Hz), 6.67 (1H, s), 7.17 (2H, broad s), 7.72 (1H, d, J=11 Hz), 9.48 (1H, d, J=8 Hz)

(8) 7-[2-Carboxymethoxyimino-2-(2-aminothiazol-4-yl)acetamido]-3-vinylthiomethyl-3-cephem-4-carboxylic acid (syn isomer)

IR (Nujol): 1760, 1680–1620, 1580, 1240 cm$^{-1}$

NMR (DMSO-d$_6$, δ): 3.56 (2H, broad s), 3.72 and 3.93 (2H, ABq, J=18 Hz), 4.57 (2H, s), 5.16 (1H, d, J=17 Hz), 5.17 (1H, d, J=5 Hz), 5.21 (1H, d, J=10 Hz), 5.75 (1H, dd, J=5 Hz and 8 Hz), 6.52 (1H, dd, J=10 Hz and 17 Hz), 6.78 (1H, s), 7.18 (2H, broad s), 9.46 (1H, d, J=8 Hz)

(9) 7-[2-Allyloxyimino-2-(5-amino-1,2,4-thiadiazol-3-yl)acetamido]-3-[(Z)-2-(2-methyl-5-pyridyl)vinylthiomethyl]-3-cephem-4-carboxylic acid (syn isomer)

IR (Nujol): 3300, 3150, 1760, 1670, 1610, 1580, 1520 cm$^{-1}$

(10) Benzhydryl 7-[2-allyloxyimino-2-(5-amino-1,2,4-thiadiazol-3-yl)acetamido]-3-[(Z)-2-(2-methyl-5-pyridyl)vinylthiomethyl]-3-cephem-4-carboxylate (syn isomer)

IR (Nujol): 3300, 3150, 1780, 1720, 1680, 1610, 1530, 1490, 1300, 1240 cm$^{-1}$

(11) 7-[2-Allyloxyimino-2-(2-aminothiazol-4-yl)acetamido]-3-[(Z)-2-(2-methyl-5-pyridyl)vinylthiomethyl]-3-cephem-4-carboxylic acid (syn isomer)

IR (Nujol): 3300, 3150, 1760, 1670, 1610, 1580, 1520 cm$^{-1}$

(12) Benzhydryl 7-[2-allyloxyimino-2-(2-aminothiazol-4-yl)acetamido]-3-[(Z)-2-(2-methyl-5-pyridyl)-vinylthiomethyl]-3-cephem-4-carboxylate (syn isomer)

IR (Nujol): 3300, 3150, 1780, 1720, 1670, 1610, 1530, 1300, 1240 cm$^{-1}$

NMR (CDCl$_3$, δ): 2.50 (3H, s), 3.53 (2H, broad s), 3.67 and 4.00 (2H, ABq, J=14 Hz), 4.6–4.9 (2H, m), 5.09 (1H, d, J=5 Hz), 5.2–6.0 (3H, m), 5.99 (1H, dd, J=5 Hz and 8 Hz), 6.23 (2H, s), 6.83 (1H, s), 7.0 (1H, s), 7.1–7.5 (11H, m), 7.5–7.8 (1H, m), 8.4–8.6 (1H, m)

(13) Benzhydryl 7-[2-(5-amino-1,2,4-thiadiazol-3-yl)-2-ethoxyiminoacetamido]-3-[(Z)-2-(2-methyl-5-pyridyl)vinylthiomethyl]-3-cephem-4-carboxylate (syn isomer)

IR (Nujol): 1770, 1710, 1670, 1610, 1515 cm$^{-1}$

(14) 7-[2-(5-Amino-1,2,4-thiadiazol-3-yl)-2-ethoxyiminoacetamido]-3-[(Z)-2-(2-methyl-5-pyridyl)vinylthiomethyl]-3-cephem-4-carboxylic acid (syn isomer)

mp: 175° C. (dec.)

IR (Nujol): 1770, 1665, 1610, 1530 cm$^{-1}$

(15) Benzhydryl 7-[2-(5-amino-1,2,4-thiadiazol-3-yl)-2-ethoxyiminoacetamido]-3-[(Z)-2-cyanovinylthiomethyl]-3-cephem-4-carboxylate (syn isomer)

IR (Nujol): 2210, 1780, 1720, 1675, 1610 cm$^{-1}$

(16) 7-[2-(5-Amino-1,2,4-thiadiazol-3-yl)-2-ethoxyiminoacetamido]-3-[(Z)-2-cyanovinylthiomethyl]-3-cephem-4-carboxylic acid (syn isomer)

IR (Nujol): 3300, 2210, 1770, 1680, 1620 cm$^{-1}$

(17) Benzhydryl 7-[2-(2-aminothiazol-4-yl)-2-methoxyiminoacetamido]-3-[(Z)-2-cyanovinylthiomethyl]-3-cephem-4-carboxylate (syn isomer)

IR (Nujol): 2210, 1770, 1715, 1670, 1610 cm$^{-1}$

NMR (DMSO-d$_6$, δ): 3.7 (2H, broad s), 3.80–4.2 (2H, m), 3.88 (3H, s), 5.3 (1H, d, J=5 Hz), 5.68 (1H, d, J=11 Hz), 5.93 (1H, dd, J=8 Hz, 5 Hz), 6.80 (1H, s), 6.98 (1H, s), 7.1–7.7 (12H, m), 7.61 (1H, d, J=11 Hz), 9.67 (1H, d, J=8 Hz)

(18) 7-[2-(2-Aminothiazol-4-yl)-2-methoxyiminoacetamido]-3-[(Z)-2-cyanovinylthiomethyl]-3-cephem-4-carboxylic acid (syn isomer)

IR (Nujol): 3300, 2220, 1775, 1670 cm$^{-1}$

(19) Benzhydryl 7-[2-allyloxyimino-2-(2-aminothiazol-4-yl)acetamido]-3-[(Z)-2-cyanovinylthiomethyl]-3-cephem-4-carboxylate (syn isomer)

IR (Nujol): 2210, 1770, 1715, 1665, 1610 cm$^{-1}$

NMR (DMSO-d$_6$, δ): 3.65 (2H, broad s), 3.8–4.2 (2H, m), 3.60 (2H, d, J=5 Hz), 5.0–6.1 (4H, m), 5.3 (1H, d, J=5 Hz), 5.63 (1H, d, J=11 Hz), 6.75 (1H, s), 6.95 (1H, s), 7.0–7.7 (12H, m), 7.6 (1H, d, J=11 Hz), 9.63 (1H, d, J=8 Hz)

(20) 7-[2-Allyloxyimino-2-(2-aminothiazol-4-yl)acetamido]-3-[(Z)-2-cyanovinylthiomethyl]-3-cephem-4-carboxylic acid (syn isomer)

IR (Nujol): 3300, 2220, 1770, 1670, 1620 cm$^{-1}$

(21) Benzhydryl 7-[2-(5-amino-1,2,4-thiadiazol-3-yl)-2-methoxyiminoacetamido]-3-[(Z)-2-cyanovinylthiomethyl]-3-cephem-4-carboxylate (syn isomer)

IR (Nujol): 2210, 1770, 1715, 1670, 1610 cm$^{-1}$

(22) 7-[2-(5-Amino-1,2,4-thiadiazol-3-yl)-2-methoxyiminoacetamido]-3-[(Z)-2-cyanovinylthiomethyl]-3-cephem-4-carboxylic acid (syn isomer)

IR (Nujol): 3300, 2210, 1770, 1670, 1620 cm$^{-1}$

(23) Benzhydryl 7-[2-(5-amino-1,2,4-thiadiazol-3-yl)-2-ethoxyiminoacetamido]-3-[(E)-2-cyanovinylthiomethyl]-3-cephem-4-carboxylate (syn isomer)

IR (Nujol): 2210, 1780, 1720, 1680 cm$^{-1}$

(24) 7-[2-(5-Amino-1,2,4-thiadiazol-3-yl)-2-ethoxyiminoacetamido]-3-[(E)-2-cyanovinylthiomethyl]-3-cephem-4-carboxylic acid (syn isomer)

IR (Nujol): 3300, 2220, 1780, 1675, 1620 cm$^{-1}$

(25) Benzhydryl 7-[2-(2-aminothiazol-4-yl)-2-methoxyiminoacetamido]-3-[(E)-2-cyanovinylthiomethyl]-3-cephem-4-carboxylate (syn isomer)

IR (Nujol): 2220, 1780, 1720, 1675, 1615 cm$^{-1}$

NMR (DMSO-d$_6$, δ): 3.4–3.75 (2H, m), 3.77 (3H, s), 3.8–4.0 (2H, m), 5.15 (1H, d, J=5 Hz), 5.52 (1H, d, J=16 Hz), 5.77 (1H, dd, J=8 Hz, 5 Hz), 6.61 (1H, s), 6.81 (1H, s), 7.03 (2H, broad s), 7.1–7.5 (10H, m), 7.62 (1H, d, J=16 Hz), 9.40 (1H, d, J=8 Hz)

(26) 7-[2-(2-Aminothiazol-4-yl)-2-methoxyiminoacetamido]-3-[(E)-2-cyanovinylthiomethyl]-3-cephem-4-carboxylic acid (syn isomer)

IR (Nujol): 3300, 2210, 1765, 1665, 1620 cm$^{-1}$

(27) Benzhydryl 7-[2-allyloxyimino-2-(2-aminothiazol-4-yl)acetamido]-3-[(E)-2-cyanovinylthiomethyl]-3-cephem-4-carboxylate (syn isomer)

IR (Nujol): 2220, 1780, 1720, 1670, 1615 cm$^{-1}$

NMR (DMSO-d$_6$, δ): 3.5–3.8 (2H, m), 3.93 (2H, broad s), 4.64 (2H, d, J=5 Hz), 5.16–6.2 (5H, m), 5.67 (1H, d, J=15 Hz), 6.8 (1H, s), 7.0 (1H, s), 7.18–7.67 (12H, m), 7.82 (1H, d, J=15 Hz), 9.72 (1H, d, J=8 Hz)

(28) 7-[2-Allyloxyimino-2-(2-aminothiazol-4-yl)acetamido]-3-[(E)-2-cyanovinylthiomethyl]-3-cephem-4-carboxylic acid (syn isomer)

IR (Nujol): 2200, 1765, 1660 cm$^{-1}$

(29) Benzhydryl 7-[2-allyloxyimino-2-(5-amino-1,2,4-thiadiazol-3-yl)acetamido]-3-[(E)-2-cyanovinylthiomethyl]-3-cephem-4-carboxylate (syn isomer)

IR (Nujol): 2210, 1770, 1720, 1670, 1610 cm$^{-1}$

(30) 7-[2-Allyloxyimino-2-(5-amino-1,2,4-thiadiazol-3-yl)acetamido]-3-[(E)-2-cyanovinylthiomethyl]-3-cephem-4-carboxylic acid (syn isomer)

IR (Nujol): 3300, 2220, 1770, 1675, 1620 cm$^{-1}$

EXAMPLE 34

The following compounds were obtained according to a similar manner to that of Example 19.

(1) Benzhydryl 7-[2-(2-formamidothiazol-4-yl)-2-isopropoxyiminoacetamido]-3-[(Z)-2-(1-methyl-3-pyridinio)vinylthiomethyl]-3-cephem-4-carboxylate nitrate (syn isomer)

IR (Nujol): 1780, 1720, 1670, 1540 cm$^{-1}$ (2) 7-[2-(2-Aminothiazol-4-yl)-2-isopropoxyiminoacetamido]-3-[(Z)-2-(1-methyl-3-pyridinio)vinylthiomethyl]-3-cephem-4-carboxylate (syn isomer)

mp: 145° C. (dec.)

IR (Nujol): 1770, 1670, 1600 cm$^{-1}$

EXAMPLE 35

The following compounds were obtained according to a similar manner to that of Example 21.

(1) p-Nitrobenzyl 7-[2-(p-nitrobenzyloxycarbonylmethoxyimino)-2-{2-(2,2,2-trifluoroacetamido)thiazol-4-yl}acetamido]-3-vinylthiomethyl-3-cephem-4-carboxylate (syn isomer)

IR (Nujol): 1760, 1730, 1680, 1605, 1580, 1520, 1350, 1260, 1210 cm$^{-1}$ (2) Benzhydryl 7-[2-(2-formamidothiazol-4-yl)-2-isopropoxyiminoacetamido]-3-[(Z)-2-(1-methyl-3-pyridinio)vinylthiomethyl]-3-cephem-4-carboxylate nitrate (syn isomer)

IR (Nujol): 1780, 1720, 1670, 1540 cm$^{-1}$ (3) Benzhydryl 7-[2-(2-formamidothiazol-4-yl)-2-(3-thietanyloxyimino)acetamido]-3-[(Z)-2-(3-pyridyl)-vinylthiomethyl]-3-cephem-4-carboxylate (syn isomer)

IR (Nujol): 1770, 1660, 1240, 1160 cm$^{-1}$ (4) Benzhydryl 7-[2-(2-aminothiazol-4-yl)-2-(3-thietanyloxyimino)acetamido]-3-[(Z)-2-(3-pyridyl)-vinylthiomethyl]-3-cephem-4-carboxylate (syn isomer)

IR (Nujol): 1780, 1720, 1670, 1620, 1530 cm$^{-1}$ (5) Benzhydryl 7-[2-(2-cyclopenten-1-yl)oxyimino-2-(2-formamidothiazol-4-yl)acetamido]-3-[(Z)-2-(3-pyridyl)vinylthiomethyl]-3-cephem-4-carboxylate (syn isomer)

IR (Nujol): 1770, 1660, 1530 cm$^{-1}$ (6) Benzhydryl 7-[2-(2-cyclopenten-1-yl)oxyimino-2-(2-formamidothiazol-4-yl)acetamido]-3-[(Z)-2-cyanovinylthiomethyl]-3-cephem-4-carboxylate (syn isomer)

IR (Nujol): 2220, 1780, 1720, 1680 cm$^{-1}$ (7) p-Nitrobenzyl 7-[2-methoxyimino-2-{2-(2,2,2-trifluoroacetamido)thiazol-4-yl}acetamido]-3-vinylthiomethyl-3-cephem-4-carboxylate (syn isomer)

IR (Nujol): 1760, 1720, 1670, 1510, 1345, 1250, 1210 cm$^{-1}$ (8) p-Nitrobenzyl 7-(2-phenylacetamido)-3-vinylthiomethyl-3-cephem-4-carboxylate IR (Nujol): 3270, 1760, 1720, 1660, 1525, 1350 cm$^{-1}$ (9) Benzhydryl 7-[2-allyloxyimino-2-(5-amino-1,2,4-thiadiazol-3-yl)acetamido]-3-[(Z)-2-(2-methyl-5-pyridyl)vinylthiomethyl]-3-cephem-4-carboxylate (syn isomer)

IR (Nujol): 3300, 3150, 1780, 1720, 1680, 1610, 1530, 1490, 1300, 1240 cm$^{-1}$

(10) Benzhydryl 7-[2-allyloxyimino-2-(2-aminothiazol-4-yl)acetamido]-3-[(Z)-2-(2-methyl-5-pyridyl)-vinylthiomethyl]-3-cephem-4-carboxylate (syn isomer)

IR (Nujol): 3300, 3150, 1780, 1720, 1670, 1610, 1530, 1300, 1240 cm$^{-1}$

(11) Benzhydryl 7-[2-allyloxyimino-2-(2-formamidothiazol-4-yl)acetamido]-3-[(Z)-2-(2-methyl-5-pyridyl)-vinylthiomethyl]-3-cephem-4-carboxylate (syn isomer)

IR (Nujol): 3250, 3150, 1780, 1710, 1690, 1660, 1540, 1270, 1240 cm$^{-1}$

(12) Benzhydryl 7-[2-(5-amino-1,2,4-thiadiazol-3-yl)-2-ethoxyiminoacetamido]-3-[(Z)-2-(2-methyl-5-pyridyl)vinylthiomethyl]-3-cephem-4-carboxylate (syn isomer)

IR (Nujol): 1770, 1710, 1670, 1610, 1515 cm$^{-1}$

(13) Benzhydryl 7-[2-(5-amino-1,2,4-thiadiazol-3-yl)-2-ethoxyiminoacetamido]-3-[(Z)-2-cyanovinylthiomethyl]-3-cephem-4-carboxylate (syn isomer)

IR (Nujol): 2210, 1780, 1720, 1675, 1610 cm$^{-1}$

(14) Benzhydryl 7-[2-(2-formamidothiazol-4-yl)-2-methoxyiminoacetamido]-3-[(Z)-2-cyanovinylthiomethyl]-3-cephem-4-carboxylate (syn isomer)

IR (Nujol): 2210, 1780, 1710, 1680, 1660 cm$^{-1}$

(15) Benzhydryl 7-[2-(2-aminothiazol-4-yl)-2-methoxyiminoacetamido]-3-[(Z)-2-cyanovinylthiomethyl]-3-cephem-4-carboxylate (syn isomer)

IR (Nujol): 2210, 1770, 1715, 1670, 1610 cm$^{-1}$

(16) Benzhydryl 7-[2-allyloxyimino-2-(2-formamidothiazol-4-yl)acetamido]-3-[(Z)-2-cyanovinylthiomethyl]-3-cephem-4-carboxylate (syn isomer)

IR (Nujol): 2210, 1780, 1715, 1680 cm$^{-1}$

(17) Benzhydryl 7-[2-allyloxyimino-2-(2-aminothiazol-4-yl)acetamido]-3-[(Z)-2-cyanovinylthiomethyl]-3-cephem-4-carboxylate (syn isomer)

IR (Nujol): 2210, 1770, 1715, 1665, 1610 cm$^{-1}$

(18) Benzhydryl 7-[2-(5-amino-1,2,4-thiadiazol-3-yl)-2-methoxyiminoacetamido]-3-[(Z)-2-cyanovinylthiomethyl]-3-cephem-4-carboxylate (syn isomer)

IR (Nujol): 2210, 1770, 1715, 1670, 1610 cm$^{-1}$

(19) Benzhydryl 7-[2-((Z)-2-cyanovinylthio)acetamido]-3-[(Z)-2-cyanovinylthiomethyl]-3-cephem-4-carboxylate IR (Nujol): 2210, 1780, 1715, 1665 cm$^{-1}$

(20) Benzhydryl 7-[2-(5-amino-1,2,4-thiadiazol-3-yl)-2-ethoxyiminoacetamido]-3-[(E)-2-cyanovinylthiomethyl]-3-cephem-4-carboxylate (syn isomer)

IR (Nujol): 2210, 1780, 1720, 1680 cm$^{-1}$

(21) Benzhydryl 7-[2-(2-formamidothiazol-4-yl)-2-methoxyiminoacetamido]-3-[(E)-2-cyanovinylthiomethyl]-3-cephem-4-carboxylate (syn isomer)

IR (Nujol): 2210, 1780, 1715, 1680 cm$^{-1}$

(22) Benzhydryl 7-[2-(2-aminothiazol-4-yl)-2-methoxyiminoacetamido]-3-[(E)-2-cyanovinylthiomethyl]-3-cephem-4-carboxylate (syn isomer)

IR (Nujol): 2220, 1780, 1720, 1675, 1615 cm$^{-1}$

(23) Benzhydryl 7-[2-allyloxyimino-2-(2-formamidothiazol-4-yl)acetamido]-3-[(E)-2-cyanovinylthiomethyl]-3-cephem-4-carboxylate (syn isomer)

IR (Nujol): 2220, 1780, 1720, 1680 cm$^{-1}$

(24) Benzhydryl 7-[2-allyloxyimino-2-(2-aminothiazol-4-yl)acetamido]-3-[(E)-2-cyanovinylthiomethyl]-3-cephem-4-carboxylate (syn isomer)

IR (Nujol): 2220, 1780, 1720, 1670, 1615 cm$^{-1}$

(25) Benzhydryl 7-[2-allyloxyimino-2-(5-amino-1,2,4-thiadiazol-3-yl)acetamido]-3-[(E)-2-cyanovinylthiomethyl]-3-cephem-4-carboxylate (syn isomer)

IR (Nujol): 2210, 1770, 1720, 1670, 1610 cm$^{-1}$

(26) Benzhydryl 7-amino-3-[(Z)-2-(3-pyridyl)vinylthiomethyl]-3-cephem-4-carboxylate dihydrochloride IR (Nujol): 1780, 1700, 1580 cm$^{-1}$

(27) Benzhydryl 7-(2-hydroxybenzylideneamino)-3-[(Z)-2-(3-pyridyl)vinylthiomethyl]-3-cephem-4-carboxylate IR (Nujol): 1770, 1710, 1620 cm$^{-1}$

EXAMPLE 36

To a solution of benzhydryl 7-(2-hydroxybenzylideneamino)-3-[(Z)-2-(3-pyridyl)vinylthiomethyl]-3-cephem-4-carboxylate (2.3 g) in ethyl acetate (46 ml) was added concentrated hydrochloric acid (1 ml) at ambient temperature and the mixture was stirred for 30 minutes to give a precipitate of a viscous oil. The upper layer was removed by decantation and the resultant oil was triturated with a mixture of ethanol and diethyl ether to give benzhydryl 7-amino-3-[(Z)-2-(3-pyridyl)vinylthiomethyl]-3-cephem-4-carboxylate dihydrochloride (2.2 g).

IR (Nujol): 1780, 1700, 1580 cm$^{-1}$

NMR (DMSO-d$_6$, δ): 3.7–4.3 (4H, m), 5.3 (2H, m), 6.90 (1H, s), 7.1–7.7 (10H, m), 8.0 (1H, m), 8.3–9.0 (3H, m)

EXAMPLE 37

The following compound obtained by reacting p-nitrobenzyl 7-[2-(p-nitrobenzyloxycarbonylmethoxyimino)-2-{2-(2,2,2-trifluoroacetamido)thiazol-4-yl}-acetamido]-3-vinylthiomethyl-3-cephem-4-carboxylate (syn isomer) according to a similar manner to that of Example 26.

7-[2-Carboxymethoxyimino-2-{2-(2,2,2-trifluoroacetamido)thiazol-4-yl}-acetamido]-3-vinylthiomethyl-3-cephem-4-carboxylic acid (syn isomer)

IR (Nujol): 3250, 1770, 1720, 1655, 1580, 1540, 1270, 1210 cm$^{-1}$

NMR (DMSO-d$_6$, δ): 3.4–3.7 (2H, m), 3.73 and 3.94 (2H, ABq, J=18 Hz), 4.65 (2H, s), 5.17 (1H, d, J=17 Hz), 5.19 (1H, d, J=5 Hz), 5.22 (1H, d, J=10 Hz), 5.70 (1H, dd, J=5 Hz and 8 Hz), 6.52 (1H, dd, J=10 Hz and 17 Hz), 7.56 (1H, s), 9.67 (1H, d, J=8 Hz)

What we claim is:

1. A cephem compound of the formula:

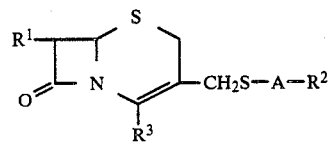

wherein R$^1$ is amino or a group of the formula:

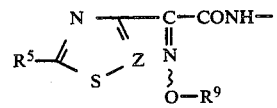

in which
R$^5$ is amino or a protected amino group,
R$^9$ is lower alkyl, lower alkenyl, lower alkynyl, cyclo(lower)alkenyl, carboxy(lower)alkyl, protected carboxy(lower)alkyl, thietanyl, thiolanyl, thianyl, thiepanyl or thiocanyl, and
Z is N or CH,
R$^2$ is cyano, phenyl, pyridyl, lower alkylpyridyl or tri(lower)alkylsilyl,
R$^3$ is carboxy or protected carboxy, and
A is —CH=CH— or —C≡C—,
and pharmaceutically acceptable salt thereof.

2. A compound of claim 1, wherein R$^1$ is amino or a group of the formula:

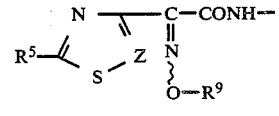

in which
R$^5$ is amino or a protected amino group,
R$^9$ is lower alkyl, lower alkenyl, lower alkynyl, cyclo(lower)alkenyl, carboxy(lower)alkyl, esterified carboxy(lower)alkyl or thietanyl, and
Z is N or CH,
R$^2$ is cyano, phenyl, pyridyl, lower alkylpyridyl, or tri(lower)alkylsilyl,
R$^3$ is carboxy or esterified carboxy and A is —CH=CH— or —C≡C—.

3. A compound of claim 2, wherein $R^1$ is amino or a group of the formula:

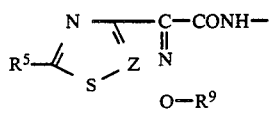

in which
$R^5$, $R^9$ and Z are each as defined in claim 2,
$R^2$ is cyano, phenyl, pyridyl, lower alkylpyridyl, or tri(lower)alkylsilyl, $R^3$ is carboxy, mono- or di- or triphenyl(lower)alkoxycarbonyl, lower alkanoyloxy(lower)alkoxycarbonyl or 4-nitrophenyl(lower)alkoxycarbonyl, and
A is —CH=CH— or —C≡C—.

4. A pharmaceutical antimicrobial composition comprising an antimicrobially effective amount of a compound of claim 1 or pharmaceutically acceptable salt thereof in association with a pharmaceutically acceptable, substantially non-toxic carrier or excipient.

5. A method for treatment of infectious microbial diseases in human beings and animals which comprises administering an antimicrobially effective amount of a compound of claim 1 to said human or animal.

* * * * *